(12) United States Patent
Albani

(10) Patent No.: US 7,022,483 B1
(45) Date of Patent: Apr. 4, 2006

(54) METHODS FOR IDENTIFYING AND ISOLATING ANTIGEN-SPECIFIC T CELLS

(75) Inventor: Salvatore Albani, 629 4th St., Encinitas, CA (US) 92024-3436

(73) Assignee: Salvatore Albani, San Diego, CA (US)

( * ) Notice: Subject to any disclaimer, the term of this patent is extended or adjusted under 35 U.S.C. 154(b) by 0 days.

(21) Appl. No.: 09/421,506

(22) Filed: Oct. 19, 1999

Related U.S. Application Data

(60) Provisional application No. 60/105,018, filed on Oct. 20, 1998.

(51) Int. Cl.
*G01N 33/53* (2006.01)

(52) U.S. Cl. ............... 435/7.1; 435/7.24; 424/1.57; 424/9.34; 424/450

(58) Field of Classification Search ............... 435/7.1, 435/7.2; 424/1.21, 2, 450
See application file for complete search history.

(56) References Cited

U.S. PATENT DOCUMENTS

| | | | |
|---|---|---|---|
| 4,400,376 A | 8/1983 | Sanderson | |
| 4,478,823 A | 10/1984 | Sanderson | |
| 4,690,915 A | 9/1987 | Rosenberg | |
| 4,885,172 A | 12/1989 | Bally et al. | |
| 5,194,253 A | 3/1993 | Garrido | |
| 5,216,132 A | 6/1993 | Basi | |
| 5,283,058 A | 2/1994 | Faustman | |
| 5,468,481 A | 11/1995 | Sharma et al. | |
| 5,595,881 A | 1/1997 | Kendrick et al. | |
| 5,623,056 A | 4/1997 | Tykocinski et al. | |
| 5,635,363 A | 6/1997 | Altman et al. | |
| 5,693,522 A | 12/1997 | Chada et al. | |
| 5,734,023 A | 3/1998 | Nag et al. | |
| 5,750,356 A | 5/1998 | Spack et al. | |
| 5,756,666 A | 5/1998 | Takiguchi et al. | |
| 5,763,585 A | 6/1998 | Nag | |
| 5,773,570 A | 6/1998 | Carson et al. | |
| 5,776,487 A | 7/1998 | Wilson et al. | |
| 5,780,319 A | 7/1998 | Maxfield Wilson et al. | |
| 5,788,963 A | 8/1998 | Murphy et al. | |
| 5,827,516 A | 10/1998 | Urban et al. | |
| 5,834,015 A | 11/1998 | Oleske et al. | |
| 5,861,290 A | 1/1999 | Goldsmith et al. | |
| 5,876,721 A | 3/1999 | Alexander et al. | |
| 5,880,103 A | 3/1999 | Urban et al. | |
| 5,891,689 A | 4/1999 | Takle et al. | |

FOREIGN PATENT DOCUMENTS

WO 97/46256 11/1997

OTHER PUBLICATIONS

Brian, et al., "Allogeneic stimulation of cytotoxic T cells by supported planar membranes," *Proc. Natl. Acad. Sci.* 81:6159-6163 (1984).

Gay, et al., "The Major Histocompatibility Complex-Restricted Antigen Receptor on T Cells," *The Journal of Immunology* 136(6): 2026-2032 (1996).

Marti, et al., "Induction of antigen-presenting capacity in tumor cells upon infection with non-replicating recombinant vaccinia virus encoding murine MHC class II and constimulatory molecules," *Journal of Immunological Methods* 200:191-198 (1997).

Oertli, et al., "Artificial antigen-presenting cells engineered by recombinant vaccinia viruses expressing antigen, MHC class II, and costimulatory molecules elicit proliferation of CD4+ lymphocytes in vitro," *Clin. Exp. Immunol.* 110:144-149 (1997).

Sprent, et al., "Constructing Artificial Antigen-Presenting Cells From Drosophila Cells," *Dendritic Cells in Fundamental and Clinical Immunology* 41:249-254 (1997).

Walden, "Antigen presentation by liposomes as mdoel system for T-B cell interaction," *Eur. J. Immunol.* 18:1851-1854 (1988).

Abitorabi et al., "Differential expression of homing molecules on recirculating lymphocytes from sheep gut, peripheral, and lung lymph," *J. Immunol.* 156:3111-3117 (1996).

(Continued)

*Primary Examiner*—G. R. Ewoldt
(74) *Attorney, Agent, or Firm*—Daniel M. Chambers; Douglas C. Murdock; BioTechnology Law Group

(57) ABSTRACT

The present invention is directed to methods for the identification and isolation of antigen-specific T cells using a novel class of artificial antigen presenting cells. The resulting T cells may be used to produce expanded T cell populations as well as for modulating T cell responses. In general, the artificial antigen presenting cells useful in such methods are liposomes that contain MHC:peptide complexes presented on the outer surface of the liposome. Such artificial antigen presenting cells may also include accessory molecules, co-stimulatory molecules, adhesion molecules, and other molecules irrelevant to T cell binding or modulation that are used in the binding of artificial antigen presenting cells to solid support systems that may be used in the retrieval and identification of antigen-specific T cells.

9 Claims, 24 Drawing Sheets

OTHER PUBLICATIONS

Albani et al, "Positive selection in autoimmunity: Abnormal immune responses to a bacterial dnaJ antigenic determinant in patients with early rheumatoid arthritis," *Nat. Med.* 1:448-452 (1995).

Albani et al., "A multistep molecular mimicry hypothesis for the pathogenesis of rheumatoid arthritis," *Immunology Today* 17:466-470 (1996).

Albani et al., "Diagnostic value of a lymphocyte stimulation test in cow milk protein intolerance," *Annals of Allergy* 63(12):489-492 (1989).

Alexander et al., "Development of high potency universal DR-restricted helper epitopes by modification of high affinity DR-blocking peptides," *Immunity* 1:751-761 (1994).

Altman et al. "Phenotypic analysis of antigen-specific T lymphocytes," *Science* 274: 94-96 (1996).

Anderson et al., "Weak peptide agonists reveal functional differences in B7-1 and B7-2 costimulation of human T cell clones," *J. Immunol.* 159(4):1669-1675 (1997).

Arimilli et al., "Refolding and reconstitution of functionally active complexes of human leukocyte antigen DR2 and myelin basic protein peptide from recombinant $\alpha$ and $\beta$ polypeptide chains," Journal of Biological Chemistry 270 (2):971-977 (1995).

Bachmann et al., "Distinct roles for LFA-1 and CD28 during activation of naïve T cells: Adhesion versus costimulation," *Immunity* 7:549-557 (1997).

Barnardo et al., "Allele-specific HLA-B*15 typing by PCR-SSP and its application to four distinct ethnic populations," *Tissue Antigens* 51(3):293-300 (1998).

Blotta et al., "Cross-linking of the CD40 ligand on human CD4+ T lymphocytes generates a costimulatory signal that up-regulates IL-4 synthesis," *J. Immunol.* 156:3133-3140 (1996).

Bona et al., "Towards development of T-cell vaccines," Immunology Today (Mar. 1998).

Bonnin et al., "Mucosal modulation of immune responses to heat shock proteins in autoimmune arthritis," Biotherapy 10:213-221 (1998).

Bonnin et al., "Ontogeny of synonymous T cell populations with specificity for a self-MHC epitope mimicked by a bacterial homologue: an antigen specific T cell analysis in a non-transgenic system," *Eur. J. Immunol.* (In press) (1999).

Brian et al., "Allogeneic stimulation of cytotoxic T cells by supported planar membranes," *Proc. Natl. Acad. Sci.* 81: 6159-6163 (1984).

Buus et al., "Isolation and characterization of antigen-la complexes involved in T cell recognition," *Cell* 47:1071-1077 (1986).

Carlsson et al., "Protein thiolation and reversible protein-protein conjugation," Biochem. J. 173:723-737 (1978).

Clark et al., "Antigen-specific deletion of cloned T cells using peptide-toxin conjugate complexed with purified class II major histocompatibility complex antigen," Journal of Biological Chemistry 269(1):94-99 (1994).

Crawford et al., "Detection of antigen specific T cells with multivalent soluble class II MHC covalent peptide complexes," *Immunity* 8:675-682 (1998).

Demotz, "DR $\alpha\beta$ dimers released from complexes with invariant chain fail to stimulate alloreactive T cell clones," Eur. J. Immunology 23:2100-2108 (1993).

Demotz, "The ligands of the class II major histocompatibility complex-restricted T cells," Chem. Immunol. 57:18-38 (1993).

Ding et al., "Activation of CD4+ T cells by delivery of the B7 costimulatory signal on bystander antigen-presenting cells (trans-costimulation)," *European Journal of Immunology* 24(4):859-866 (1994).

Dubey et al., "Naïve and effector CD4 T cells differ in their requirements for T cell receptor versus costimulatory signals," *J. Immunol.* 157:3820-3289 (1996).

Eberl et al., "A simple mathematical model for the functional peptide/MHC/TCR interactions," Journal of Immunology 154:219-225 (1995).

Finger et al., "Adhesion through L-selectin requires a threshold hydrodynamic shear," *Nature* 379:266-269 (1996).

Flynn, "CD4 T cell cytokine differentiation: The B cell activation molecule, OX40 ligand, instructs CD4 T cells to express interleukin 4 and upregulates expression of the chemokine receptor, Blr-1," *Journal of Experimental Medicine* 188(2):297-304 (1998).

Frumento et al., "Cellular mechanisms of artificial peptides binding to HLA," International Journal of Artificial Organs, 14:518-522 (1991).

Garboczi et al., "Structure of the complex between human T-cell receptor, viral peptide and HLA-A2," *Nature* 384: 134-141 (1996).

Garcia et al., "Structural basis of plasticity in T cell receptor recognition of a self peptide-MHC antigen," *Science* 279: 1166-1172 (1998).

Gaur et al., "Amelioration of relapsing experimental autoimmune encephalomyelitis with altered myelin basic protein peptides involves different cellular mechanisms," *J. of Neuroimmunol.* 74:149-158 (1997).

Gay et al., "The major histocompatibility complex-restricted antigen receptor on T cells," Journal of Immunology 136 (6):2026-2032 (1986).

Gimmi et al., "Human T-cell clonal anergy is induced by antigen presentation in the absence of B7 costimulation," Proc. Natl. Acad. Sci. 90:6586-6590 (1993).

Grakoui et al., "The immunological synapse: A molecular machine controlling T cell activation," Science 285:221-227 (1999).

Greten et al., "Direct visualization of antigen-specific T cells: HTLV-1 Tax11-19 specific CD8+ T cells are activated in peripheral blood and accumulate in cerebrospinal fluid from HAM/TSP patients," *Proc. Natl. Acad. Sci.* 95:7568-7573 (1998).

Hakamada-Taguchi et al., "Expression and co-stimulatory function of B7-2 on murine CD4+ T cells," *European Journal of Immunology* 28:865-873 (1998).

Hamad et al., "Potent T cell activation with dimeric peptide-major histocompatibility complex class II ligand: The role of CD4 coreceptor," *J. Exp. Med.* 9:1633-1640 (1998).

Harder et al., "Lipid domain structure of the plasma membrane revealed by patching of membrane components," Journal of Cell Biology 141:929-942 (1998).

Hayden et al., "Costimulation by CD28 sFv expressed on the tumor cell surface or as a soluble bispecific molecule targeted to the L6 carcinoma antigen," Tissue Antigens 48:242-254 (1996).

Holmgren et al., "Interaction of cholera toxin and membrane $G_{M1}$ ganglioside of small intestine," Proc. Natl. Acad. Sci. 72:2520-2524 (1975).

Huby et al., "Intracellular phosphotyrosine induction by major histocompatibility complex class II requires co-aggregation with membrane rafts," Journal of Biological Chemistry 274:22591-22596 (1999).

Hunt et al., "Peptides presented to the immune system by the murine class II major histocompatibility complex molecule I-A$^d$," *Science* 256:1817-1820 (1992).

Ignatowicz et al., "The repertoire of T cells shaped by a single MHC/peptide ligand," *Cell* 84:521-529 (1996).

Jameson et al., "Positive selection of thymocytes," *Ann. Rev. Immunol.* 13:93-126 (1995).

Janeway, "Ligands for the T cell receptor: hard times for avidity models," Immunology Today 16(5):223-225 (1995).

Kirberg et al., "Peripheral T cell survival requires continual ligation of the T cell receptor to major histocompatibility complex-encoded molecules," *J. Exp. Med.* 186(8):1269-1275 (1997).

Kitagawa et al., "Enzyme coupled immunoassay of insulin using a novel coupling reagent," J. Biochem. 79:233-236 (1976).

Kurosky et al., "Covalent structure of the β chain of cholera enterotoxin," Journal of Biological Chemistry 252:7257-7264 (1977).

La Cava et al., "Genetic bias in immune response to a cassette shared by different microorganisms in patients with rheumatoid arthritis," *J. Clin. Invest.* 100:658-663 (1997).

Lai, "Determination of the primary structure of cholera toxin B subunit," Journal of Biological Chemistry 252:7249-7256 (1977).

Lehmann et al., "Spreading of T-cell autoimmunity to cryptic determinants of an autoantigen," *Nature* 358(6382):155-157 (1992).

Lessin et al., "Molecular diagnosis of cutaneous T-cell lymphoma: Polymerase chain reaction amplification of T-cell antigen receptor β-chain gene rearrangements," *J. Invest. Dermatol.* 96:299-302 (1991).

Luxembourg et al., "Biomagnetic isolation of antigen-specific CD8+ T cells usable in immunotherapy," *Nature Biotech.* 16:281-285 (1998).

Marsh, D.A., In: *CRC Handbook of Lipid bilayers*, pp 163-168, CRC Press, Boca Raton, FL. (1990).

Marti et al., "Induction of antigen-presenting capacity in tumor cells upon infection with non-replicating recombinant vaccinia virus encoding murine MHC class II and costimulatory molecules," Journal of Immunological Methods 200:191-198 (1997).

Martini et al., "Recurrent juvenile dermatomyositis and cutaneous necrotizing arteritis with molecular mimicry between streptococcal type 5M protein and human skeletal myosin," *J. Peds.* 121:739-742 (1992).

McConnell et al., "Stimulation of T cells by antigen-presenting cells is kinetically controlled by antigenic peptide binding to major histocompatibility complex class II molecules," Proc. Natl. Acad. Sci. 92:2750-2754 (1995).

McRae, "Functional evidence for epitope spreading in the relapsing pathology of experimental autoimmune encephalomyelitis," *Journal of Experimental Medicine* 182:75-85 (1995).

Merritt et al., "Crystal structure of cholera toxin B-pentamer bound to receptor $G_{M1}$ pentasaccharide," Protein Science 3:166-175 (1994).

Mitsunaga et al., "A nested PCR-RFLP method for high-resolution typing of HLA-A alleles," *Eur. J. Immunogenet.* 25(1):15-27 (1998).

Miyazaki et al., "Mice lacking H2-M complexes, enigmatic elements of the MHC class II peptide-loading pathway," Cell 84:531-541 (1996).

Murali-Krishna et al., "Counting antigen-specific CD8 T cells: A reevaluation of bystander activation during viral infection," *Immunity* 8:177-187 (1998).

Murray, "How the MHC selects Th1/Th2 immunity," Immunology Today 19(4) (1998).

Nag et al., "Antigen-specific stimulation of T cell extracellular acidification by MHC class II-peptide complexes," Journal of Immunology 148:2040-2044 (1992).

Nag et al., "Cloned T cells internalize peptide from bound complexes of peptide and purified class II major histocompatibility complex antigen," Journal of Biological Chemistry 268(19):14360-14366 (1993).

Nag et al., "Functionally active recombinant α and β chain-peptide complexes of human major histocompatibility class II molecules," Journal of Biological Chemistry 271(17):10413-10418 (1996).

Nag et al., "Intramolecular charge heterogeneity in purified major histocompatibility class II α and β polypeptide chains," Journal of Biological Chemistry 269(13):10061-10070 (1994).

Nag et al., "N-Linked oligosaccharides of murine major histocompatibility complex class II molecule," Journal of Biological Chemistry 267(31):22624-22629 (1992).

Nag et al., "Purified β-chain of MHC class II binds to CD4 molecules on transfected HeLa cells," Journal of Immunology 150:1358-1364 (1994).

Nag et al., "Separation of complexes of major histocompatibility class II molecules and known antigenic peptide by metal chelate affinity chromatography," Journal of Immunological Methods 169:273-285 (1994).

Nag et al., "Stimulation of T cells by antigenic peptide complexed with isolated chains of major histocompatibility complex class II molecules," *Proc. Natl. Acad. Sci. USA* 90:1604-1608 (1993).

Nag et al., "The role of N-linked oligosaccharides of MHC class II antigens in T cell stimulation," Journal of Immunological Methods 172:95-104 (1994).

Nag et al., "In vitro maximum binding of antigenic peptides to murine MHC class II molecules does not always take place at the acidic pH of the in vivo endosomal compartment," *J. Immunol.* 148:369-372 (1992).

Ogg et al., "Quantitation of HIV-1-specific cytotoxic T lymphocytes and plasma load of viral RNA," Science 279:2103-2106 (1998).

Peterson, "A simplification of the protein assay method of Lowry et al. which is more generally applicable," *Anal. Biochem.* 83:346-356 (1977).

Rao et al., "A trivalent system from vancomycin D-Ala-D-Ala with higher affinity than avidin-biotin," *Science* 280:708-711 (1998).

Rosenberg et al., "Observations on the systemic administration of autologous lymphokine-activated killer cells and recombinant interleukin-2 to patients with metastatic cancer," *N. Engl. J. Med.* 313:1485-1492 (1985).

Rosenberg et al., "Use of tumor-infiltrating lymphocytes and interleukin-2 in the immunotherapy of patients with metastatic melanoma," *N. Engl. J. Med.* 319:1676-1680 (1988).

Rothenberg, "How T cells count," *Science* 273:78-79 (1996).

Rudensky et al., "Sequence analysis of peptides bound to MHC class II molecules," *Nature* 353:622-627 (1991).

Sebzda et al., "Positive and negative thymocyte selection induced by different concentrations of a single peptide," *Science* 263:1615-1618 (1994).

Sette et al., "Efficient of pH on MHC class II-peptide interactions," *J. Immunol.* 148:844-851 (1992).

Sette, *Annals of the New York Academy of Sciences* 86:3296-3300.

Sharma et al., "Antigen-specific therapy of experimental allergic encephalomyelitis by soluble class II major histocompatibility complex-peptide complexes," Proc. Natl. Acad. Sci. 11465-11469 (1991).

Solbach et al., "Lymphocytes play the music but the macrophage calls the tune," Immunology Today 12(1):4-6 (1991).

Spack et al., "Induction of tolerance in experimental autoimmune myasthenia gravis with solubilized MHC class II: Acetylcholine receptor peptide complexes," Journal of Autoimmunity 8:787-807 (1995).

Spinozzi et al., "Local expansion of allergen-specific $CD30^+Th2$-Type $\gamma\delta$ T cells in bronchial asthma," *Mol. Med.* 1(7):821-826 (1995).

Tang et al., "Blockade of CD40-CD40 ligand pathway induces tolerance in murine contact hypersensitivity," *European Journal of Immunology* 27:3143-3150 (1997).

Tietz et al., "$CD4^+$ T cells migrate into inflamed skin only if the express ligands for E- and P-Selectin," *J. Immunol.* 161:963-970 (1998).

Tivol et al., "Costimulation and autoimmunity," Current Opinion in Immunology 8:822-830 (1996).

Van Rensen et al., Liposomes with incorporated MHC class II/peptide complexes as antigen-presenting vesicles for T cell activation. *Pharm. Res* 16(2):198-204 (1999).

Viola et al., "T cell activation determined by T cell receptor number and tunable thresholds," *Science* 273:104-106 (1996).

Viola et al., "T lymphocyte costimulation mediated by reorganization of membrane microdomains," *Science* 283: 680-682 (1999).

Voorter et al., "High-resolution HLA typing for the DQB1 gene by sequence-based typing," *Tissue Antigens* 51(1):80-87 (1998).

Walden et al., "Major histocompatibility complex-restricted and unrestricted activation of helper T cell lines by liposome-bound antigens," J. Mol. Cell. Immunol 2:191-197 (1986).

Ward et al., "Biophysical and structural studies of TCRs and ligands: Implications for T cell signaling," *Curr. Op. Immunol.* 9:97-106 (1997).

Watts et al., "Antigen presentation by supported planar membranes containing affinity-purified $I-A^d$", *Proc. Natl. Acad. Sci.* 81:7564-7568 (1984).

Witt et al., "Antigenic peptide binding to the mouse major histocompatibility complex class II protein $I-E^k$. Peptide stabilization of the quaternary structure of $I-E^k$," *J. Am. Chem. Soc.* 114:3506-3511 (1992).

Wulfing et al., "A receptor/cytoskeletal movement triggered by costimulation during T cell activation," Science 2266: 2269 (1998).

Zhong et al., "Evidence that binding site occupancy is necessary and sufficient for effective major histocompatibility complex (MHC) class II transport through the secretory pathway redefines the primary function of class II-associated invarient chain peptides (CLIP)," *J. Exp. Med.* 284:2061-2066 (1996).

FIG. 16A.
FIG. 16B.
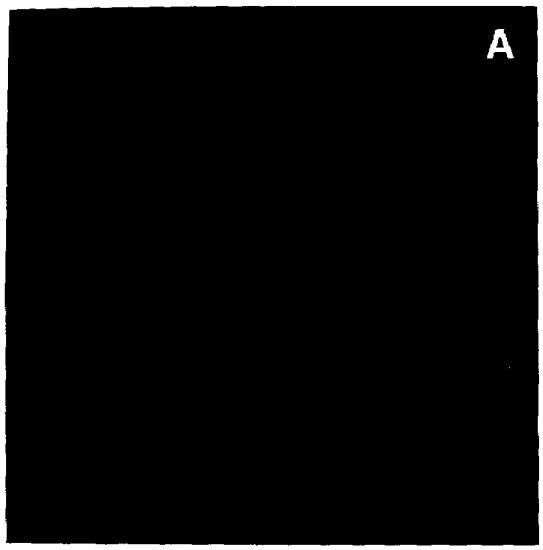
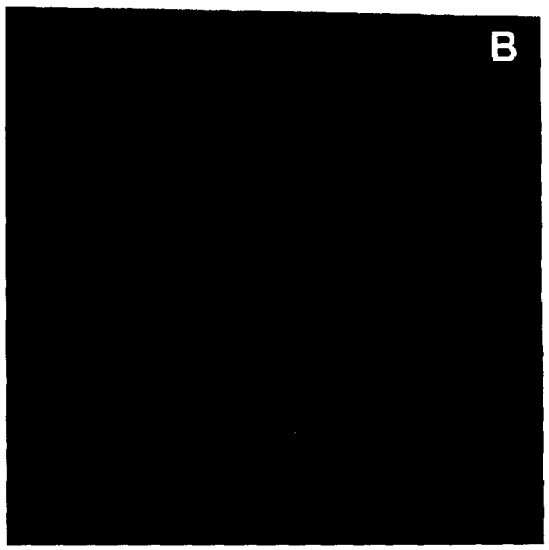
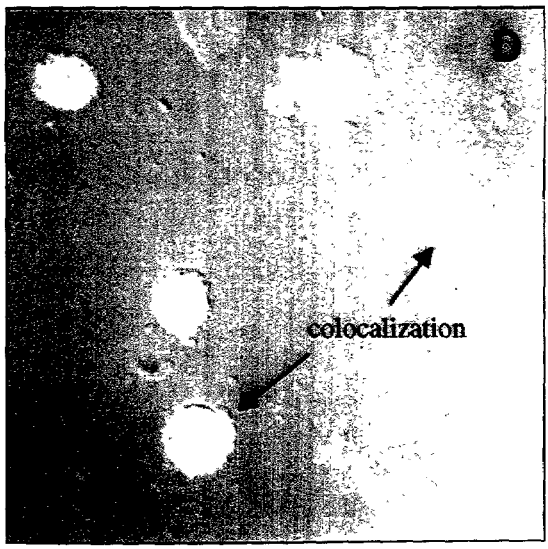
FIG. 16C.
FIG. 16D.

FIG. 19A.
FIG. 19B. 200 20 2 0.1x  200 20 2 0.1x
FIG. 19C.
FIG. 19D. 70 10 1x  70 10 1x

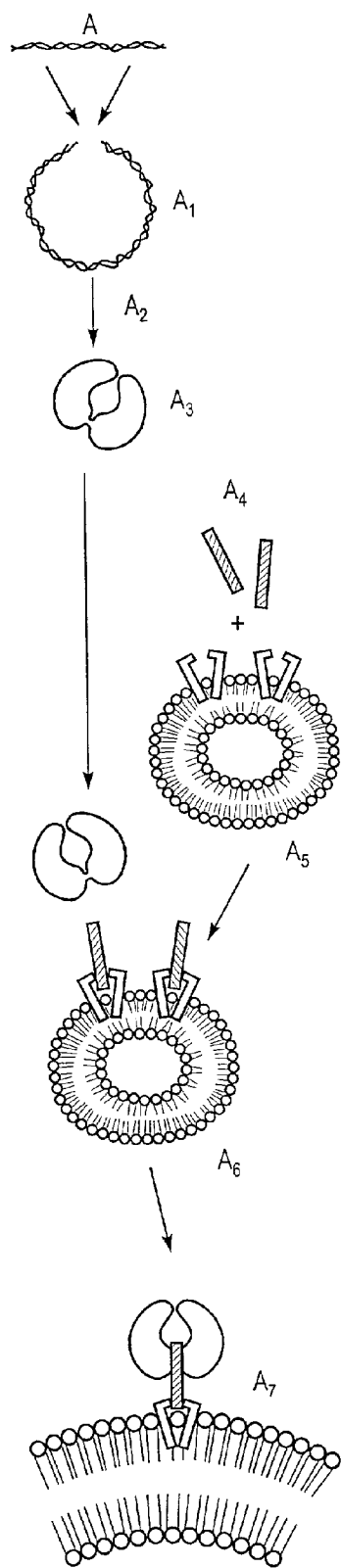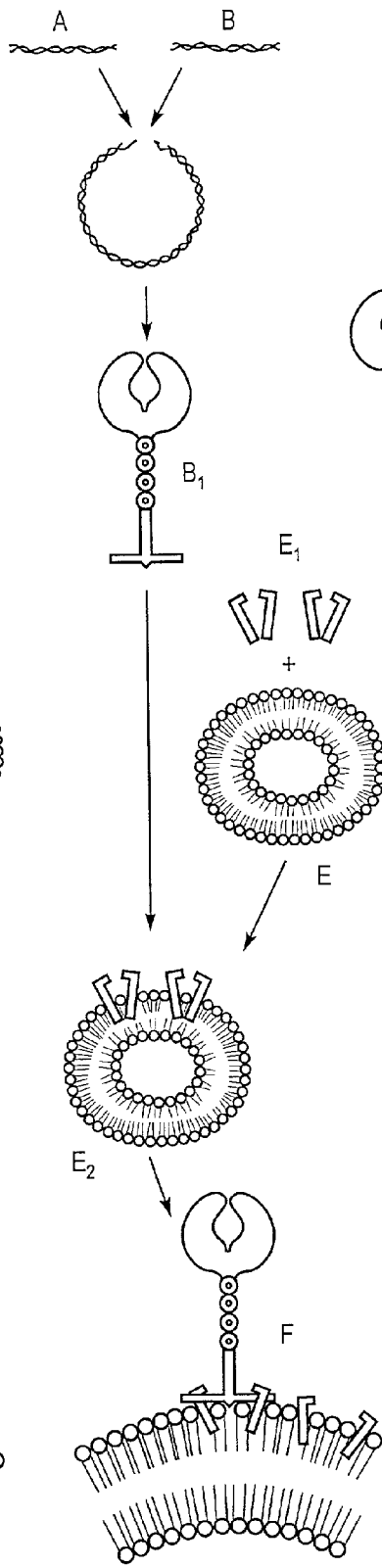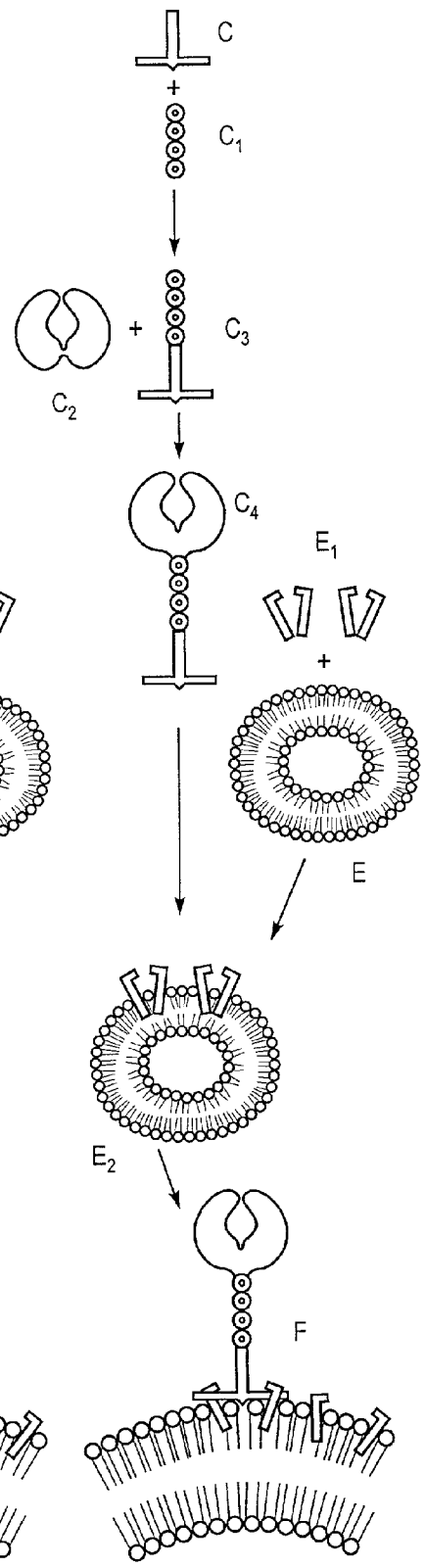
*FIG. 27A*  *FIG. 27B*  *FIG. 27C*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
(A) LENGTH: 3486 base pairs

```
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 225..3287

(xi) SEQUENCE DESCRIPTION: SEQ ID NO:1:

ATCAATCAAC GCCACAGCCT TACCTATTTT AATACAGGGG GAAGTACCTT TGATATTAAA      60

GGAAATACCG TTGGTGGTGA CATTATTAGT GCGGAATTAG GTGCAAATCT CGATATCACT     120

CAATCATTAA ATTTAGGCAC AACGATGGGC TATCAGCGTT ATGACAAATT TAATGAAGGA     180

CGCATTGGTT TCACTGTTAG CCAGCGTTTC TAAGGAGAAA AATA ATG CCG ATA TTT     236
                                              Met Pro Ile Phe
                                                1

CGT TTT ACT GCA CTT GCA ATG ACA TTG GGG CTA TTA TCA GCG CCT TAT      284
Arg Phe Thr Ala Leu Ala Met Thr Leu Gly Leu Leu Ser Ala Pro Tyr
  5              10                  15                  20

AAC GCG ATG GCA GCC ACC AGC AAT CCT GCA TTT GAT CCT AAA AAT CTG      332
Asn Ala Met Ala Ala Thr Ser Asn Pro Ala Phe Asp Pro Lys Asn Leu
             25                  30                  35

ATG CAG TCA GAA ATT TAC CAT TTT GCA CAA AAT AAC CCA TTA GCA GAC      380
Met Gln Ser Glu Ile Tyr His Phe Ala Gln Asn Asn Pro Leu Ala Asp
         40                  45                  50

TTC TCA TCA GAT AAA AAC TCA ATA CTA ACG TTA TCT GAT AAA CGT AGC      428
Phe Ser Ser Asp Lys Asn Ser Ile Leu Thr Leu Ser Asp Lys Arg Ser
     55                  60                  65

ATT ATG GGA AAC CAA TCT CTT TTA TGG AAA TGG AAA GGT GGT AGT AGC      476
Ile Met Gly Asn Gln Ser Leu Leu Trp Lys Trp Lys Gly Gly Ser Ser
 70                  75                  80

TTT ACT TTA CAT AAA AAA CTG ATT GTC CCC ACC GAT AAA GAA GCA TCT      524
Phe Thr Leu His Lys Lys Leu Ile Val Pro Thr Asp Lys Glu Ala Ser
 85                  90                  95                 100

AAA GCA TGG GGA CGC TCA TCT ACC CCC GTT TTC TCA TTT TGG CTT TAC      572
Lys Ala Trp Gly Arg Ser Ser Thr Pro Val Phe Ser Phe Trp Leu Tyr
                105                 110                 115

AAT GAA AAA CCG ATT GAT GGT TAT CCT ACT ATC GAT TTC GGA GAA AAA      620
Asn Glu Lys Pro Ile Asp Gly Tyr Pro Thr Ile Asp Phe Gly Glu Lys
                120                 125                 130

CTC ATT TCA ACC AGT GAG GCT CAG GCA GGC TTT AAA GTA AAA TTA GAT      668
Leu Ile Ser Thr Ser Glu Ala Gln Ala Gly Phe Lys Val Lys Leu Asp
            135                 140                 145

TTC ACT GGC TGG CGT GCT GTG GGA GTC TCT TTA AAT AAC GAT CTT GAA      716
Phe Thr Gly Trp Arg Ala Val Gly Val Ser Leu Asn Asn Asp Leu Glu
150                 155                 160

AAT CGA GAG ATG ACC TTA AAT GCA ACC AAT ACC TCC TCT GAT GGT ACT      764
Asn Arg Glu Met Thr Leu Asn Ala Thr Asn Thr Ser Ser Asp Gly Thr
165                 170                 175                 180

CAA GAC AGC ATT GGG CGT TCT TTA GGT GCT AAA GTC GAT AGT ATT CGT      812
Gln Asp Ser Ile Gly Arg Ser Leu Gly Ala Lys Val Asp Ser Ile Arg
                185                 190                 195

TTT AAA GCG CCT TCT AAT GTG AGT CAG GGT GAA ATC TAT ATC GAC CGT      860
Phe Lys Ala Pro Ser Asn Val Ser Gln Gly Glu Ile Tyr Ile Asp Arg
                200                 205                 210

ATT ATG TTT TCT GTC GAT GAT GCT CGC TAC CAA TGG TCT GAT TAT CAA      908
Ile Met Phe Ser Val Asp Asp Ala Arg Tyr Gln Trp Ser Asp Tyr Gln
            215                 220                 225

GTA AAA ACT CGC TTA TCA GAA CCT GAA ATT CAA TTT CAC AAC GTA AAG      956
```

```
                Val Lys Thr Arg Leu Ser Glu Pro Glu Ile Gln Phe His Asn Val Lys
                    230             235             240

CCA CAA CTA CCT GTA ACA CCT GAA AAT TTA GCG GCC ATT GAT CTT ATT        1004
Pro Gln Leu Pro Val Thr Pro Glu Asn Leu Ala Ala Ile Asp Leu Ile
245             250             255             260

CGC CAA CGT CTA ATT AAT GAA TTT GTC GGA GGT GAA AAA GAG ACA AAC        1052
Arg Gln Arg Leu Ile Asn Glu Phe Val Gly Gly Glu Lys Glu Thr Asn
                265             270             275

CTC GCA TTA GAA GAG AAT ATC AGC AAA TTA AAA AGT GAT TTC GAT GCT        1100
Leu Ala Leu Glu Glu Asn Ile Ser Lys Leu Lys Ser Asp Phe Asp Ala
                280             285             290

CTT AAT ATT CAC ACT TTA GCA AAT GGT GGA ACG CAA GGC AGA CAT CTG        1148
Leu Asn Ile His Thr Leu Ala Asn Gly Gly Thr Gln Gly Arg His Leu
                295             300             305

ATC ACT GAT AAA CAA ATC ATT ATT TAT CAA CCA GAG AAT CTT AAC TCC        1196
Ile Thr Asp Lys Gln Ile Ile Ile Tyr Gln Pro Glu Asn Leu Asn Ser
        310             315             320

CAA GAT AAA CAA CTA TTT GAT AAT TAT GTT ATT TTA GGT AAT TAC ACG        1244
Gln Asp Lys Gln Leu Phe Asp Asn Tyr Val Ile Leu Gly Asn Tyr Thr
325             330             335             340

ACA TTA ATG TTT AAT ATT AGC CGT GCT TAT GTG CTG GAA AAA GAT CCC        1292
Thr Leu Met Phe Asn Ile Ser Arg Ala Tyr Val Leu Glu Lys Asp Pro
                345             350             355

ACA CAA AAG GCG CAA CTA AAG CAG ATG TAC TTA TTA GTG ACA AAG CAT        1340
Thr Gln Lys Ala Gln Leu Lys Gln Met Tyr Leu Leu Val Thr Lys His
                360             365             370

TTA TTA GAT CAA GGC TTT GTT AAA GGG AGT GCT TTA GTG ACA ACC CAT        1388
Leu Leu Asp Gln Gly Phe Val Lys Gly Ser Ala Leu Val Thr Thr His
                375             380             385

CAC TGG GGA TAC AGT TCT CGT TGG TGG TAT ATT TCC ACG TTA TTA ATG        1436
His Trp Gly Tyr Ser Ser Arg Trp Trp Tyr Ile Ser Thr Leu Leu Met
        390             395             400

TCT GAT GCA CTA AAA GAA GCG AAC CTA CAA ACT CAA GTT TAT GAT TCA        1484
Ser Asp Ala Leu Lys Glu Ala Asn Leu Gln Thr Gln Val Tyr Asp Ser
405             410             415             420

TTA CTG TGG TAT TCA CGT GAG TTT AAA AGT AGT TTT GAT ATG AAA GTA        1532
Leu Leu Trp Tyr Ser Arg Glu Phe Lys Ser Ser Phe Asp Met Lys Val
                425             430             435

AGT GCT GAT AGC TCT GAT CTA GAT TAT TTC AAT ACC TTA TCT CGC CAA        1580
Ser Ala Asp Ser Ser Asp Leu Asp Tyr Phe Asn Thr Leu Ser Arg Gln
                440             445             450

CAT TTA GCC TTA TTA TTA CTA GAG CCT GAT GAT CAA AAG CGT ATC AAC        1628
His Leu Ala Leu Leu Leu Glu Pro Asp Asp Gln Lys Arg Ile Asn
                455             460             465

TTA GTT AAT ACT TTC AGC CAT TAT ATC ACT GGC GCA TTA ACG CAA GTG        1676
Leu Val Asn Thr Phe Ser His Tyr Ile Thr Gly Ala Leu Thr Gln Val
        470             475             480

CCA CCG GGT GGT AAA GAT GGT TTA CGC CTG ATG GTA CAG CAT GGC GAC        1724
Pro Pro Gly Gly Lys Asp Gly Leu Arg Leu Met Val Gln His Gly Asp
485             490             495             500

ATG AAG GCA ACT ATC CGG GTT ACT CTT TCC CAG CCT TTA AAA ATG CCT        1772
Met Lys Ala Thr Ile Arg Val Thr Leu Ser Gln Pro Leu Lys Met Pro
                505             510             515

CTC AGC TTA TTT ATT TAT TAC GCG ATA CAC CAT TTC CAG TTG GGT GAA        1820
Leu Ser Leu Phe Ile Tyr Tyr Ala Ile His His Phe Gln Leu Gly Glu
                520             525             530

AGT GGT TGG AAT AAC CTG AAA AAA GCG ATG GTT TCA GCG TGG ATC TAC        1868
Ser Gly Trp Asn Asn Leu Lys Lys Ala Met Val Ser Ala Trp Ile Tyr
                535             540             545
```

```
                                                      -continued

AGT AAT CCA GAA GTT GGA TTA CCG CTT GCA GGA AGA CAC CCT TTT AAC        1916
Ser Asn Pro Glu Val Gly Leu Pro Leu Ala Gly Arg His Pro Phe Asn
    550             555                 560

TCA CCT TCG TTA AAA TCA GTC GCT CAA GGC TAT TAC TGG CTT GCC ATG        1964
Ser Pro Ser Leu Lys Ser Val Ala Gln Gly Tyr Tyr Trp Leu Ala Met
565             570                 575                 580

TCT GCA AAA TCA TCG CCT GAT AAA ACA CTT GCA TCT ATT TAT CTT GCG        2012
Ser Ala Lys Ser Ser Pro Asp Lys Thr Leu Ala Ser Ile Tyr Leu Ala
                585                 590                 595

ATT AGT GAT AAA ACA CAA AAT GAA TCA ACT GCT ATT TTT GGA GAA ACT        2060
Ile Ser Asp Lys Thr Gln Asn Glu Ser Thr Ala Ile Phe Gly Glu Thr
                    600                 605                 610

ATT ACA CCA GCG TCT TTA CCT CAA GGT TTC TAT GCC TTT AAT GGC GGT        2108
Ile Thr Pro Ala Ser Leu Pro Gln Gly Phe Tyr Ala Phe Asn Gly Gly
                615                 620                 625

GCT TTT GGT ATT CAT CGT TGG CAA GAT AAA ATG GTG ACA CTG AAA GCT        2156
Ala Phe Gly Ile His Arg Trp Gln Asp Lys Met Val Thr Leu Lys Ala
630             635                 640

TAT AAC ACC AAT GTT TGG TCA TCT GAA ATT TAT AAC AAA GAT AAC CGT        2204
Tyr Asn Thr Asn Val Trp Ser Ser Glu Ile Tyr Asn Lys Asp Asn Arg
645                 650                 655                 660

TAT GGC CGT TAC CAA AGT CAT GGT GTC GGT CAA ATA GTG AGT AAT GGC        2252
Tyr Gly Arg Tyr Gln Ser His Gly Val Gly Gln Ile Val Ser Asn Gly
                    665                 670                 675

TCG CAG CTT TCA CAG GGC TAT CAG CAA GAA GGT TGG GAT TGG AAT AGA        2300
Ser Gln Leu Ser Gln Gly Tyr Gln Gln Glu Gly Trp Asp Trp Asn Arg
                680                 685                 690

ATG CAA GGG GCA ACC ACT ATT CAC CTT CCT CTT AAA GAC TTA GAC AGT        2348
Met Gln Gly Ala Thr Thr Ile His Leu Pro Leu Lys Asp Leu Asp Ser
                    695                 700                 705

CCT AAA CCT CAT ACC TTA ATG CAA CGT GGA GAG CGT GGA TTT AGC GGA        2396
Pro Lys Pro His Thr Leu Met Gln Arg Gly Glu Arg Gly Phe Ser Gly
    710                 715                 720

ACA TCA TCC CTT GAA GGT CAA TAT GGC ATG ATG GCA TTC GAT CTT ATT        2444
Thr Ser Ser Leu Glu Gly Gln Tyr Gly Met Met Ala Phe Asp Leu Ile
725                 730                 735                 740

TAT CCC GCC AAT CTT GAG CGT TTT GAT CCT AAT TTC ACT GCG AAA AAG        2492
Tyr Pro Ala Asn Leu Glu Arg Phe Asp Pro Asn Phe Thr Ala Lys Lys
                745                 750                 755

AGT GTA TTA GCC GCT GAT AAT CAC TTA ATT TTT ATT GGT AGC AAT ATA        2540
Ser Val Leu Ala Ala Asp Asn His Leu Ile Phe Ile Gly Ser Asn Ile
                    760                 765                 770

AAT AGT AGT GAT AAA AAT AAA AAT GTT GAA ACG ACC TTA TTC CAA CAT        2588
Asn Ser Ser Asp Lys Asn Lys Asn Val Glu Thr Thr Leu Phe Gln His
                775                 780                 785

GCC ATT ACT CCA ACA TTA AAT ACC CTT TGG ATT AAT GGA CAA AAG ATA        2636
Ala Ile Thr Pro Thr Leu Asn Thr Leu Trp Ile Asn Gly Gln Lys Ile
    790                 795                 800

GAA AAC ATG CCT TAT CAA ACA ACA CTT CAA CAA GGT GAT TGG TTA ATT        2684
Glu Asn Met Pro Tyr Gln Thr Thr Leu Gln Gln Gly Asp Trp Leu Ile
805             810                 815                 820

GAT AGC AAT GGC AAT GGT TAC TTA ATT ACT CAA GCA GAA AAA GTA AAT        2732
Asp Ser Asn Gly Asn Gly Tyr Leu Ile Thr Gln Ala Glu Lys Val Asn
                825                 830                 835

GTA AGT CGC CAA CAT CAG GTT TCA GCG GAA AAT AAA AAT CGC CAA CCG        2780
Val Ser Arg Gln His Gln Val Ser Ala Glu Asn Lys Asn Arg Gln Pro
                    840                 845                 850

ACA GAA GGA AAC TTT AGC TCG GCA TGG ATC GAT CAC AGG ACT CGC CCC        2828
Thr Glu Gly Asn Phe Ser Ser Ala Trp Ile Asp His Arg Thr Arg Pro
                855                 860                 865
```

```
AAA GAT GCC AGT TAT GAG TAT ATG GTC TTT TTA GAT GCG ACA CCT GAA      2876
Lys Asp Ala Ser Tyr Glu Tyr Met Val Phe Leu Asp Ala Thr Pro Glu
        870                 875                 880

AAA ATG GGA GAG ATG GCA CAA AAA TTC CGT GAA AAT AAT GGG TTA TAT      2924
Lys Met Gly Glu Met Ala Gln Lys Phe Arg Glu Asn Asn Gly Leu Tyr
885                 890                 895                 900

CAG GTT CTT CGT AAG GAT AAA GAC GTT CAT ATT ATT CTC GAT AAA CTC      2972
Gln Val Leu Arg Lys Asp Lys Asp Val His Ile Ile Leu Asp Lys Leu
                905                 910                 915

AGC AAT GTA ACG GGA TAT GCC TTT TAT CAG CCA GCA TCA ATT GAA GAC      3020
Ser Asn Val Thr Gly Tyr Ala Phe Tyr Gln Pro Ala Ser Ile Glu Asp
            920                 925                 930

AAA TGG ATC AAA AAG GTT AAT AAA CCT GCA ATT GTG ATG ACT CAT CGA      3068
Lys Trp Ile Lys Lys Val Asn Lys Pro Ala Ile Val Met Thr His Arg
                935                 940                 945

CAA AAA GAC ACT CTT ATT GTC AGT GCA GTT ACA CCT GAT TTA AAT ATG      3116
Gln Lys Asp Thr Leu Ile Val Ser Ala Val Thr Pro Asp Leu Asn Met
    950                 955                 960

ACT CGC CAA AAA GCA GCA ACT CCT GTC ACC ATC AAT GTC ACG ATT AAT      3164
Thr Arg Gln Lys Ala Ala Thr Pro Val Thr Ile Asn Val Thr Ile Asn
965                 970                 975                 980

GGC AAA TGG CAA TCT GCT GAT AAA AAT AGT GAA GTG AAA TAT CAG GTT      3212
Gly Lys Trp Gln Ser Ala Asp Lys Asn Ser Glu Val Lys Tyr Gln Val
                985                 990                 995

TCT GGT GAT AAC ACT GAA CTG ACG TTT ACG AGT TAC TTT GGT ATT CCA      3260
Ser Gly Asp Asn Thr Glu Leu Thr Phe Thr Ser Tyr Phe Gly Ile Pro
                1000                1005                1010

CAA GAA ATC AAA CTC TCG CCA CTC CCT TGATTTAATC AAAAGGAACC            3307
Gln Glu Ile Lys Leu Ser Pro Leu Pro
                1015            1020

TCTTGCGTTC CTTTTTTATT TGCAGGAAAT CTGATTATGC TAATAAAAAA CCCTTTAGCC    3367

CAGGCGGTTA CATTAAGCCT CTGTTTATCA TTACCCGCAC AAGCATTACC CACTCTGTCT    3427

CATGAAGCTT TCGGCGTATT TATCTTTTGA AGGTGAATTA CCCAATACCT TACCACTTC     3486

(2) INFORMATION FOR SEQ ID NO:2:

(i) SEQUENCE CHARACTERISTICS:
        (A) LENGTH: 1021 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Ile Phe Arg Phe Thr Ala Leu Ala Met Thr Leu Gly Leu Leu
1               5                   10                  15

Ser Ala Pro Tyr Asn Ala Met Ala Thr Ser Asn Pro Ala Phe Asp
            20                  25                  30

Pro Lys Asn Leu Met Gln Ser Glu Ile Tyr His Phe Ala Gln Asn Asn
            35                  40                  45

Pro Leu Ala Asp Phe Ser Ser Asp Lys Asn Ser Ile Leu Thr Leu Ser
        50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110
```

```
Phe Trp Leu Tyr Asn Glu Lys Pro Ile Asp Gly Tyr Pro Thr Ile Asp
        115                 120                 125
Phe Gly Glu Lys Leu Ile Ser Thr Ser Glu Ala Gln Ala Gly Phe Lys
        130                 135                 140
Val Lys Leu Asp Phe Thr Gly Trp Arg Ala Val Gly Val Ser Leu Asn
145                 150                 155                 160
Asn Asp Leu Glu Asn Arg Glu Met Thr Leu Asn Ala Thr Asn Thr Ser
                165                 170                 175
Ser Asp Gly Thr Gln Asp Ser Ile Gly Arg Ser Leu Gly Ala Lys Val
            180                 185                 190
Asp Ser Ile Arg Phe Lys Ala Pro Ser Asn Val Ser Gln Gly Glu Ile
            195                 200                 205
Tyr Ile Asp Arg Ile Met Phe Ser Val Asp Asp Ala Arg Tyr Gln Trp
            210                 215                 220
Ser Asp Tyr Gln Val Lys Thr Arg Leu Ser Glu Pro Glu Ile Gln Phe
225                 230                 235                 240
His Asn Val Lys Pro Gln Leu Pro Val Thr Pro Glu Asn Leu Ala Ala
                245                 250                 255
Ile Asp Leu Ile Arg Gln Arg Leu Ile Asn Glu Phe Val Gly Gly Glu
            260                 265                 270
Lys Glu Thr Asn Leu Ala Leu Glu Glu Asn Ile Ser Lys Leu Lys Ser
            275                 280                 285
Asp Phe Asp Ala Leu Asn Ile His Thr Leu Ala Asn Gly Gly Thr Gln
        290                 295                 300
Gly Arg His Leu Ile Thr Asp Lys Gln Ile Ile Ile Tyr Gln Pro Glu
305                 310                 315                 320
Asn Leu Asn Ser Gln Asp Lys Gln Leu Phe Asp Asn Tyr Val Ile Leu
                325                 330                 335
Gly Asn Tyr Thr Thr Leu Met Phe Asn Ile Ser Arg Ala Tyr Val Leu
            340                 345                 350
Glu Lys Asp Pro Thr Gln Lys Ala Gln Leu Lys Gln Met Tyr Leu Leu
            355                 360                 365
Val Thr Lys His Leu Leu Asp Gln Gly Phe Val Lys Gly Ser Ala Leu
        370                 375                 380
Val Thr Thr His His Trp Gly Tyr Ser Ser Arg Trp Trp Tyr Ile Ser
385                 390                 395                 400
Thr Leu Leu Met Ser Asp Ala Leu Lys Glu Ala Asn Leu Gln Thr Gln
                405                 410                 415
Val Tyr Asp Ser Leu Leu Trp Tyr Ser Arg Glu Phe Lys Ser Ser Phe
            420                 425                 430
Asp Met Lys Val Ser Ala Asp Ser Ser Asp Leu Asp Tyr Phe Asn Thr
            435                 440                 445
Leu Ser Arg Gln His Leu Ala Leu Leu Leu Glu Pro Asp Asp Gln
        450                 455                 460
Lys Arg Ile Asn Leu Val Asn Thr Phe Ser His Tyr Ile Thr Gly Ala
465                 470                 475                 480
Leu Thr Gln Val Pro Pro Gly Gly Lys Asp Gly Leu Arg Leu Met Val
                485                 490                 495
Gln His Gly Asp Met Lys Ala Thr Ile Arg Val Thr Leu Ser Gln Pro
            500                 505                 510
Leu Lys Met Pro Leu Ser Leu Phe Ile Tyr Tyr Ala Ile His His Phe
            515                 520                 525
```

```
Gln Leu Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
                565                 570                 575

Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
        595                 600                 605

Phe Gly Glu Thr Ile Thr Pro Ala Ser Leu Pro Gln Gly Phe Tyr Ala
    610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Gly Gln Ile
                660                 665                 670

Val Ser Asn Gly Ser Gln Leu Ser Gln Gly Tyr Gln Gln Glu Gly Trp
        675                 680                 685

Asp Trp Asn Arg Met Gln Gly Ala Thr Thr Ile His Leu Pro Leu Lys
    690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asp Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
        755                 760                 765

Gly Ser Asn Ile Asn Ser Ser Asp Lys Asn Lys Asn Val Glu Thr Thr
    770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
        835                 840                 845

Asn Arg Gln Pro Thr Glu Gly Asn Phe Ser Ser Ala Trp Ile Asp His
    850                 855                 860

Arg Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
        915                 920                 925

Ser Ile Glu Asp Lys Trp Ile Lys Lys Val Asn Lys Pro Ala Ile Val
    930                 935                 940

Met Thr His Arg Gln Lys Asp Thr Leu Ile Val Ser Ala Val Thr Pro
```

```
                       945                  950                  955                  960
Asp Leu Asn Met Thr Arg Gln Lys Ala Ala Thr Pro Val Thr Ile Asn
                965                  970                  975
Val Thr Ile Asn Gly Lys Trp Gln Ser Ala Asp Lys Asn Ser Glu Val
            980                  985                  990
Lys Tyr Gln Val Ser Gly Asp Asn Thr Glu Leu Thr Phe Thr Ser Tyr
        995                 1000                 1005
Phe Gly Ile Pro Gln Glu Ile Lys Leu Ser Pro Leu Pro
       1010                 1015                 1020
```

(2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Ala Thr Ala Asn Pro Ala Phe Asp Pro Lys Asn Leu Met Gln Ser Glu
 1               5                  10                  15
Ile Tyr
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTAATGGGTT ATTTTGTGCA A                                                 21

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GCNACNUCNA AYCCNGC                                                     17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCNACNAGYA AYCCNGC                                                     17

(2) INFORMATION FOR SEQ ID NO:7:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:7:

UACGUYAGNC UYUADAU  17

(2) INFORMATION FOR SEQ ID NO:8:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:8:

UACGUYUCRC UYUADAU  17

(2) INFORMATION FOR SEQ ID NO:9:

(i) SEQUENCE CHARACTERISTICS:
  (A) LENGTH: 25 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:9:

CATTTGATCC TAAAAATCTG ATGCA  25

(2) INFORMATION FOR SEQ ID NO:10:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:10:

GCAACCAGCA ATCCTGCA  18

(2) INFORMATION FOR SEQ ID NO:11:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:11:

GACTACGTCA GGCTTTTAAT  20

(2) INFORMATION FOR SEQ ID NO:12:

(i) SEQUENCE CHARACTERISTICS:
  (A) LENGTH: 53 base pairs (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

GCAACCAGCA ATCCTGCATT TGATCCTAAA AATCTGATGC AGTCCGAAAT TTA            53

(2) INFORMATION FOR SEQ ID NO:13:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

TAATTTTCGG ACTGCATCAG ATTTTTAGGA TCAAATGCAG GATTGCTGGT TGC            53

(2) INFORMATION FOR SEQ ID NO:14:

(i) SEQUENCE CHARACTERISTICS:
            (A) LENGTH: 122 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

GATATCACTC AATCATTAAA TTTAGGCACA ACGATGGGCT ATCAGCGTTA TGACAAATTT     60

AATGAAGGAC GCATTGGTTT CACTGTTAGC CAGCGTTTCT AAGGAGAAAA ATAATGCCGA    120

TA                                                                  122

(2) INFORMATION FOR SEQ ID NO:15:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

ATGACAAATT TAATGAAGGA CGCATTGGTT TCACTGTTAG CCAGCGTTTC TAAGGAGAAA     60

(2) INFORMATION FOR SEQ ID NO:16:

(i) SEQUENCE CHARACTERISTICS:
            (A) LENGTH: 400 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 296..400

(xi) SEQUENCE DESCRIPTION: SEQ ID NO:16:

CAGACTGCTT ATGGCAAATT AACCCCCTCT CTTAATCTTC GTTATTCAAA GATATTGCAG     60

GTGACAATGA TATCAATCAA CGCCACAGCC TTACCTATTT TAATACAGGG GGAAGTACCT    120

```
TTGATATTAA AGGAAATACC GTTGGTGGTG ACATTATTAG TGCGGAATTA GGTGCAAATC              180

TCGATATCAC TCAATCATTA AATTTAGGCA CAACGATGGG CTATCAGCGT TATGACAAAT              240

TTAATGAAGG ACGCATTGGT TTCACTGTTA GCCAGCGTTT CTAAGGAGAA AAATA ATG              298
                                                               Met
                                                                1

CCA ATA TTT CGT TTT ACT GCA CTT GCA ATG ACA TTG GGG CTA TTA TCA                346
Pro Ile Phe Arg Phe Thr Ala Leu Ala Met Thr Leu Gly Leu Leu Ser
         5                   10                  15

GCG CCT TAT AAC GCG ATG GCA GCC ACC AGC AAT CCT GCA TTT GAT GCT                394
Ala Pro Tyr Asn Ala Met Ala Ala Thr Ser Asn Pro Ala Phe Asp Ala
         20                  25                  30

AAA AAT                                                                        400
Lys Asn
    35

(2) INFORMATION FOR SEQ ID NO:17:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:17:

Met Pro Ile Phe Arg Phe Thr Ala Leu Ala Met Thr Leu Gly Leu Leu
 1               5                  10                  15

Ser Ala Pro Tyr Asn Ala Met Ala Ala Thr Ser Asn Pro Ala Phe Asp
             20                  25                  30

Ala Lys Asn
        35
```

METHODS FOR IDENTIFYING AND ISOLATING ANTIGEN-SPECIFIC T CELLS

RELATED APPLICATIONS

This application claims priority to provisional application No. 60/105,018, filed Oct. 20, 1998.

GOVERNMENT SUPPORT

This invention was made with government support under NIH Grant Nos. AR40770, AI37232, and AR41897. The government has certain rights in this invention.

FIELD

The field of this invention is immunology, specifically, methods of preparing artificial antigen presenting cells and their application to methods of isolating antigen-specific T cells, methods of modulating the T cell response and methods of treating conditions which would benefit from the modulation of the T cell response, for example, transplantation therapy, autoimmune disorders, allergies, cancers and viral and bacterial infections.

BACKGROUND

The following description provides a summary of information relevant to the present invention. It is not an admission that any of the information provided herein is prior art to the presently claimed invention, nor that any of the publications specifically or implicitly referenced are prior art to the invention.

The immunologic arts have advanced markedly over the past ten years. The complexity of the science explaining aspects of the field is immense. We set forth below in this section a discussion concerning known aspects of various elements involved in immunogenic responses and concepts in the art that are related to the invention disclosed herein.

T Cells

T lymphocytes (i.e., T cells) are part of the immune system, which defends the body against bacterial, viral and protozoal infection, as well as aberrant molecules that contain epitopes recognized as non-self. The recognition of non-self molecules as well as the destruction of infectious agents carrying non-self antigens is a function of T cells. These cells provide for the cell-mediated immune responses of adaptive immunity.

Infecting pathogens are generally accessible to extracellular antibodies found in the blood and the extracellular spaces. However, some infecting agents, and all viruses, replicate inside cells where they are not exposed to, and cannot be detected by, extracellular antibodies. In order for these foreign agents to be accessible to the cell-mediated immune response, the cells harboring such pathogens must either "express" antigenic motifs of the infecting agents on the surface of the cells or the antigenic motifs must be shed from-the-cells, e.g. by cell death, to be accessible to and subsequently expressed on the cell membrane of phagocytic antigen presenting cells ("APCs") that participate in the immune process.

Antigens derived from replicating virus for example, are displayed on the surface of infected cells where they may be recognized by "cytotoxic" T cells which may then control the infection by recognizing the viral antigen and killing the cell. The actions of such cytotoxic T cells depends upon direct interaction between the antigenic motif of the infecting agent expressed on the surface of the infected cells and the T cell's receptors having a specificity for the motif.

Although T cells are important in the control of intracellular infections, some foreign agents evade such control because they replicate only in the vesicles of macrophages; an important example is *Mycobacterium tuberculosis*, the pathogen that causes tuberculosis. Whereas bacteria entering macrophages are usually destroyed in the lysosomes, which contain a variety of enzymes and bactericidal substances, infectious agents such as *M. tuberculosis*, survive because the vesicles they occupy cannot fuse with the lysosomes. The immune system provides for fighting such agents by a second type of T cell, known as a T helper cell, which helps to activate macrophages and induce the fusion of lysosomes with the vesicles containing the infecting agents. The helper cells also bring about the stimulation of other immune mechanisms of the phagocyte. T helper cells may further be involved in initiating and/or sustaining the immune system's release of soluble factors that attract macrophages and other professional APCs to the site of infection.

Additionally, specialized "helper" T cells play a central part in the destruction of extracellular pathogens by interacting with B cells. Depending on the type of infection being controlled, participating T helper cells may have an inflammatory or Th1-like phenotype, or a suppressive Th2-like phenotype.

T Cell Receptors

T cell receptors (TCRs) are closely related to antibody molecules in structure and are involved in antigen binding. Variability in the antigen binding site of the TCR is created in a fashion similar to antibodies in that a large capacity for diversity is available. The diversity is found in the CDR3 loops of TCR variable regions which are found in the center of the antigen-binding site of the TCR. The diversity that is obtainable by TCRs for specific antigens is also directly related to an MHC molecule on the APC's surface to which the antigenic motif is bound and presented to the TCR.

One type of MHC that is involved in presenting processed antigen is class II MHC. The antigen or peptide binding site for a peptide on a class II MHC molecule lies in a cleft between the alpha and beta chain helices of the MHC molecule. In another type of MHC, the class I MHC, the binding site for a peptide lies in a cleft between the two alpha helices of the alpha chain. From the arrangement of highly variable antigens complexing with MHC molecule alleles, it is understandable that the mechanism of TCR recognition involves a combined distribution of variability in the TCR which must correlate with a distribution of variability in the ligand (i.e., antigen/MHC molecule complex). (Garboczi, et al., *Nature* Vol. 384; 134–41; Ward and Quadri, *Curr Op Immunol.* Vol. 9:97–106; Garcia, et al., *Science*, Vol. 279: 1166–72).

MHC Molecules

In general, T cell responses to non-self motifs depend on the interactions of the T cells with other cells containing proteins recognized as non-self. In the case of cytotoxic T cells and Th1 cells, non-self proteins (i.e. antigens) are recognized on the surface of the target cell (such as an infected cell). Th2 cells, on the other hand, recognize and interact with antigen presented by professional antigen presenting cells such as dendritic cells, and B cells. Dendritic cells non-specifically internalize antigen while B cells bind and internalize foreign antigens via their surface immunoglobulin. In any case, T cells recognize their targets by detecting non-self antigenic motifs (e.g., peptide fragments derived from for example, a bacterium or virus) that are expressed either on infected cells or other immune cells, e.g.

phagocytic APC. The molecules that associate with these peptide or antigen fragments and present them to T cells are membrane glycoproteins encoded by a cluster of genes bearing the cumbersome name "major histocompatibility complex" (MHC). These glycoproteins were first identified in mice in studies examining the effects on the immune response to transplanted tissues. In humans, the MHC equivalent has been termed HLA for "human leukocyte antigen". In general, the term MHC is used to describe generally the molecules in the mammalian immune system involved in the presentation of antigenic motifs to T cells. As used specifically in this Letters Patent, MHC means any major histocompatibility complex molecule, either class I or class II, from any mammalian organism including a human, such molecule comprising full-length MHC molecules or sub-units thereof further comprising MHC encoded antigen-presenting glycoproteins having the capacity to bind a peptide representing a fragment of an autoantigen or other non-antigenic or antigenic sequence (e.g., a peptide), said MHC further having an amino acid sequence that is expressed and purified from natural sources, or by any artificial means in prokaryotic or eukaryotic systems having different glycosilations, or of either natural or synthetic origin that contains or comprises a modification of a natural MHC sequence.

The actions of T cells depend on their ability to recognize antigenic motifs on cells (such as cells harboring pathogens or that have internalized pathogen-derived products). T cells recognize peptide fragments (e.g., pathogen-derived proteins) in the form of complexes between such peptides and MHC molecules that are expressed on the surface of "antigen presenting cells".

The two types of MHC molecules, i.e., MHC class I and MHC class II, deliver peptides from different sources (class I being intracellular, and class II being extracellular) to the surface of the infected cell. The two classes of MHC molecules vary with respect to the length of peptides that they are able to present. The binding pocket of the MHC class I molecules is blocked at either end, thereby imposing severe restrictions on the size of peptides it can accommodate (8–10 residues). The binding groove of the MHC class II molecules on the other hand allows peptides to protrude from the ends, and consequently much longer peptides (8–30 residues) can bind. (Rudensky, et al. *Nature*, Vol. 353:622–27; Miyazaki, et al., *Cell*, Vol. 84:531–41; Zhong, et al., *J. Exp. Med.*, Vol. 284:2061–66).

Antigen Processing

Peptides bound to MHC class I molecules are recognized by CD8+ T cells (cytotoxic T cells), and those bound to MHC class II molecules are recognized by CD4+ T cells (helper T cells). Two functional subsets of T cells are thereby activated to initiate the destruction of antigenic motifs, and thereby the source (e.g. a pathogen) which may reside in different cellular compartments. CD4+ T cells may also help to activate B cells that have internalized specific antigen, and in turn give rise to the stimulation of antibody production against the antigenic motifs of the extracellular pathogens.

Infectious or antigenic agents can reside in either of two distinct intracellular compartments. Viruses and certain bacteria replicate in the cytosol or in the contiguous nuclear compartment, while many pathogenic bacteria and some eukaryotic parasites replicate in the endosomes and lysosomes that form part of the vesicular system. The immune system has different strategies for eliminating such agents from these two sites. Cells containing viruses or bacteria located in the cytosol are eliminated by cytotoxic T cells which express the cell-surface molecule CD8. The function of CD8 T cells is to kill infected cells.

Immunogenic agents located in the vesicular compartments of cells (which may or may not have been involved in the internalization of extracellular matter) are detected by a different class of T cell, distinguished by surface expression of the molecule CD4. CD4 T cells are specialized to activate/ modulate other cells and fall into two functional classes: Th1 cells which activate various immune competent cells to have the intravesicular non-self antigenic agents they harbor destroyed, and Th2 cells which help to activate B cells to, among other things, make antibody against such foreign agents.

To produce an appropriate response to infectious microorganisms, T cells need to be able to distinguish between self and foreign or non-self material coming from the different processing pathways. This is achieved through delivery of peptides to the cell surface from each of these intracellular compartments by the different classes of MHC molecules. As noted above, MHC class I molecules deliver peptides originating in the cytosol to the cell surface, where the antigen (i.e., non-self recognized peptide) is expressed in association with the MHC molecules (antigen:MHC complex) and is recognized by CD8 T cells. Likewise, MHC class II molecules deliver the non-self peptides originating from extracellular sources to the cell surface, where they are recognized by CD4 T cells.

Antigen Presenting Cells

When naïve T cells encounter for the first time a specific antigen on the surface of an antigen-presenting cell (APC), they are activated to proliferate and differentiate into cells capable of contributing to the removal of the antigen and its source (e.g. an infecting pathogen). The APCs are specialized in that they express surface molecules that synergize with a specific antigen in the activation of naïve T cells. APCs become concentrated in the peripheral lymphoid organs, to which they migrate after trapping antigen while circulating in the periphery. APCs present peptide fragments or antigenic motifs to recirculating naïve T cells. Arguably, the most important APCs are dendritic cells whose known function includes the presentation of antigen to Macrophages and are important in phagocytosis of cells that provide a first line of defense against infecting agents. APCs are also known to be activated by armed effector T cells. B cells also serve as APCs under some circumstances.

One of the features of APCs is the expression of co-stimulatory molecules including B7-1 and B7-2 molecules. Naïve T cells will respond to an antigenic motif only when the same APC presents to the T cell both the specific motif recognized by the TCR and a B7 molecule which is recognized by CD28 or CTLA-4, the receptors for B7 existing on the T cell surface. (Anderson, et al., *J. Immunol.*, Vol. 159:4:1669–75). The activation of T cells by APCs leads to proliferation of the activated T cells and to the differentiation of their progeny into armed effector T cells. The proliferation and differentiation of T cells depends on the production of cytokines (such as the T cell growth factor, IL-2) and their binding to high-affinity receptors on the activated T cell. T cells whose TCRs are bound to antigens in the absence of co-stimulatory molecules fail to make cytokines and instead become anergic. This dual requirement for both receptor/ antigenic interaction and co-stimulation helps to further mediate naïve T cell response.

Proliferating T cells develop into armed effector T cells, the critical event in most adaptive immune response. Once an expanded clone of T cells achieves effector function, the T cell clone progeny can act on any target cell that displays or expresses a specific antigen on its surface. Effector T cells can mediate a variety of functions. The killing of infected cells by CD8 cytotoxic T cells and the activation of professional APC by Th1 cells together make up cell-mediated immunity. The activation of B cells by both Th2 and Th1 cells help to produce different types of antibodies, thus driving the humoral immune response. (Kirberg, et al., *J. Exp. Med.*, Vol. 186:8:1269–75).

T Cell Activation

T cells generally become sensitized to antigens by becoming trapped in lymphoid organs as the T cells drain into lymph nodes through which they circulate. Antigens introduced directly into the bloodstream, or that reach the bloodstream from an infected lymph node, are picked up by APCs in the spleen for example where lymphoid cell sensitization occurs in the splenic white pulp. The trapping of antigen by APCs that migrate to these lymphoid tissues combined with the continuous recirculation of T cells through the tissues ensures that rare antigen-specific T cells will encounter their specific antigen being presented by an APC.

The recirculation of naïve T cells through the lymphoid organs is orchestrated by adhesive interactions between lymphocytes and endothelial cells. Naïve T cells enter the lymphoid organs through a process which is thought to occur in a number of steps. The first step in this process is mediated by selectins expressed on the T cell. For example, L-selectin on naïve T cells binds to sulfated carbohydrates on the vascular addressins GlyCAM-1 and CD34. CD34 is expressed on endothelial cells in many tissues but is properly glycosylated for L-selectin binding only on the high endothelial venule cells of lymph nodes. L-selectin binding promotes a rolling interaction, which is critical to the selectivity of naïve lymphocyte homing. Although this interaction is too weak to promote extravasation, it is essential for the initiation of the stronger interactions that then follow between the T cell and the high endothelium, which are mediated by molecules with a relatively broad tissue distribution. (Finger, et al., *Nature*, Vol. 379:266–9).

Stimulation by locally bound chemokines activates the adhesion molecule LFA-1 on the T cell, increasing its affinity for ICAM-2, which is expressed constitutively on all endothelial cells, and ICAM-1, which, in the absence of inflammation, is expressed only on the high endothelial venule cells of peripheral lymphoid tissues. The binding of LFA-1 to 4ts4igands, ICAM-1 and ICAM-2 plays a major role in T cell adhesion to and migration through the wall of the blood vessel into the lymph nodes. Bachmann et al., *Immunity*, Vol. 7:549–57).

The high endothelial venules are located in the lymph nodes. This area is inhabited by dendritic cells, which have recently migrated from the periphery. The migrating T cells scan the surface of these APCs for specific antigen:MHC complexes. If they do not recognize antigen presented by these cells, they eventually leave the node via an efferent lymphatic vessel, which returns them to the blood so that they can recirculate through other lymph nodes. Rarely, a naïve T cell recognizes its specific antigen:MHC complex on the surface of an APC, which then signals the activation of LFA-1, causing the T cell to adhere strongly to the APC. Binding to the antigen:MHC complex also activates the cell to proliferate and differentiate, resulting in the production of armed, antigen-specific T cells. The number of T cells that interact with each APC in lymph nodes is very high, as can be seen by the rapid trapping of antigen-specific T cells in a single lymph node containing antigen.

Identification and Isolation of Antigen-Specific T Cells

As noted above, T cells represent a major component of the body's immune defenses against bacterial, viral and protozoal infections, as well as non-self antigenic motifs from other sources. T cells have also been implicated in the rejection of cancerous cells. Autoimmune disorders have also been linked to antigen-specific T cell attack against various parts of the body. One of the major problems hampering the understanding of and intervention on the mechanisms involved in these disorders is the difficulty in identifying T cells specific for the antigen to be studied. Accordingly, it is of great interest to be able to identify antigen-specific T cells. Additionally, it would be of great therapeutic benefit if T cells specific for a particular antigen could be (i) enriched and then reintroduced in a disease situation, (ii) selectively depleted in the case of an autoimmune disorder, or (iii) modified to alter their functional and/or phenotypic characteristics. Thus, identification and isolation of antigen specific T cells is an essential requirement in immunology and medicine to understand and modulate immune responses.

Identification of antigen-specific T cell populations is generally accomplished by indirect means in animal models, such as by evaluating membrane markers correlated to activation or maturation of these cells. The majority of these studies were performed in transgenic systems (Ignatowicz, et al., *Cell*, 84:521–29; Sebzda et al., *Science*, Vol. 263: 1615–18; Jameson et al., *Ann. Rev. Immunol.*, Vol. 13:93–126). Analysis is generally done by means of flow cytometry, where a detector on a machine is capable of identifying cells bound to fluorescent substrates, such as fluorescent antibodies. Positively identified cells can be sorted for further use. Quantitation and isolation of antigen-specific T cells is usually accomplished by limiting dilution and cloning techniques. When using sorted cells, these approaches become quite cumbersome and are sometimes inaccurate, since the biological effects of antigen recognition can spread beyond the cells recognizing the antigen. For instance, upon engagement of the specific MHC:antigenic peptide complex, T cells produce cytokines that can affect expression of the same markers of activation in non-specific bystander T cells. Hence, in order to isolate and characterize cells with specificity for a given antigen, alternative procedures, such as T cell cloning, need to be applied. These techniques often require many months of technical procedures before results can be obtained. The rate of success, in particular for human systems, is quite low, and the population selected may not necessarily represent the biologically relevant component of the immune response to a given peptide. The direct interaction of a specific T cell with the antigen:MHC complex would thus be a preferred basis for T cell isolation.

Theory of the Invention

The immunoregulation art has advanced steadily in recent years. The scientific literature contains many studies showing interactions and modulation effects between specific molecules and cell types. However, no discovery has been presented that is able to apply the knowledge that has been gained by the extensive research in the field toward a method or device that can be used in a comprehensive package for carrying out the identification, isolation, and modulation of immunoregulatory cells for the purpose of advancing the ultimate goal of such knowledge, i.e. improved treatment regimens for various states of disease.

We have discovered a platform technology for advancing treatment regimens requiring the immunoregulation of immune cells that centers around the use of an artificial antigen presenting cell (APC). This platform technology may be designed or programmed on demand for use in the treatment of a broad spectrum of specific disease states. Moreover, this system is versatile and applicable to all situations where the isolation, identification, and modulation of T cells is of clinical import. We have recognized the relevance of several types of molecular entities to the stimulation/activation and modulation response of T cells in their role within the immune system and have incorporated these entities into artificial APCs. We use such artificial APCs to capture and manipulate antigen specific T cells.

Historically, programming and using T cells therapeutically has been hampered by the problem of finding a means by which the cells can be handled for such manipulation and observation of the effectiveness of the manipulation applied. We have solved this problem by adopting the theory that a T cell can best be manipulated by using APC like structures and encorporating into such structures molecules constructed to (1) bind the "artificial" APC to specific T cell types, (2) stimulate or modulate only specifically bound T cells for any desired response, and (3) bind the artificial APC to a solid support in situations where anchoring the APC to a specific location is desired.

Prior to our invention, no comprehensive system has been disclosed, nor was it obvious that such a system would function as desired, to achieve a platform that is universally applicable to activating and modulation T cells. As can be seen by the numerous following distinctions, much of the art has centered only on basic research relating to molecules and their association with T cell response.

Distinctions

Kendrick et al., U.S. Pat. No. 5,595,881 (the '881 disclosure) discuss a method for the detection and isolation of MHC:antigen-restricted T cells which is performed by preparing the MHC:antigen complex, which complex is isolated by using metal chelating technology. The complexes then bound to a planar solid support {i.e., a glass coverslip), followed in turn by combining the immobilized complex with a biological sample so that the MHC:antigen complex may bind to and retain antigen-specific T cells. Determination of the presence of reactive MHC:antigen complexes is carried out by observation of cell proliferation.

The method described in the '881 disclosure differs from the current invention in a number of substantial structural and functional ways. First, the MHC component of the complexes in the '881 disclosure are immobilized on a solid support. The MHC component of the current invention is not bound to a solid support but is freely "floating" within the bilayer of a polysome membrane comprising a phosphotidylcholine and cholesterol component. The difference is substantial in that the MHC:antigen complex of the '881 disclosure is not able to participate in the migration or concentration of such complexes in "capping" which is important to improved binding and activation of bound T cells. Second, the '881 method is only directed to the detection of the presence of "natural" APCs that are specific for pre-selected antigen-specific T cells after such T cells have been isolated. The isolation of antigen-specific T cells is carried out by first performing a series of steps including binding antigen via a metal chelating process to a solid support, capturing on to the antigen MHC the components that are antigen-specific, then isolating the MHC:antigen complexes which are in turn bound to a planar solid support via a linker.

The current invention is also much more versatile. It is not concerned with detecting natural APCs but is instead directed to the isolation and manipulation of antigen-specific T cells. The manipulation of such T cells is carried out for numerous applications such as directly impacting T cell function by modulating the T cell response. The manipulation can be performed in either a column format, with means for supporting the artificial APCs, and/or in free solution via flow cytometry (FACS). The current invention is able to modulate T cell function because the artificial APCs may be designed to specification in that various functional molecules are incorporated into the APC that activate specific T cell responses. For example, in one embodiment of the current invention, known MHC molecules may be incorporated into liposomes along with a labeled antigenic peptide for which such MHC has specificity (e.g., in the case of FACS a biotinylated antigen). The liposome:MHC:biotinylated antigen complex may be used to bind to antigen-specific T cells and the fact of binding can be visualized by FACS followed by the sorting of the bound cells. Thus, no cell proliferation is necessary to identify and isolate antigen-specific T cells.

In addition to the MHC:antigen complex, the "artificial APCs" used to capture the antigen-specific T cells include accessory molecules to help stabilize the MHC:antigen:TCR interaction, and may also include functional molecules such as co-stimulatory molecules which in one embodiment may be used to activate T cells, adhesion molecules which may be used to bind cells destined for a certain area of the body, and other accessory or functional molecules such as cytokines or antibodies to cytokine receptors, which are known to have immunomodulatory effects upon T cells. Moreover, the current invention further provides for proper orientation of each of these molecules within the artificial APC membrane by a novel use of an anchoring mechanism comprising GM-1 and the β subunit of cholera toxin. In this aspect, the molecule of interest may be connected to the cholera toxin subunit as a fusion protein or by use of a linking moiety. By attaching the cholera toxin subunit to the molecule of interest, the cholera toxin may be bound by the GM-1 that is incorporated into and has affinity for the nonpolar region of the artificial APC membrane.

All of these molecules are incorporated into the liposomes of the artificial APCs in a free floating format. Other molecules may be included that do not influence the modulation of T cell response such as proteins that may be used to anchor the artificial APC to a solid support. Such molecules may also be produced as fusion proteins for proper orientation. As used herein such molecules that are not associated with modulation or T cell binding are termed "irrelevant" molecules.

Additionally, a label may be attached to the antigen, the irrelevant molecule, or the liposome component. Moreover, label may also be noncovalently associated within the lipids of the liposome.

The designs of these artificial APCs also allow for optional expansion experimentation of T cell populations responding to the MHC: antigen complexes associated in the cell like liposomes using a solution based (e.g., roller bottle) cell culture. The concept of the current invention represents a substantial and heretofore unrecognized advance in the MHC:antigen complex T cell binding art in that the artificial APC (e.g. the example comprising liposome:MHC:antigen: accessory molecule-functional molecule complex) is not restricted to complexes of MHC:antigen alone or to a planar surface as is the case with much of the prior art. The importance of the structural differences cannot be over emphasized. The addition of the accessory molecules, as well as co-stimulatory molecules, and other proteins in proper orientation in the liposomes of the current invention allow for substantially improved binding association and manipulation of T cells which is very important in the identification and stimulation of antigen-specific T cells. This is especially true in solution based FACS analysis where functionality of the antigen-specific T cells can be interpreted directly. For example, prior studies (Watts, T. H. *Annals of the New York Academy of Sciences.* 81:7564–7568.) respecting the modulation of T cells may be erroneous. There, it was demonstrated that planar membranes containing purified MHC loaded with antigen fused to glass cover slips elicited IL-2 production by T cells through the interaction of the T cell with the MHC:antigen complex. It was also shown that the same complex when formed in unilamellar vesicles (i.e., liposomes) elicited no response. Contrary to such teaching, we have found that liposome vesicles containing MHC: antigen complexes can in fact elicit strong response when combined with accessory molecules such as LFA-1, and other molecules such as co-stimulatory and adhesion molecules. We based our theory that liposomes could function without use of a planar array on the observation (by the same study cited immediately above) that crude membrane preparations of cellular material from which the MHC was purified were effective in eliciting T cell responses in both planar and vesicular forms. Subsequently, we have discovered that "extraneous" matter existing in cell extracts that might be hypothesized to impart functionality to vesicular forms of lipid bilayers (as opposed to unilamellar liposomes alone) are not important to T cell binding and response. Rather, T cell binding and response is possible using vesicular forms of liposomes containing specific molecules applied in combination with lipsomes (e.g., accessory molecules, co-stimulatory molecules, and adhesion molecules).

Prior research has also been inconclusive respecting the use of MHC molecules. For example, it has been shown (Buus, S. *Cell.* 47:1071–1077.) that a particular antigenic peptide binds solely to the alpha chain of the class II MHC IA$^d$ molecule while other investigations have shown that binding interactions between T cell receptors and MHC: antigen ternary complexes use whole MHC, not just single chains of the MHC, to determine peptide sequence motifs. Exactly how much of a MHC: antigen complex must be presented is not absolutely known and may vary with T cell specificity. We have directed our invention to the use of either whole MHC molecules or those parts of the a and β subunits of Class I and Class II MHC necessary for forming antigen binding cleft regions in the binding of antigen peptides.

The current invention's use of co-stimulatory, adhesion and other accessory molecules in a "free floating" format also helps to both anchor and direct the interaction between MHC:antigen:accessory molecule and T cell receptors by providing a means by which T cells in the sample will be presented with a structure more similar to that found in the natural state. Specifically, the MHC:antigen:accessory molecule complexes in conjunction with other functional molecules are able to migrate in proper orientation in the lipid bilayer of the liposome because of the use of a unique combination of lipids and surfactant molecules, namely an optimal ratio of phosphotidylcholine and cholesterol respectively, included in the liposome matrix. These provide particular protein presentation characteristics and easy protein migration properties to the surface of the liposome structure so that the MHC:antigen complexes can easily migrate to T cell binding loci similar to "capping" events seen in natural APCs. Moreover, as shown in the figures, the structure of our artificial APC liposomes allows for specific "capping" of the liposomes on the surface of the T cells to which the liposomes are bound. Additionally, interaction between the T cell and artificial APC-associated molecules is further enhanced by the molecules being oriented in the lipid membrane such that their active sites are positioned facing outward on the APC. Without such orientation, the ratio of properly oriented molecules to improperly oriented molecules is around 50:50. This ratio is greatly increased using MHC, functional and accessory proteins that have attached thereto (either by fusion protein construction or by use of a linker) a cholera β toxin subunit moiety which is placed in relation to the active center of the protein of interest such that upon the β subunit being bound by GM-1 which is incorporated into the lipid layer of the artificial APC, the protein of interest will lay in the APC with the active site facing outward.

Additional versatility is available with the current invention in that the artificial APCs may incorporate irrelevant molecules to be used in conjunction with separate solid support-based capture moieties for capturing generic target motifs such as irrelevant molecules. Because of the capacity for the functional molecules to migrate in the liposome, the irrelevant molecules may be nonspecifically directed away from the binding position of the T cells thus avoiding steric hindrances. Additionally, the system avoids a need for manufacturing specialized solid phase capture substrates for each antigen-specific complex.

With regard to the capture of the APC by the solid phase component of the invention, we refer to target molecules used in the artificial APC for binding to capture molecules of the solid support as "irrelevant" molecules because they do not impact the APC: T cell interaction. Such a design further preserves the ability of the other molecules inserted into the liposome to move freely and accommodate any capping of the T cell's activation related molecules.

It has been recognized that the number of receptors on a T cell is variable (Rothenberg, E. *Science.* 273:78–79.). It is also known that the number of TCRs and combination of co-stimulatory molecules and accessory molecules varies with the maturation of the T cell (Dubey, C. *J. Immunol.* 157:3820–3289.). How many such receptors are needed in all situations to elicit a T cell response is unknown. Moreover, it is known that presence of a co-stimulatory signal decreases the number of receptors necessary to activate a T cell (Viola, A. and Lanzavecchia, A. *Science.* 273:104–106.). We have provided for the uncertainties presented by such data by providing a system that allows control over the number of MHC:antigen:accessory molecule complexes relative to other functional molecules such as co-stimulatory, and adhesion molecules. The binding and modulation of the T cell response at different stages of cell maturation may be "fine tuned" using our invention.

In another system, Nag et al. in U.S. Pat. No. 5,734,023 (the '023 disclosure), disclosed MHC subunits which were complexed with antigenic peptides and "effector" molecules wherein such complexes were used to identify T cell populations that were associated with autoimmune diseases. The complexes were used to destroy and anergize such T cell populations from a patient's blood cell population.

The effector molecules are described as such things as toxins, radiolabels, etc. which may be conjugated to the MHC or antigen portion of the complexes and which may effecutate the identification, removal, anergy, or death of such T cell populations. Such effector molecules are not related to the attractive binding interactions or T cell responses to effectuate a phenotype change in the cells. They are merely designed and intended to aid in the recognition and/or destruction of specific T cell populations. Additionally, the '023 disclosure uses lipids in the construction of micelles which are designed for intravenous injection as therapeutics. The use of negatively charged acidic phospholipids (such as phosphatidylserine) and the lack of cholesterol or GM-1 and cholera toxin subunit in the design of such micelles differs from that of the current invention in substantial ways. For example, our invention uses neutrally charged phospholipids such as phosphotidylcholine (Pc). We have found that the design of our artificial APCs substantially increases stability because of the Pc and cholesterol in environments where IL-1 is present. IL-1 is known to interact with charged phospholipids and destabilize liposome structure. Likewise, in environments where TNF is present, the permeability of liposomes comprised of charged phospholipids (e.g., phosphotidylserine) is greatly affected. In the same manner, environments where RNase is present may also affect charged phospholipid liposome structures. We have avoided the disruptive effects caused by molecules that are often present in media from which T cells are isolated by designing artificial APCs using neutral phospholipids.

Additionally, the use of liposomes and the parameters associated with micelle construction that are disclosed in the '023 disclosure are wholly associated only with the stability of MHC:antigen:effector molecule complexes in the in vivo circulatory environment. There is no relation inherent or otherwise to the current invention, nor is there insight disclosed as to liposome construction containing co-stimulatory and adhesion molecules or protein orientation mechanisms such as the binding of cholera toxin by GM-1, or fused or linked moieties to the MHC, functional or accessory proteins of interest. Further, the '023 disclosure does not discuss use of its micelle construction in the context of use of a MHC: antigen complex ex vivo where manipulation of T cell function and the binding attraction between T cells and MHC: antigen complexes with respect to the current invention is of import. Moreover, the current invention does not use the technology disclosed in the '023 disclosure of single chain MHC in liposomes. In contrast, in a preferred embodiment, our invention uses either whole MHC molecules or those portions of the α and β subunits necessary to bind antigens and that may be designed to have substantially favorable liposome stabilizing characteristics as well as binding capabilities when in the presence of other functional molecules in the artificial APC as disclosed herein.

In yet another recent disclosure, Spack et al. in U.S. Pat. No. 5,750,356 (the '356 disclosure) describe a method for monitoring T cell reactivity using a modified ELISPOT assay which detects various factors produced by the stimulation of T cells with numerous factors in the presence of natural antigen presenting cells. The current invention is distinguishable from the '356 disclosed method in that the current invention uses artificial antigen presenting cells which have incorporated therein various accessory, co-stimulatory, adhesion, cytokine, and chemokine molecules that provide substantial effect in the binding and modulation of T cell responses. Additionally, in embodiments that require solid support binding, our APC includes irrelevant molecules. Moreover, in another embodiment, our invention includes mechanisms to properly orient proteins of interest in the lipid membrane.

In still another disclosure, Wilson et al. in U.S. Pat. No. 5,776,487 disclose a use of liposome structures for determining analyte in a test sample wherein the liposome contains only an analyte specific ligand and a haptenated component used to bind to a receptor moiety on a solid phase. This combination allows for capturing a test analyte onto a solid support for detection. Thus, it is vastly divergent from the concept of the current invention.

Our methods and artificial APCs are further distinguished from other recent disclosures. For example, Altman et al., in U.S. Pat. No. 5,635,363 (the '363 disclosure), discuss a method for labeling T cells according to the specificity of their antigen receptor by preparing a "stable multimeric complex" comprised of four or more MHC molecules having a substantially homogenous bound peptide population. The multimeric antigen:MHC complex was said to form a stable structure that because of its "stable multimeric" design, purportedly increases the affinity of a T cell receptor for its specific antigen thereby allowing for the labeling, identification and separation of T cells. Although such multimeric MHC components are known to bind T cells, they are not incorporated into liposome structures. Thus, the MHC complexes are unable to participate in capping type concentration. Moreover, the '363 method does not use accessory, co-stimulatory, adhesion, or other molecules to assist T cell binding and/or activation or modulation.

The current invention is further distinguishable over prior disclosures in that our invention is based on the recognition that the valency of the liposome: MHC structure is multiple, and empirically determined. Moreover, we have provided for greater specificity in following APC:T cell interaction due to one embodiment of our invention wherein the antigen is labeled rather than the MHC component (e.g. a biotinylated antigen with a streptavidin molecule conjugated to a fluorochrome).

In light of the above noted distinctions, the disclosed artificial APC and use of a separate solid support containing a binding protein to bind irrelevant molecules on the artificial APC represents an especially notable improvement over prior art. For example, in the above mentioned prior technologies the design of complexes are such that simultaneous binding and capping of the MHC: antigen and TCR/CD3/ accessory molecules cannot occur. Capping is the phenomenon by which the T cell focuses the relevant molecules to the portion of the cell where binding has occurred, thus amplifying the binding, and subsequently the signaling of the event to the cell's other components. The current invention provides a specifically designed lipid bilayer similar to that of a natural cell which allows protein molecules, such as the MHC:antigen complexes to float freely, thus enabling the complexes to conform to any capping events the T cell may undergo. The consequence is a greater ability of the current invention to bind to, stimulate, and modulate T cells on demand.

SUMMARY OF THE INVENTION

The present invention is directed to novel methods of isolating T cells specific for particular antigens of interest and modulating T cell function ex vivo which methods use, in various embodiments, flow cytometry and immunoaffinity chromatography. Additionally, the present invention is directed to artificial antigen presenting cells (artificial APCs) and methods of making artificial APCs. In a preferred embodiment, such artificial APCs are used to isolate, expand, and modulate antigen-specific T cells. Additionally, the present invention is directed to methods of treating conditions which would benefit from the modulation of T cell responses, for example, transplantation therapies, autoimmune disorders, allergies, cancers and viral infections or virtually any T cell mediated disease. The present invention is further directed to a T cell modulation column device as well as a kit for isolating and modulating antigen-specific T cell populations.

Artificial APCs and APC content

In one aspect, artificial APCs are provided having a synthetic membrane-based vesicle, such as a liposome containing cholesterol and neutral phopholipids such as phosphotidylcholine, that functions as an APC having capacities equivalent to a natural APC to bind to and induce an antigen-specific T cell response. Such an artificial APC comprises multiples of homo- or heterogenous combinations of MHC: antigen complexes incorporated therein as well as other functional molecules including accessory molecules, co-stimulation molecules, adhesion molecules, and other immunomodulatory molecules such as cytokines, cytokine receptors, chemokines, and chemokine receptors. Additionally, these APCs may include a mechanism to properly orient these molecules of interest in the APC membrane.

In one embodiment, accessory molecules may be used to facilitate and stabilize the interaction between the antigen specific T cell and the MHC: antigen complex. In this embodiment, an example of an accessory molecule is LFA-1. Other accessory-molecules include, but are not limited to, CD11a/18, CD54(ICAM-1), CD106(VCAM), and CD49d/29(VLA-4), as well as antibodies to each of these molecule's ligands.

In another embodiment, the artificial APC includes co-stimulatory molecules that function to stimulate or activate an antigen-specific T cell. One form of activation is cell proliferation. Suitable co-stimulatory molecules include, but are not limited to, B7-1, B7-2, CD5, CD9, CD2, CD40 and antibodies to their ligands. Preferably, such co-stimulatory molecules can be produced by recombinant methods. Co-stimulatory molecules can be used for a variety of purposes in addition to eliciting cell proliferation. For example, it is known that memory CD4+ T cells express B7-2 whereas naïve CD4+ T cells do not. Neither type cell expresses B7-1 (Hakamada-Taguchi, R. *European Journal of Immunology.* 28:865–873.). Thus, the current invention may be used to selectively target memory T cells by incorporating anti-B7-2 into the artificial APC complex.

In another embodiment, the artificial APC also includes adhesion molecules to facilitate strong and selective binding between the artificial APC and antigen-specific T cells. Suitable adhesion molecules include, but are not limited to, proteins of the ICAM family, for example ICAM-1 and ICAM-2, GlyCAM-1, as well as CD34, anti-LFA-1, anti-CD44 and anti-beta7 antibodies, chemokines, and chemokine receptors such as CXCR4 and CCR5, and antibodies to Selectins L, E, and P. Such molecules are known to be important as homing molecules for cells destined for specific locations in vivo. For example, Alpha4beta7 and L-selectin have been proposed as gut and peripheral lymphnode homing molecules respectively. Alpha4beta7 is expressed mainly on memory T cells while L-selectin is expressed mainly on naïve T cells (Abitorabi, M. A. *J Immunol.* 156:3111–3117.). It is also known that endothelial selectins (E-selectin and P-selectin) are associated with the extravasasion of T cells into inflammatory sites in the skin (Tietz, W. *J Immunol.* 161 :963–970.). In the current invention a beta7 binding molecule and gut addressin MAdCAM-1, or an anti-L-selectin antibody may be incorporated into the artificial APC to distinguish further the type of T cell binding to the MHC: antigen complex.

In another example, it is known that CD44, which binds hyaluronan, is involved in Anti-CD44 antibody will bind to CD44 and strip it from the leukocyte surface. In one embodiment of the invention, anti-CD44 is incorporated into an artificial APC for use in stripping CD44 from leukocytes as desired thereby helping to inhibit the extravasation of the cells into extracellular spaces once the treated cells are returned to the patient. In another embodiment the anti-CD44 can be infused into an immunomodulatory column where the leukocytes have been captured by artificial APCs for the same purpose.

In another embodiment, other functional molecules (i.e., modulation molecules) may be incorporated into the artificial APC to facilitate T cell modulation. Examples of such molecules which may be incorporated into the artificial APC include, but are not limited to, CD72, CD22, and CD58, or antibodies to their ligands, antibodies to cytokine or chemokine receptors or small molecules which mimic the actions of the various cytokines or neuropeptides. These modulation molecules may be used for example to modulate the phenotype of antigen-specific T cells.

In another embodiment of the invention, the artificial APCs may also comprise irrelevant molecules which are included for the purpose of providing a means to anchor the APC to a solid support or to carry a label. Such molecules are termed irrelevant because they do not interact with the binding, activation, or modulation of the T cells.

In still another embodiment, any of the aforementioned molecules of interest (i.e., MHC, functional, accessory, irrelevant) may be bound to a cholera toxin subunit moiety by either a linking moiety of by a recombinant construction of a fusion peptide wherein the toxin subunit is linked directly to the protein of interest. In such embodiment, the cholera toxin subunit is positioned with respect to the molecule of interest such that the active portion of the molecule of interest is available for contact with T cells while the toxin portion remains in the nonpolar region of the lipid layer of the APC. In a preferred embodiment, the cholera toxin moiety remains in the APC's interior by binding to GM-1 that is incorporated into the APC's lipid interior.

In still another embodiment, the APC comprises phospholipids, cholesterol, and GM-1 molecules each present in an appropriate ratio to allow free migration of molecules of interest around the lipid layer. Phospholipids contemplated include neutrally charged phospholipids such as phosphotidylcholine and cholesterol. Additionally, the cholesterol provides a surfactant property allowing the phospholipid to carry the various molecules of interest (accessory, irrelevant, modulation, adhesion, and co-stimulatory) in a manner that aids the free mobility of such molecules within the liposome membrane layer without disruption of the membrane in ex vivo environments.

In still another embodiment, the APC comprises antigens wherein the antigens are presented by an MHC components for contact with and recognition by a T cell receptor. Such antigens may be selected from the group consisting of a peptide, a peptide derived from the recipient for graft versus host diseases, a cancer cell-derived peptide, a peptide derived from an allergen, a donor-derived peptide, a pathogen-derived molecule, a peptide derived by epitope mapping, a self-derived molecule, a self-derived molecule that has sequence identity with said pathogen-derived antigen, said sequence identity having a range selected from the group consisting of between 5 and 100%, 15 and 300%, 35 and 100%, and 50 and 100%.

In still another embodiment, the APC comprises labels wherein a label is associated with at least one of the group selected from the group consisting of a lipid bilayer of the liposome components, a lipid of the liposome, an antigen, an MHC molecule, a co-stimulatory molecule, an adhesion molecule, a cell modulation molecule, GM-1, cholera toxin β subunit, an irrelevant molecule, and an accessory molecule.

Artificial APC Formation

In a preferred embodiment, artificial APCs may be made by:
  (a) obtaining MHC:antigen complexes of interest;
  (b) combining said MHC:antigen complexes and accessory molecules such as ICAM-1, with an artificial lipid membrane comprising the aforementioned lipids, cholesterol, and GM-1 molecules to form membrane-associated MHC:antigen:accessory molecule complexes, (i.e., liposome:MHC:antigen:accessory molecule complexes); and
  (c) combining said liposome:MHC:antigen:accessory molecule complexes resulting from step (b) with one or more types of functional molecules (i.e.), other accessory molecules, co-stimulatory molecules, adhesion molecules, modulation molecules, and irrelevant molecules) to form an artificial APC comprising liposome: MHC:antigen:accessory molecule:functional molecule complex. Preferably, steps (b) and (c) are performed simultaneously. Additionally, in this embodiment example, as well as all others mentioned herein, each of these molecules incorporated may be prelinked to cholera toxin (as by fusion protein construction or linker moiety).

In one embodiment, the functional molecules are individually optional. In another embodiment the irrelevant molecules are optional.

In another preferred embodiment, the artificial APCs may be made by:
  (a) obtaining a spheroid solid support of interest having affinity for non-polar regions of a phospholipid; and
  (b) combining MHC:antigen complexes, accessory molecules such as LFA-1, and functional molecules (i.e., other accessory molecules, co-stimulatory molecules, modulation molecules, irrelevant molecules, and adhesion molecules) with the phospholipid, cholesterol, GM-1 components and solid support to form a solid support associated:membrane-bound:MHC:antigen:accessory molecule:functional molecule complexes (i.e., solid support:phospholipid:MHC:antigen:accessory molecule:functional molecule complex) wherein of the molecules of (b), none are covalently bound to the solid support except optionally the lipid component.

In this embodiment, the solid support is preferably a glass bead or magnetic bead. It is also preferred that the phospholipid be phosphotidylcholine. In one embodiment of this aspect, the functional molecules are individually optional. In another embodiment, the solid support is either a glass or magnetic bead and has a diameter of between 25 and 300 μm. Additionally, another solid-support APC construct has only lipids, cholesterol and a capture moiety having affinity for capturing an irrelevant molecule that is located on a non-solid-support APC. In such construct, the lipid layer is generally a monolayer.

Artificial APC Methods of Use

In another embodiment, the present invention is directed to a method of isolating T cells specific for an antigen of interest using an artificial APC comprising:
  (a) obtaining a biological sample containing T cells which are specific for an antigen of interest;
  (b) preparing a liposome:MHC:antigen:accessory molecule:functional molecule complex (i.e. artificial APC), wherein the antigen in said complex is said antigen of interest;
  (c) contacting the biological sample obtained in step (a) with the artificial APC obtained in step (b) to form a artificial APC:T cell complex;
  (d) removing said complex formed in step (c) from said biological sample; and
  (e) separating T cells specific for said antigen of interest from said complex formed in step (c).

Optionally, such a method of isolating T cells specific for a particular antigen of interest may include the step of determining the quantity of such T cells complexed with the artificial APC, and/or may include the step of characterizing the functional phenotype of such T cells. Preferred biological samples containing T cells specific for an antigen of interest include bodily fluids such as blood, blood plasma, and cerebrospinal fluid. Other suitable biological samples include solid tissue, for example histological specimens.

In a preferred embodiment, the method uses FACS technology, and the antigen is labeled. Preferred labels include biotin, fluorochromes and radioactive labels. For example, one type of label which may be used is vancomycin (Rao et al., *Science*, Vol. 280:5364:708–11,1998). In another embodiment of the method, also using FACS technology, the liposome may be labeled or the label may be noncovalently enclosed within the liposome matrix. If the label is within the liposome matrix, the label may be either enclosed within the liposome or incorporated within the lipids of the outer membrane of the liposome. In another embodiment, the irrelevant molecule, if present, may be labeled. In yet another embodiment, the complex of the artificial APC and T cell may be removed from the biological sample by capturing the complex via the irrelevant molecule on to a solid support. In such case, a solid support comprises an irrelevant molecule binding or capture molecule (e.g. anti-irrelevant molecule antibody) bound either directly to the solid support or noncovalently associated with a phospholipid bound to the support.

In another embodiment, the present invention provides an alternate method of isolating T cells specific for an antigen of interest. This alternate method comprises:
  (a) contacting an artificial APC having a MHC:antigen: accessory molecule component of interest with a solid support to form a solid support artificial APC (The liposome of the APC contains a binding molecule i.e., an "irrelevant" binding molecule. The capture molecule that captures the irrelevant molecule may be bound to said solid support via a linker or may be associate with a phospholipid layer on the solid support). In this embodiment, the antigen binding region of said MHC: antigen component is available for binding to a T cell receptor without steric hindrance because the MHC: antigen component is free to move within the liposome membrane of the APC while the irrelevant binding protein allows the APC to be anchored to the solid support;
  (b) contacting said solid support artificial APC with a biological sample containing T cells specific for an antigen of interest to form a solid support artificial APC:T cell complex;
  (c) removing said solid support: artificial APC:T cell complex from said biological sample; and
  (d) separating the T cells specific for said antigen of interest from said complex.

In a further aspect of the present invention, kits for the isolation of T cells specific for an antigen of interest are provided. In one embodiment, the kits comprise:
- (a) APCs and solid supports such that there is included APCs having MHC (and other functional molecule where desired) complexes; and
- (b) materials well known to those knowledgeable in the art which facilitate the completion of the isolation of an antigen-specific T cell population including, but not limited to, buffers, culture medium, (included in buffers may be cytokines, antibodies to various transmembrane or soluble molecules, chemokines, neuropeptides, or: steroids), (included in culture medium may be cytokines, antibodies to various transmembrane or soluble molecules, chemokines, neuropeptides, or steroids), antigens, MHC molecules, accessory molecules, co-stimulatory molecules, modulatory molecules and adhesion molecules.

In another kit embodiment, the kit may comprise a solid support having a means to capture an irrelevant molecule located in an artificial APC, and an artificial APC constructed as described above. In another embodiment, the kit may comprise virtual artificial APCs or solid supports comprising a lipid layer.

In another preferred embodiment, the invention includes an antigen-specific T cell isolation and modulation column device. In this embodiment, the device comprises compartments that may be isolated from one another having entrance and exit flow ports between said compartments and between the compartments and external apparatuses. Any of the compartments of such column device may further comprise solid supports capable of binding irrelevant molecules of artificial APCs or solid supports that function directly as artificial APCs as described above. Moreover, such a device may be used in connection with soluble immunomodulatory molecules that are neither bound to a solid support or incorporated into an artificial APC. Examples of such molecules include cytokines, chemokines and hormones.

In another such example, if leukopheresis is being performed with the intention of reintroducing the cells back into the patient's body, soluble factors may be introduced into a column device to induce production of IL2 in naïve T cells, IL2 being necessary for T cell growth. Likewise, IL4 or soluble IL4 receptor antibody may be introduced into an immunomodulatory column to enhance the Th2 phenotype in specific T cells of interest.

The invention further comprises a method of modulating T cell responses (i.e., altering a T cell's phenotype). In such embodiment, methods of regulating or modifying T cell responses ex vivo, such as in a column device of the invention, are provided comprising the steps of isolating T cells which are specific for an antigen of interest and combining said isolated T cells with an artificial antigen presenting cell. The aforementioned steps may be performed simultaneously or separately as by addressing antigen-specific T cells from one compartment to another after first capturing the T cell followed by introduction of an artificial APC. Preferably, the T cells specific for an antigen of interest are isolated using the T cell isolation methods described above.

The modulation of T cell response may comprise changing, in whole or in part, the functional pattern of cytokine receptor expression, cytokine production, chemokine production, and/or chemokine receptor expression by the isolated T cells specific for a given antigen. For example, a T cell may be stimulated to shift its phenotype from a Th0 to a Th1. In another example, a T cell may be stimulated to shift its phenotype from a Th1 response to a Th2 response. In yet another example, a T cell may be stimulated to shift from any other phenotype to a Th3 phenotype. Amongst the many possible means to induce modulation of a T cell response for the purpose of increasing its Th2 response and/or decrease its Th1 response, preferably the artificial APC used in such method expresses the co-stimulatory molecule B7-2.

In another embodiment, the modulation of T cell response may comprise changing, in whole or in part, the functional pattern of cytokine production by said isolated T cells from a Th2 response to a Th1 response. Preferably, to modify a T cell response to induce it to increase its Th1 response and/or decrease its Th2 response, the artificial APC used in such method expresses the, co-stimulatory molecule B7-1.

In another example of T cell modulation, it is known that ST2L expression is Th2-type specific. In the current invention, ST2L may be included in the APC in order to identify, isolate and extract antigen-specific T cells of the Th2 phenotype and/or enrich T cell population for antigen-specific Th1 phenotype in the treatment of autoimmune disease.

In another example, OX40 ligand is known to induce a Th2-like phenotype in naïve T cells (Flynn, S. *Journal of Experimental Medicine.* 188:2:297–304.). In the current invention, OX40 may be incorporated into and artificial APC to selectively induce a Th2 phenotype.

In another example, CD30 is known to have association with asthma (Spinozzi, F. *Mol Med.* 1:7:821–826.). In the current invention, CD30 may be incorporated into artificial APCs to identify, isolate and remove antigen-specific T cells of the Th2 phenotype or to augment T cell response away from harmful T helper cells in the treatment of allergic conditions.

In yet another embodiment, the modulation of T cell response may comprise inducing anergy and/or apoptosis. Since it is known that the same cell need not present both the specific antigen and the co-stimulatory molecule for T cell activation (Ding, L and Shevach, E. M. *European Journal of Immunology.* 24:4:859–866.), our system is applicable to situations where the artificial APC does not express a co-stimulatory molecule, or contains another effector molecule, e.g. Fas ligand, to induce anergy. Thus, the artificial APC used in such method would not express a co-stimulatory molecule but may alternatively express Fas ligand.

In yet another embodiment, the modulation of T cell response may comprise inducing T cell proliferation in general, without regard to modifying Th1 or Th2 response, and without regard for inducing anergy. Preferably, this is accomplished by an artificial APC that expresses an anti-CD28 antibody.

In yet another preferred embodiment, the present invention provides methods of treating a condition in a subject who would be benefited by modulating the functional pattern of active factors expressed by a T cell. Such method of treatment could include in addition to the use of artificial APCs, the use of a column device described herein. For example, in such a treatment regimen, production of cytokines by a T cell may be modified in certain antigen-specific T cells to increase Th2 response and/or decrease Th1 response. In such a method, a subject's T cells that are specific for an antigen capable of triggering a Th1 response are isolated by contacting said cells with an APC having an MHC:antigen complex containing an appropriate antigen. By also including the co-stimulatory molecule B7-2 on the APC, the T cells may be directed to modify their response and cytokine production to increase a Th2 response. Conditions which would be benefited by altering the functional pattern of response toward a Th2 response include, for example, autoimmune diseases such as type 1 diabetes mellitus, multiple sclerosis, rheumatoid arthritis, dermatomyositis, juvenile rheumatoid arthritis and uveitis.

In another example of a method of treatment, it is known that the cross-linking of the CD40 ligand by means of antibodies induces cell proliferation and IL4 production (Blotta, M. H. *J. Immunol.* 156:3133–3140.). Additionally, it is known that blockade of CD40/CD40 ligand pathway induces tolerance in murine contact hypersensitivity (Tang, A. *European Journal of Immunology.* 27:3143–3150.). In the current invention, CD40 or anti-CD40 ligand antibody may be incorporated into an artificial APC to induce T cell modulation toward production of IL4 and/or tolerance to alleviate inflammatory autoimmune disorders.

In yet another example of a method of treatment, a subject may be benefited by altering the functional pattern of cytokine production by certain antigen-specific T cells to increase Th1 response and/or decrease Th2 response. Such methods comprise isolating a subject's T cells that are specific for an antigen capable of triggering a Th2 response by contacting said cells with an APC containing an MHC:antigen complex having an appropriate antigen, wherein said artificial APC also expresses the co-stimulatory molecule B7-1. Conditions which would be benefited by altering the functional pattern of cytokine production to increase Th1 response and/or decrease Th2 response include, for example, allergy, for example allergy to dust, animal skin bypass products, vegetables, fruits, pollen and chemicals. Other conditions which may be benefited include cancers and some types of infections (e.g., viral, protozoan, fungal and bacterial).

In another example of a method of treatment, it is known that anti-B7-1 antibody will reduce the incidence of EAE, an animal model of multiple sclerosis. Anti-B7-2 antibody is known to increase the severity of EAE, while co-treatment with anti-IL4 antibody will prevent disease amelioration. In the current invention, more than one level of control with respect to this disease is possible. For example, artificial APCs may be generated that express anti-B7-1 antibody and/or IL4 to elicit T cell response favorable to treating the disease.

In another example, a regimen may be developed for treating melanoma by screening for T cell responses to epitopes derived from MAGE-1, MAGE-3, MART-1/melan-A, gp100, tyrosinase, gp75, gp15, CDK4 and beta-catenin, all of which are known to be associated with the disease. T cells having specificity for these molecules may be activated and modulated in various ways. For example, T cells that are specific for a unique cancer related antigen can act to cause destruction of the cancerous cells may be proliferated and infused into a patient.

In another example of a method of treatment, artificial APCs may be designed to augment antigen-specific T cell response away from the harmful helper type T cells or used to deplete offending T cells in the treatment of multiple sclerosis. Such depletion or modulation of the T cells may be carried out in combination with the infusion into a column device of either Fas, Fas Ligand, anti-Fas or anti-Fas ligand antibody. Additionally, artificial APCs may be designed to incorporate SLAM reactive molecules into the liposome complex which functions to induce a suppressive phenotype.

In another treatment example, SLAM reactive molecules incorporated in an artificial APC may be used to treat Th2-mediated autoimmune diseases by modulating the T cell response to shift from a Th2 profile to a Th0/Th1 profile while at the same time inducing IL-2 independent, co-stimulation independent proliferation.

In yet another treatment example, cartilage degradation that is associated with rheumatoid arthritis can be prevented by use of IL-10 and IL-4 in an artificial APC or by infusion of the soluble molecules into a column device to modulate antigen-specific T cells away from activated Th1 state.

In yet another treatment example, IL-12 can be used such as by infusion into a column device or incorporation in an artificial APC to induce Th1 type inflammatory response to help treat Th2 mediated autoimmune diseases.

In another example of a treatment method, T cell mediated milk intolerance may be treated by isolation and depletion of T cells specific for the allergen which is incorporated as an MHC bound antigen on an artificial APC.

In still another example of using the invention to treat cancerous conditions, T cells specific for the ras peptide, or variants thereof, may be stimulated by response to an artificial APC containing the ras peptide in the treatment of cancerous cells expressing the ras mutation.

In another example of the advance of the current invention over that of currently applied art, instead of observing the effects of specific molecules on T cell response in vivo, the current invention allows one to follow T cell modulation ex vivo. For example, previous studies (Gaur, A. *J of Neuroimmunol.* 74:149–158.) showed that using I.V. injection of non-encephalitogenic APL91 peptide of MBP ameliorates disease by shifting cytokines from Th1 to Th2 phenotype. The same type of injections using encephalitogenic superagonist APL A97 ameliorates disease by causing deletion of specific T cells. The problem arises that understanding the bioavailability of the injected complexes is difficult at best while the ex vivo methodology of the current invention allows one to follow the specific actions of the peptides when used either in an artificial APC or in soluble form in a column device.

In another situation, prior studies have indicated that in vivo application of peptides to treat autoimmune disease states is related to epitope spreading resulting in relapsing episodes of disease (Lehmann, P. V. *Nature.* 358:6382: 155–157.), (McRae, B. L. *Journal of Experimental Medicine.* 182:75–85.). The ex vivo application of the current invention is preferred because specific peptides can be used to isolate and identify antigen-specific T cells without exposing a patient to the danger of epitope spreading that is associated with relapses of certain autoimmune diseases.

In a further preferred embodiment of the invention, a method of identifying T cells that express MHC epitopes important to graft versus host rejection in transplantation therapy is provided. In this embodiment, such MHCs are identified followed by their incorporation into the artificial APC. Such APCs may be used to capture and deplete the recipient's T cells having specificity for such epitopes so as to allow a favorable modulation of the recipient's immune response to the graft. More specifically, peptides derived from the MHC of a recipient are bound to the MHC of a donor that are incorporated into artificial APCs. Such APCs are used in combination with tolerogenic stimuli also on the APC or infused into the immunomodulatory column. The donor's T cells are then screened to bind reactive T cells that can then be discarded. In a preferred embodiment, the column device of the invention can be used to carry out such immunoleukophoresis.

In another embodiment, the method contemplates treatment of an individual to cause a favorable immune modulation to an allograft comprising:

(a) predicting a donor's MHC to which a recipient may react;

(b) testing the predicted MHC epitopes with a recipient's T cells to identify antigenic epitopes;

(c) using identified epitopes in an artificial APC to deplete the recipient's antigen-specific (i.e., donor-specific) T cells while additionally desensitizing the recipient to the epitope by contacting the recipient (as by feeding or nasal injection) with increasing doses of the donor-specific antigen.

In still another preferred embodiment, the invention provides a method of identifying an individuals' MHC epitopes that are of import in immunologic responses to pathogenic agents. In this embodiment, an individual's MHC is screened for epitopes that have appreciable sequence or molecular structure recognition with pathogen-derived molecules. The identified MHC epitopes can be used to elicit immunity that may be employed directly as a vaccine against such MHC epitopes that have sequence recognition with pathogen-derived peptides. For example, such a vaccine may be used to reduce natural APCs that express MHC molecules associated with autoimmune diseases including, but not limited to, multiple sclerosis, rheumatoid arthritis, and diabetes. In another preferred embodiment, the identified MHC epitopes can be incorporated into a liposome structure as a co-stimulatory molecule to enhance the effect of artificial APCs that express other disease related antigens.

In yet another preferred embodiment, antigenic moieties of the pathogen which have or are likely to have MHC mimics may be used in artificial APC MHC:antigen complexes to isolate T cells specific for such pathogen-derived antigenic motifs or mimics thereof for the production of a T cell vaccine. Such a vaccine may be used to directly fight progression of an infection or disease caused by a pathogen or that is the result of a pathogen-derived antigen induced autoimmune associated inflammatory response. Usually a self-derived molecule that mimics a pathogen-derived antigen comprises a polypeptide. As used herein such a mimic has an amino acid sequence identity with said pathogen-derived antigen to an extent necessary for the MHC to bind to the mimic. The range of sequence identity may be anywhere between 5 and 100% depending upon which amino acids in a peptide sequence elicits either recognition by the MHC and/or stimulation of a T cell response. Generally, the range is between 5 and 100%, usually, the range is between of a range of 15 and 100%, preferably the range is between 35 and 100%, and most preferably the range is between 50 and 100%.

In still other embodiments, the invention provides a means to address other immunologic conditions relevant to T cell response. For example, apoptosis of T cells induced by MHC molecules through the CD95/CD95 ligand pathway can be controlled by incorporating anti CD95 into an artificial APC and modulating antigen-specific T cells.

In another application, dendritic cells important to immune response may be manipulated ex vivo in the same fashion as T cells in the many examples provided above.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. The invention will be further described with reference to the accompanying drawings in which:

FIG. 7 is a schematic showing other embodiments of artificial APC designs wherein

FIGS. 16(A–D), 17(A–D), and 18(A–D) are color photos showing that the interaction of T cells with artificial APCs allows physiological migration of TCR proteins toward the interaction side, i.e., "capping". Resting 8DO T cells were stained with FITC-cholera toxin, incubated with artificial APCs presenting $IA^d/OVA^{323-339}$ complexes and analyzed by confocal microscopy. Panels A and B of each of FIGS. 16–18 show the red and green fluorescent dyes, respectively. Panel C shows the cells as seen by phase contrast. Panel D is the combination of the two fluorescent dyes with phase contrast. Panel D shows the combined fluorescence of the red and green dyes so that co-localization (FIG. 16D), and capping (FIGS. 17D, and 18D) are observed. Specifically, FIGS. 16A–D shows 8DO cells alone stained with Alexa 568-anti CD3 (red) bound to the T cell receptor and FITC-cholera toxin (green) bound to the cholera toxin. Thus, FIGS. 16A–D shows that the T cell receptor is associated with the cholera toxin antigen. This further shows that cholera toxin is a good tool for identifying the T cell receptor in this system. FIGS. 17A–D shows that the interaction between T cells and artificial APCs allows physiologic migration and capping of the T cell receptor in the T cell membrane.

FIGS. 19A–D are PAGE photos showing optimization of peptide (antigen) loading of human and mouse MHC class II molecules wherein detergent solubilized MHC class II molecules were incubated with biotinylated peptides at the designated pH and temperature for 16 and 24 hrs. Peptide loading was analyzed through ECL. FIGS. 19A and B show binding of biotinylated PADRE peptide to HLA-DR4. FIGS. 19D and C show binding of biotinylated OVA 323–339 to mouse IAd. The photos show output signal of the level of binding of the peptides to MHC. Results indicate that an incubation of 16 hrs at room temperature and pH 7 and a molar ratio of 200 to 1 provide for optimal results with respect to the human MHC and 1000 to 1 for the mouse.

FIG. 25A shows IFA only-immunized mice.

FIGS. 27A–C is a schematic showing methodology for orienting molecules of interest in the APC liposome matrix. In 27A, a molecule of interest such as MHC, functional, accessory, adhesion, or irrelevant molecule, may be synthesized by recombinant methods well known to those skilled in the art and linked to GM-1 by a linker and properly oriented in the APC membrane. In 27B, a molecule of interest may be constructed as a fusion protein with cholera toxin P subunit and the fusion protein anchored in proper orientation in the APC membrane by the cholera toxin moiety binding to GM-1. In 27C, a cholera toxin subunit may be chemically linked to SPDP linker (Pierce) and then attached to a molecule of interest followed by anchoring to a GM-1 containing APC. In any of the above, the cholera toxin, GM-1, linkers may be synthetically produced. In the figure, A represents a gene for a molecule of interest, B represents the gene for the β subunit of cholera toxin, A1 is an expression vector, A2 represents expression and isolation of the cloned gene, A3 is an expressed molecule of interest, B1 is a fusion protein of a molecule of interest and cholera toxin, A4 is a linker, A5 is an artificial APC containing GM-1, A7 is a partial view of an artificial APC wherein the molecule of interest is directly linked to the GM-1, C is choler toxin subunit, C1 is a linker, C2 is a molecule of interest, C3 is a choler toxin subunit attached to a linker, C4 is a molecule of interest linked to a choler toxin subunit, E represents a liposome bilayer, E1 shows GM-1, E2 is an artificial APC containing GM-1, and F is a partial view of an artificial APC having a molecule of interest bound to the APC by the binding interaction of the GM-1 and cholera moiety.

DETAILED DESCRIPTION OF THE INVENTION

The present invention is directed to novel methods of isolating T cells specific for particular antigens of interest and modulating T cell function ex vivo which methods use, in various embodiments, flow cytometry and immunoaffinity chromatography. Additionally, the present invention is directed to artificial APCs and methods of making artificial APCs. In a preferred embodiment, such artificial APCs are used to isolate, expand, and modulate antigen-specific T cells. Additionally, the present invention is directed to methods of treating conditions that would benefit from the modulation of T cell responses, for example, transplantation therapies, autoimmune disorders, allergies, cancers and viral infections, and virtually any T cell mediated disease. The present invention is further directed to a T cell modulation column device as well as a kit for isolating and modulating antigen-specific T cell populations.

Artificial APC Composition

Figure 1:
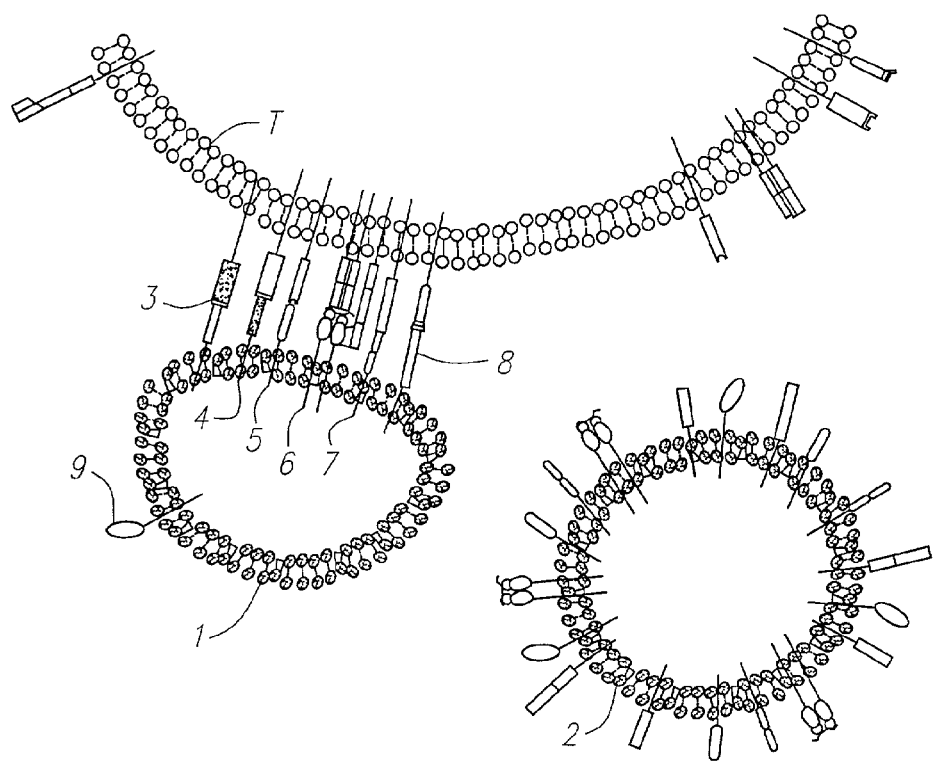
FIG. 1 is a schematic representation of the basic features of the invention and it's interaction with various molecules on a T cell, where (1) is an artificial APC who's embedded molecules have conformed to the capping of the T cell, where (2) is an artificial APC that has not interacted with a T cell and who's molecules are randomly dispersed through the membrane, where (T) is a T cell who's molecules have capped in response to the interaction with the artificial APC, where (3) is an accessory molecule for stabilizing the binding between the TCR and MHC:antigen complex, where (4) may be T cell accessory or adhesion molecule ligands, where (5) may be T cell co-stimulatory molecule ligands, where (6) may be an MHC:ag complex, where (7) may be cytokine related molecules, where (8) may be chemokine related molecules, where (9) may be an irrelevant molecule used in binding of the artificial APC to a solid support or a molecule which is tagged with a molecule used in visualization.

According to preferred embodiments of the current invention, an artificial APC may comprise MHC:antigen complexes, accessory molecules and other functional molecules including, but not limited to, co-stimulatory molecules, adhesion molecules, modulation molecules, irrelevant molecules, GM-1 and subunits of cholera toxin attached to any of the aforementioned molecules, and labels which are collectively incorporated within or are associated with the lipids of a liposome or other membrane-based vesicle such as depicted in FIG. 1. Such incorporated or associated molecules may also include GPI anchored proteins.

In a first embodiment, the lipid membrane component comprises neutral phospholipids such as phosphotidylcholine and surfactant elements such as cholesterol. These materials are provided in a proper ratio that allows the other molecules of interest to freely migrate in the membrane layer. Other lipid membrane components include GM-1 which is a transmembrane pentasaccharide and associates in part with nonpolar regions of the liposome matrix. This GM-1 can be used in association with cholera toxin P subunit to orient molecules of interest in the liposome matrix.

Accessory molecules may be included for the purpose of stabilizing the interaction between a TCR and an MHC:antigen complex. Suitable accessory molecules may include, but are not limited to, LFA-1, CD49d/29(VLA-4), CD11a/18, CD54(ICAM-1), and CD106(VCAM) and antibodies to their ligands. In a preferred embodiment, the artificial APC includes ICAM-1 as such an accessory molecule.

Co-stimulatory molecules may be included for the purpose of stimulating or activating a TCR. Suitable co-stimulatory molecules may include, but are not limited to, B7-1, B7-2, CD5, CD9, CD2, CD40, and antibodies to their ligands such as anti-CD28.

Adhesion molecules may be included for the purpose of enhancing the binding association between the artificial APC and a T cell. Suitable adhesion molecules may include, but are not limited to, members of the ICAM family such as ICAM 1, ICAM 2 and GlyCAM-1, as well as CD 34, anti-LFA-1, anti-B7, and chemokines such as CXCR4 and CCR5, and antibodies to selectins L, E, and P.

Modulation molecules may be included for the purpose of modulating the phenotype of a T cell. Suitable modulation molecules may include, but are not limited to, CD72, CD22, and CD58 and antibodies to their ligands, antibodies to cytokine or chemokine receptors or small molecules which mimic the actions of the various cytokines or neuropeptides.

Irrelevant molecules may be included for the purpose of either carrying a label or serving as a scaffold for binding to a solid support. Such a molecule can be any peptide or other molecule having characteristics that make it suitable for use with a liposome and antigen carrier. Such molecule should not interfere with the binding of a T cell to the artificial APC.

With respect to the, incorporation of each of the aforementioned MHC, accessory, co-stimulatory, adhesion, modulation, and irrelevant molecules in the artificial APC, proper orientation of these molecule's active centers may be provided by combining the molecules with the β subunit of cholera toxin so that the cholera toxin subunit can be recognized and bound by GM-1 which is incorporated into the liposome membrane matrix. The incorporation of the cholera toxin and orientation mechanism markedly increases the ability of the artificial APC to interact with T cells and other cells and molecules due to the proper orientation of incorporated molecules from about 50% without such orienting to 90% or more with such orienting.

In another embodiment, the aforementioned molecules of interest may be produced by recombinant technology as is well known to those skilled in the art. Use of recombinant technology produced molecules further provides the opportunity to produce such molecules as fusion molecules comprising the molecule of interest attached to the β subunit of cholera toxin. In another embodiment, the recombinantly produced (or for that matter a purified natural molecule) may be linked to cholera toxin by a commercial linker.

In still another embodiment, the APC comprises antigens wherein the antigens are presented by an MHC components for contact with and recognition by a T cell receptor. Such antigens may be selected from the group consisting of a peptide, a peptide derived from the recipient for graft versus host diseases, a cancer cell-derived peptide, a peptide derived from an allergen, a donor-derived peptide, a pathogen-derived molecule, a peptide derived by epitope mapping, a self-derived molecule, a self-derived molecule that has sequence identity with said pathogen-derived antigen, said sequence identity having a range selected from the group consisting of between 5 and 100%, 15 and 100%, 35 and 100%, and 50 and 100%.

Examples of some antigens noted above include the peptide QKRAAYDQYGHAAFE (Seq. Id. No. 10) which is derived from *E. coli* dnaJp1 heat shock protein. A human self-derived peptide is QKRAAVDTYCRHNYG (Seq. Id. No. 11) derived from the HLA. This peptide also has sequence identity with the pathogen Sequence Id. No. 10. Peptides derived from epitope mapping include human peptides from the HA I matrix GILGFVFTL (Seq. Id. No. 12), VKLGEFYNQ (Seq. Id. No. 13) which is a HA I nucleoprotein, and PKYVKQNTLKLAT (Seq. Id. No. 14) derived from the HA II locus.

In still another embodiment, the APC comprises labels wherein a label is associated with at least one of the group selected from the group consisting of a lipid bilayer of the liposome components, a lipid of the liposome, an antigen, an MHC molecule, a co-stimulatory molecule, an adhesion molecule, a cell modulation molecule, GM-1, cholera toxin β subunit, an irrelevant molecule, and an accessory molecule.

Artificial APC Formation

Such artificial APCs may be made by:

(a) obtaining an MHC:antigen complex of interest;

(b) combining said MHC:antigen complex with an artificial lipid membrane to form a membrane-associated MHC:antigen complex, (i.e., a liposome:MHC:antigen complex); and (c) combining said liposome:MHC:antigen complex resulting from step (b) with any of the following: accessory molecule, a co-stimulatory molecule, an adhesion molecule, a modulation molecule, and an irrelevant molecule to form an artificial APC comprising a liposome:MHC:antigen:functional molecule: complex. Steps (b) and (c) may be performed simultaneously. In one embodiment of this method, step (c) is optional in whole or in part with respect to any of co-stimulatory, adhesion, modulation, irrelevant molecules or GPI proteins. In another embodiment, any of the molecules of interest (MHC, accessory, co-stimulatory, adhesion, modulation, irrelevant molecules) can be bound to the β subunit of cholera toxin and GM-1 can be included in the APC lipid matrix to provide a means for proper orientation of the molecules of interest such that their active centers are oriented to facilitate interaction with T cells and other components external to the APC.

By "membrane-associated" is meant the non-covalent attraction between the lipid molecules of a liposome and MHCs, antigens, accessory molecules, co-stimulatory molecules, adhesion molecules, modulation molecules, irrelevant molecules, GM-1, and cholera toxin β subunit.

In another preferred embodiment, the artificial APCs may be made by:

(a) obtaining a spheroid solid support of interest having affinity for non-polar regions of a phospholipid; and (b) combining MHC:antigen complexes, accessory molecules such as ICAM-1, and functional molecules (i.e., other accessory molecules, co-stimulatory molecules, modulation molecules, irrelevant molecules and adhesion molecules) with the phospholipid and solid support to form a solid support associated:membrane-bound:MHC:antigen:accessory molecule:functional molecule complexes (i.e., solid support:phospholipid: MHC:antigen:accessory molecule:functional molecule complex).

In this embodiment, the solid support is preferably a glass bead or magnetic bead. It is also preferred that the phospholipid be phosphotidylcholine. In one embodiment of this aspect, the functional molecules are individually optional. In another preferred embodiment, the molecules may be properly oriented by inclusion of a molecule bound to cholera toxin and GM-1 in the APC membrane matrix. In another embodiment the complex may include an irrelevant molecule for carrying a label. In still other embodiments, the antigen may have a label. In still other embodiments, a label may be noncovalently associated with the lipid layer.

In yet more embodiments of this solid-support APC construct, the solid support is a glass or magnetic bead having a diameter of about between 25 to 300 µm. In still another embodiment, the solid-support APC construct has only lipids, cholesterol and a molecule having affinity for binding to an irrelevant molecule that is located on another APC (either solid-support based or non-solid support bases). This construct allows for such molecule (which is also an "irrelevant" molecule) to float freely in the lipid layer for proper migration to aid binding of APCs that have bound to T cells.

Artificial APC Uses and Methods

In another aspect, the present invention is directed to a method of isolating T cells specific for an antigen of interest comprising:
(a) obtaining a biological sample containing T cells which are specific for an antigen of interest;
(b) preparing an artificial APC as described herein comprising an MHC:antigen component, wherein the antigen in said component is said antigen of interest;
(c) contacting the biological sample obtained in step (a) with the artificial APC obtained in step (b) to form an artificial APC:T cell complex;
(d) removing said complex formed in step (c) from said biological sample; and
(e) separating T cells specific for said antigen of interest from said complex.

Any suitable biological sample that contains T cells specific for the antigen of interest may be used in the method. Suitable biological samples containing T cells specific for an antigen of interest include fluid biological samples, such as whole blood, blood cells, blood plasma and cerebrospinal fluid, and solid biological samples, such as tissue, for example, histological samples. In one embodiment of the above example, the artificial APC may be complexed to a solid support in addition to the T cell. The complexing of the APC to the solid support provides a means to anchor the APC so that it and any T cell binding to it can be preferentially captured and isolated from extraneous matter. In such case, the solid support may be a glass or magnetic bead that is coated with a lipid monolayer that is bound to the bead by, for example, a linker. The solid support may additionally have noncovalently bound accessory molecules associated with the lipid layer such as binding molecules that recognize and bind to irrelevant molecules associated with the artificial APC. In another embodiment, the binding molecules may be covalently bound to the solid support by a linker. Additionally, the lipid layer may further include GM-1 ganglioside molecules for binding to a molecule of interest that is connected to cholera toxin subunit for orienting said molecule of interest.

By "T cells specific for an antigen of interest" is meant the T cells expressing receptors for a relevant target of an immune response. As noted above, the specificity of the T cell receptor (TCR) determines which antigens bind to the TCR with sufficient affinity to activate a particular T cell. Optionally, the above outlined method of isolating T cells specific for a particular antigen of interest may include determining the quantity of such T cells that bind to the artificial APC, or may include characterizing the functional phenotype of such T cells. Such method may also include the use of a solid support containing a molecule which is able to recognize and bind to the irrelevant molecule located in the lipid layer of the APC. Such solid support may further be confined to an accessible chamber of a column device.

By "MHC:antigen component" is meant MHC molecules that have affinity for antigens of interest which antigens are associated with such MHC and together form a complex of molecules that are inserted into or are associated with the lipid membrane. Artificial lipid membranes such as liposomes may be prepared in a fashion similar to methods known in the art, (e.g., Watts, et al., *PNAS*, Vol. 81:7564–68; Buus, et ah, *Cell*, Vol. 47; 1071:77 herein incorporated by reference). In a preferred embodiment, the liposome forms a bilayer having eukaryotic cell-like properties in that non-lipid molecules (e.g. MHC: antigen complexes, GM-1 bound to cholera-molecule of interest) may freely migrate within the matrix of the lipid molecules of the liposome's lipid bilayer. An example of a liposome:MHC:antigen combination is provided in FIG. 1 and such a complex may also be prepared, for example, as described in Example 1 below. Moreover, the lipid bilayer may also include accessory molecules such as cholesterol to provide elasticity in the bilayer and GM-1 to provide an anchor for orientation of cholera β subunit comprising molecules of interest.

In one embodiment, a biological sample derived from a tissue sample of interest in the form of a single cell suspension is contacted with an artificial APC followed by incubation of the artificial APC tissue sample mixture with antigen-specific staining compounds (i.e. for example, fluorochrome conjugated antibodies against T cell surface markers of interest e.g., CD3, CD4, or CD8). The cells may also be stained prior to incubation with the complexes. The resulting artificial APC:T cell complex may be separated from the cell suspension by, for example, flow cytometry, capture by a solid support in a column device, or centrifugation of such complexes bound to a solid support such as glass beads or magnetic beads.

Figure 2:
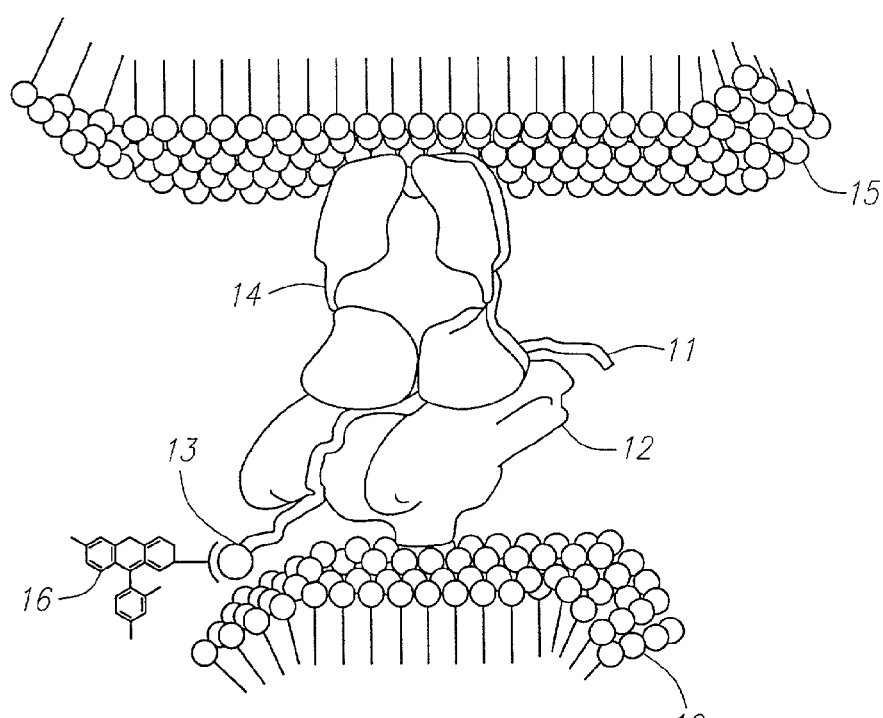
FIG. 2 is a schematic representation of an embodiment of the invention representative of a portion of an artificial APC (10) in which the peptide (11) complexed to the MHC (12) is tagged, wherein the tag, for example, is biotin (13). The visualization of the complex comprising the above components may occur (while a TCR (14) on a T cell (15) is bound to the APC) by FACS through the addition of a streptavidin molecule complexed to a fluorochrome (16).
Figure 3:
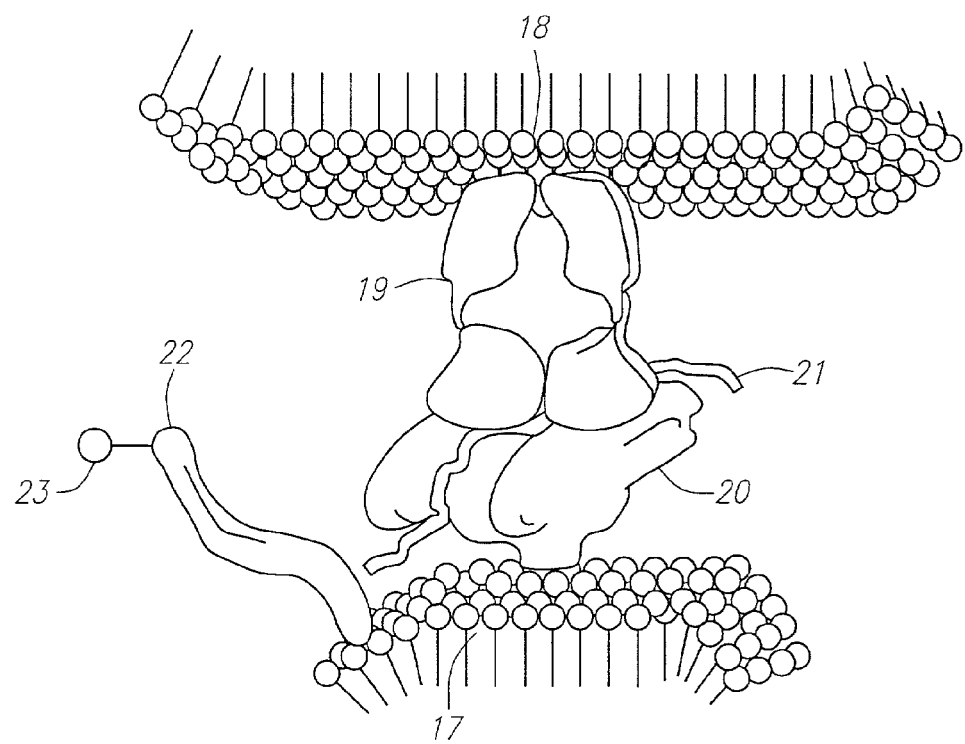
FIG. 3 is a schematic representation of an embodiment of the invention represented by a portion of an artificial APC (17) interacting with a T cell (18) through the TCR (19), using the artificial APC's MHC (20) and unlabeled peptide (21). The visualization by FACS is performed by the inclusion of an irrelevant molecule (22) having an attached label (23). The irrelevant molecule minus the label may also be used to bind the liposome to a solid support.
Figure 4:
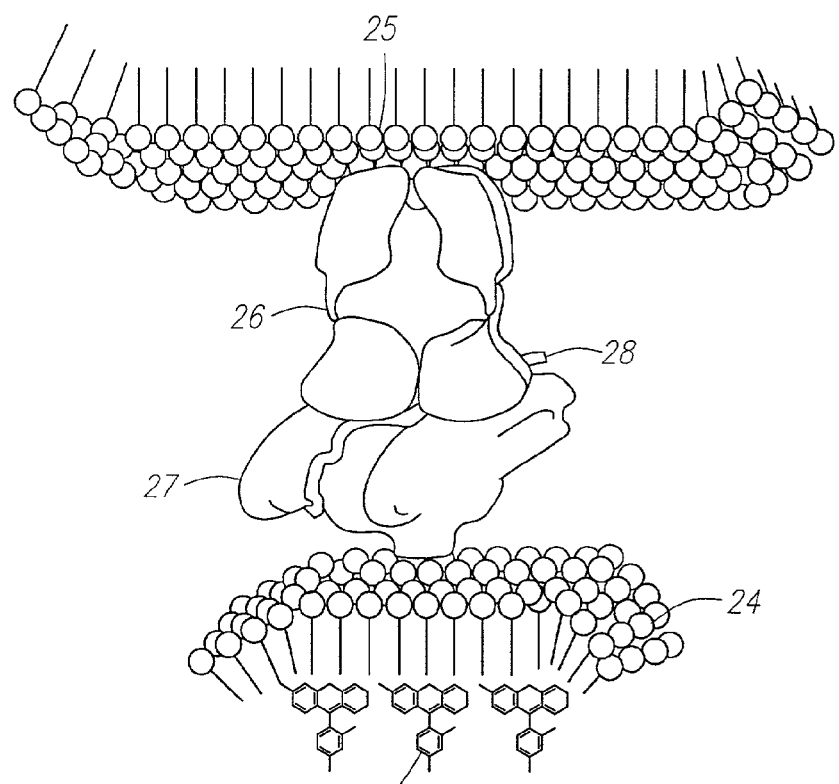
FIG. 4 is a schematic representation of an embodiment of the invention represented by a portion of an artificial APC (24) interacting with a T cell (25) through the TCR (26), using the artificial APCs MHC (27) and unlabeled peptide (28). A fluorochrome (29) may be added to the dialysis buffer during the formation of the liposomes so that visualization may be carried out by FACS.

In one embodiment of the T cell isolation method, the antigen is labeled (FIG. 2). In another embodiment, the irrelevant molecule may be labeled (FIG. 3). In another embodiment of the method, label is associated either covalently or non-covalently with the lipid molecules making up the liposome (FIG. 4). Preferred labels include biotin, fluorochromes such as FITC, radioactive labels and vancomycin. Use of such labels is well understood in the art. In embodiments where the label is associated with lipids of the liposome, the label may be either enclosed within the liposome or incorporated within the lipids of the outer membrane of the liposome. Preferably, the label is a fluorochrome, for example FITC. Such labeled liposomes may be made by mixing FITC with lipids during liposome formation, or may be obtained from commercial sources (e.g., Polar Lipids).

In another embodiment, the present invention provides an alternate method of isolating T cells specific for an antigen of interest. This alternate method comprises:
  (a) contacting an artificial APC comprising MHC antigen: accessory molecule component of interest with a solid support to form a solid support:artificial APC (The liposome of the APC contains a binding molecule i.e., an "irrelevant" binding molecule. The capture molecule that binds to the irrelevant molecule may be bound to said solid support via a linker or may be associated with a phospholipid layer on the solid support). In this embodiment, the antigen binding region of said MHC: antigen component is available for binding to a T cell receptor without steric hindrance because the MHC: antigen component is free to move within the liposome membrane of the APC while the irrelevant binding protein allows the APC to be anchored to the solid support;
  (b) contacting said solid support:artificial APC with a biological sample containing T cells specific for an antigen of interest to form a solid support:artificial APC:T cell complex;
  (c) removing said solid support:artificial APC:T cell complex from said biological sample; and
  (d) separating the T cells specific for said antigen of interest from said complex.

In this embodiment, the T cells are separated by either the physical removal of the T cell bound solid support from the biological sample, or separation may occur by retention of the bound T cells in a solid support containing compartment of a column device.

In another embodiment, the present invention is directed to other alternate methods of isolating T cells specific for an antigen of interest. One such method comprises:
  (a) obtaining a solid support of interest having affinity for non-polar regions of a phospholipid;
  (b) combining the solid support and MHC:antigen complexes, accessory molecules such as LFA-1, and functional molecules (i.e., other accessory molecules, co-stimulatory molecules, modulation molecules, adhesion molecules, and irrelevant molecules) with the phospholipid support to form a solid support associated:membrane-bound:MHC:antigen:accessory molecule:functional molecule complexes (i.e., solid support:phospholipid:MHC:antigen:accessory molecule:functional molecule complex);
  (c) contacting said solid support:phospholipid:MHC:antigen: accessory molecule:functional molecule complex formed in (b) with a biological sample containing T cells specific for an antigen of interest to form a solid support:phospholipid:MHC:antigen:accessory molecule:functional molecule:T cell complex;
  (d) removing said complex formed in (c) from said biological sample; and
  (e) separating the T cells specific for said antigen of interest from said complex.

In this embodiment, the solid support is preferably a glass bead or magnetic bead of about 25 to 300 µm in diameter. Additionally, the MHC, accessory, and functional molecules are not covalently bound directly to the solid support but are noncovalently associated with the lipid layer having the capacity to migrate on the surface of the solid support. Moreover, in a preferred embodiment of this example, the molecule of interest (e.g., MHC, accessory and functional molecules) are connected to cholera toxin β subunit. Further, GM-1 is incorporated into the lipid layer matrix providing a means by which the cholera toxin portion can be bound and the molecule of interest properly oriented in the lipid layer.

In still another aspect, a spheroid solid support may comprise lipid monolayer coating the solid support with only a irrelevant molecule having affinity for bonding another irrelevant molecule located on an APC that either does not have a solid support interior or does have a solid support interior. This aspect adds versatility to the capture process for isolation of APCs that are bound to antigen-specific T cells.

In a further preferred aspect of the invention, kits are provided for the isolation of T cells specific for an antigen of interest comprising any of the following: solid supports, phospholipids, antigen-specific artificial APCs, TCR-specific artificial APCs, solid supports containing lipid associated capture molecules for capturing irrelevant molecules, solid supports containing capture molecules bound to the solid support, buffers, media, labels and column devices.

In another embodiment, the invention contemplates a method of characterizing the functional state of antigen-specific T cells comprising:
  (a) isolating T cells;
  (b) extracting mRNA from said isolated T cells;
  (c) obtaining cDNA corresponding to said extracted mRNA;
  (d) evaluating the mRNA encoding proteins that govern function and phenotype of the antigen-specific T cells wherein the evaluation is carried out by a method selected from the group consisting of (1) mRNA translation of the proteins and testing such proteins using antibodies against the proteins, and (2) rtPCR of the mRNA using primers specific for the proteins.

In this method, the evaluation of the mRNA encoding proteins that govern function and phenotype of the antigen-specific T cell may be used to determine efficacy of an immunomodulation treatment regimen such as the administering of a vaccine. The immunomodulation treatment can comprise inducing tolerance in autoimmunity, reducing allergic response, inducing an immune response against cancer cells. Additionally, the proteins that govern function and phenotype of the antigen-specific T cells include cytokines, chemokines, chemokine receptors, and cytokine receptors.

The genes encoding antigens may also be identified. In another aspect, the invention contemplates a method for identifying a gene which is expressed by a T cell specific for an antigen of interest comprising:
  (a) obtaining a biological sample containing T cells which are specific for an antigen of interest;
  (b) labeling with a first label at least the intracellular gene product of interest produced by T cells in said biological sample;
  (c) preparing a liposome:MHC:antigen complex, wherein the antigen in said liposome:MHC:antigen complex is said antigen of interest;
  (d) contacting the biological sample obtained in step (a), as labeled in accordance with step (b), with the liposome:MHC: antigen complex obtained in step (c) to form a liposome:MHC:antigen:T cell complex;
  (e) labeling with a second label the liposome:MHC: antigen:T cell complex obtained in step (d); and
  (f) discriminating, according to antigen specificity, cells producing the intracellular gene product of interest, which cells have both the first label and the second label.

In such method, the first and said second label may be selected from the group consisting of biotin, a flurochrome, FITC, and a radioactive label; provided that the first and second labels are not the same.

In yet another preferred embodiment, methods are provided for modulating T cell responses. In this embodiment, T cells are isolated from a subject which are specific for an antigen of interest followed by combining said isolated T cells with an artificial APC having functional molecules specific for modulating a T cell. In a preferred embodiment, the T cells specific for an antigen of interest are isolated using any of the T cell isolation methods described herein. In one preferred embodiment, modulation to activate T cells generally is caused by contacting said T cells with an artificial APC that expresses the co-stimulatory molecule B7 or anti-CD28, as well as MHC:antigen.

By "modulating T cell response" is meant the intentional intervention in the functional characteristics of antigen-specific T cells, including, but not limited to, functional pattern of cytokines produced, change in phenotype of T cells, and modulation in the expression of activation markers, cytokines and their receptors and chemokines and their receptors. Such modulations can be carried out for numerous purposes as discussed in the numerous examples above.

The modulation of T cell response may further comprise changing in whole or in part the functional pattern of cytokine production by the isolated T cells specific for a given antigen from a Th1 response to a Th2 response. In a preferred embodiment, modification of a T cell response for the purpose of increasing its Th2 response and/or decreasing its Th1 response includes the expression by the artificial antigen presenting cell used in such method of a co-stimulatory molecule, such as B7-2.

In another embodiment, the modulation of T cell response may comprise changing in whole or in part the functional pattern of cytokine production by said isolated T cells from a Th2 response to a Th1 response. Preferably, modulation of a T cell response for the purpose of increasing its Th1 response and/or decreasing its Th2 response includes the expression by the artificial APC used in such method of a co-stimulatory molecule such as B7-1.

The two subsets of CD4 T cells represented by Th1 and Th2 cytokine markers, have very different functions from one another. These two CD4 T cell subsets can also regulate each other. Once one subset becomes dominant, it is often difficult to shift the response of the T cell (i.e. expression of the cytokine) to the other type. One reason for this is that expressed cytokines of one type of CD4 T cell will inhibit the activation of the T cell to expression of another cytokine. For example, IL-10, a product of Th2 cells, can help to inhibit the development of a Th1 response. Therefore, in one embodiment, IL-10 is incorporated into artificial APCs and the resulting APC may be used to inhibit development of Th1 response.

In another example, interferon-γ (INF γ), a product of Th1 cells, can help to prevent the activation of a Th2 response. If a particular CD4 T cell type is activated preferentially in a response so that the cytokine (Th1 or 2) is highly expressed, such high expression can suppress the development of the other subset. The overall effect of T cell populations expressing one or the other subset is that various tissues become either suppressive (Th2) or inflammatory (Th1). Thus, INF γ can be incorporated into artificial APCs and the resulting APC used to modulate cell populations to become either suppressive or inflammatory.

The ability to manipulate T cell response (as exemplified by the Th1/Th2 subsets) provides a novel method by which treatment can be provided for numerous disease states. For example, a response to an allergen can be manipulated so as to shift the antibody response away from an IgE-dominated response. Such a shift will prevent the allergen from activating IgE-mediated effector pathways. For example, a technique that has been used for many years to generate a desensitization response is carried out by contacting patients with escalating doses of the allergen (such as by feeding, nasal delivery, or by injection). This immunization schedule appears to gradually divert an IgE-dominated response, which diversion is driven by Th2 cells, to one driven by Th1 cells, with the consequent down-regulation of IgE production. Thus, the activation of a Th2 response in such a manner may be of use in the treatment of allergy.

Similarly, other conditions which are associated with a Th2 T cell response, as for example, responses in which the functional phenotype of cytokine secretion is tolerogenic to viral infections and some types of cancer, may also benefit from a modification of the Th2 T cell response so that Th2 is reduced and/or a Th1 T cell response is increased.

Autoimmune conditions, in which the functional phenotype of cytokine secretion is pro-inflammatory (as is the case with Th1), will benefit from a modification of the Th1 T cell response so that it is reduced and/or a Th2 T cell response is increased. As noted above, cytokines are cell-derived soluble mediators associated with immune responses that may act both within a microenvironment and/or systemically. Immune cells secrete specific cytokine profiles, each having markedly different effects. Th2-type cells secrete low levels of TGF β, no IFN γ and high levels of IL-4 and IL-10, the presence of which in turn produce an immunosuppressive or tolerogenic immune environment. Th1-type cells on the other hand secrete very low TGF β, high IFN γ and no IL-4 or IL-10. High expression of INF γ is associated with cell mediated proinflammatory immune environments. As discussed herein, the artificial APC of the current invention can be used to modulate T cell responses by affecting these and other cytokines. Moreover, such cytokines as well as other soluble factors to which a T cell responds may be used in conjunction with a column device as described below.

In yet another embodiment, the regulation of T cell responses may comprise inducing anergy. Specifically, T cell responses may be modified for the purpose of inducing anergy through the Fas/Fas Ligand pathway.

In yet another aspect, the present invention provides methods of treating a condition in a subject who would be benefited by modulating the functional patterns of cytokine production by certain of such subject's antigen-specific T cells to increase Th2 response and/or decrease Th1 response, comprising:

(a) isolating T cells capable of triggering a Th1 response from a subject;

combining said isolated T cells with artificial APCs which express MHC capable of binding an antigen recognized by said T cells wherein said artificial APC also expresses the co-stimulatory molecule B7-2;

(c) separating T cells that have bound to said artificial APCs in step (b); and (d) administering said T cells isolated in step (c) to said subject.

T cells that have been in contact with an artificial APC as described above will be stimulated to shift their Th1 response to a Th2 response. Conditions which would be benefited by modulating the functional pattern of cytokine production to increase Th2 response and/or decrease Th1 response include autoimmune diseases such as, for example, type 1 diabetes mellitus, multiple sclerosis, rheumatoid arthritis, dermatomiosytis, juvenile rheumatoid arthritis and uveitis.

In yet another aspect, the present invention provides methods of treating a condition in a subject that would be benefited by altering the functional pattern of cytokine production by certain antigen-specific T cells to increase Th1 response and/or decrease Th2 response comprising:

(a) isolating T cells that are specific for an antigen capable of triggering a Th2 response from a subject;

(b) combining said isolated T cells with an artificial APC which expresses an MHC capable of binding an antigen that is recognized by said T cells so that the functional pattern of said T cells may be modulated, wherein said artificial APC also expresses the co-stimulatory molecule B7-1;

(c) separating the T cells modulated in step (b); and (d) administering said T cells isolated in step (c) to said subject.

Conditions which would be benefited by modulating the functional pattern of cytokine production to increase Th1 response and/or decrease Th2 response include for example, allergy, allergy to dust, animal skin bypass products, vegetables, fruits, pollen, chemicals, and some infections (e.g., viral, fungal, protozoan and bacterial).

As noted above, the present invention provides methods for isolating antigen-specific T cells. It is desirable to isolate antigen-specific T cells in a variety of contexts. For example, in adoptive immunotherapy, lymphocytes are removed from a patient, expanded ex vivo, and then reinfused back into the patient to augment the patient's immune response. See Rosenberg et al., *N. Engl. J. Med.* 313:1485–1492 (1985); U.S. Pat. No. 4,690,915. This approach has been effective in the treatment of various cancers (see, e.g., Rosenberg et al., *N. Engl J. Med.* 319:1676–1680 (1988). Isolation and expansion of T cells specific for a particular antigen will increase the specificity and effectiveness of adoptive immunotherapeutic approaches. Such expansion may be benefited by obtaining a population of monoclonal T cells. Thus, the invention contemplates a method of obtaining a monoclonal population of T cells specific for an antigen of interest comprising:

(a) isolating T cells specific for an antigen of interest; and (b) culturing the isolated T cells in an individual well with the antigen of interest and an artificial APC.

Isolated T cells specific for a particular antigen may also be used as a diagnostic to screen for the presence of, or amount of a particular antigen and thus detect the presence, absence, or status of an immune response. Early detection of an immune response will facilitate selection of a particular treatment regimen in a variety of pathological conditions such as autoimmune diseases, allergies, allograft rejection, and infectious diseases. In a diagnosis of this type, the isolated T cells are used both as a means of detection and as reporters. The T cells proliferate when contacted with the antigen for which they are specific. This proliferation is easily detected as an increase in cell number or as an increase in growth rate measured, for example, by the rate of uptake of a label (e.g., observation of the uptake of tritiated thymidine or bromodeoxyuricyl (BrdU)). Thus, the presence or absence of target antigen can be detected by exposing the isolated T cells to a tissue sample (e.g., peripheral blood) and monitoring their proliferation rate. In the current invention, a preferred embodiment includes the observation of bound T cells using a FACS which allows the avoidance of time consuming proliferation experiments.

Isolation of antigen-specific T cells also provides a homogenous source of T cell receptors. A homogenous source of T cell receptors is an aid to the elucidation of structure-function relationships of particular receptors. A homogenous source of T cell receptors also facilitates the development of solubilized T cell receptors that are of use in a number of therapeutic applications (See, e.g., U.S. Pat. No. 5,283,058). In the current invention, solubilized receptors may be used in conjunction with an immunomodulation column device.

In another preferred embodiment, the invention provides for a method of identifying epitopes expressed on the MHC that are of import to acceptance or rejection of grafts in transplantation therapy. In this embodiment, a donor's MHC is examined by computer modeling to identify peptide moieties likely to be recognized by a recipient's T cells. The recipient's T cells are tested by FACS analysis for binding against the peptides. Upon positively identifying reactive peptides, such peptides may then be used to deplete the recipient's graft rejecting T cells thereby modulating the recipient's immune response in the transplantation regimen. This modulation is carried out within a comprehensive treatment that includes further modulating the recipient's sensitivity to the graft epitopes by exposing the recipient to the donor's epitopes by feeding, nasal delivery, or injection of increasing concentrations of the peptides.

In another aspect, the invention provides for a method to identify antigenic motifs of pathogens that are recognized by the MHC. In this embodiment the identification of such motifs allows the development of anti-pathogen vaccines comprising either pools of such motifs in the form of peptides that are recognized by T cells in the general human population i.e., the pathogen's antigenic moieties responsible for generating immune responses are identified so that for any disease, a vaccine comprising such antigens may be produced. Additionally, a vaccine may be produced against such antigenic moieties comprising a population of a patient's pathogen-specific T cells that have been expanded ex vivo.

Figure 6:
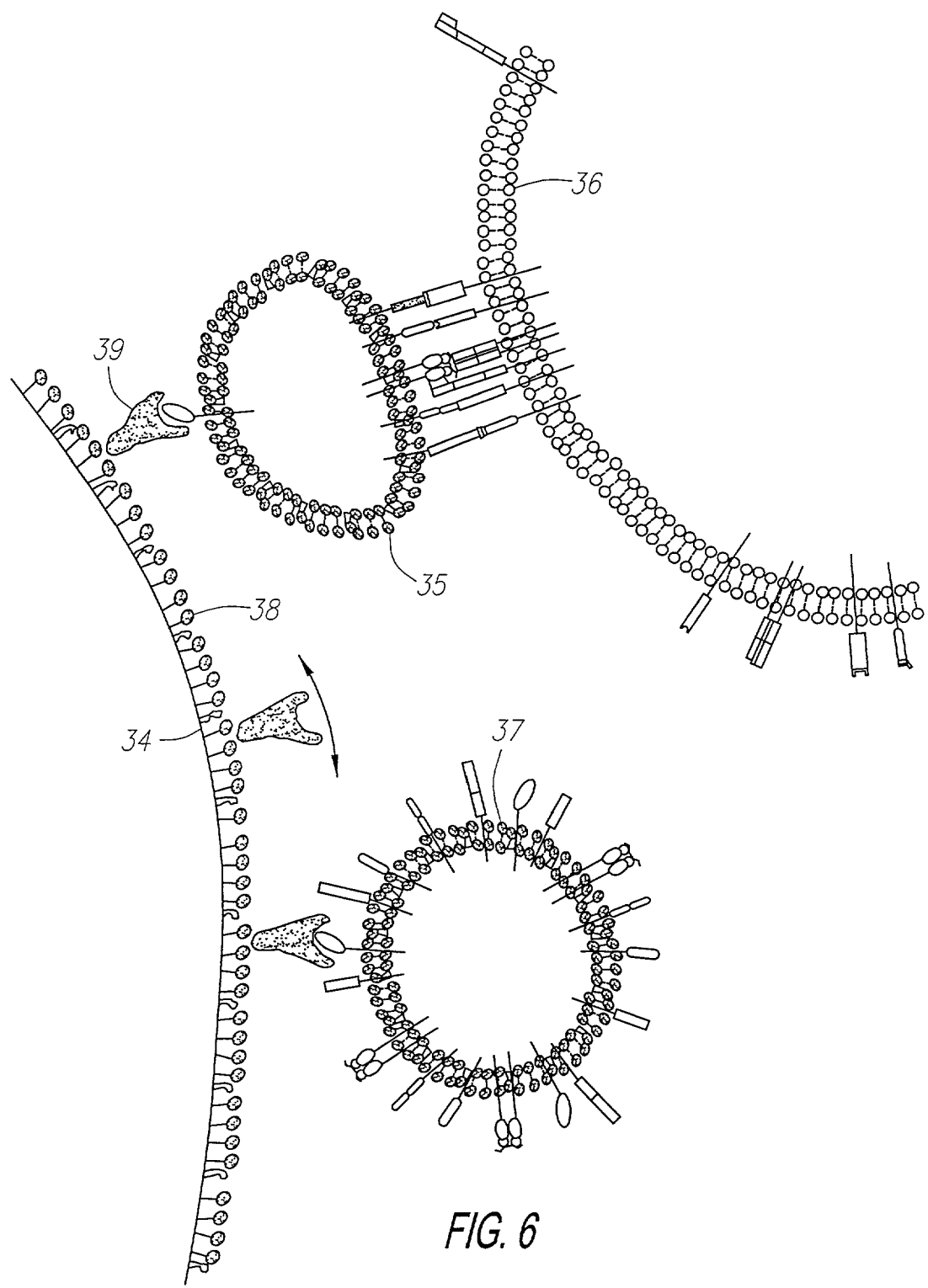
FIG. 6 is a schematic showing the capture of artificial APCs (35) and (37) by capture molecules (39) which are noncovalently associated with a lipid layer (38) (e.g., a neutral phospholipid) attached to a solid support (34).
Figure 7A:
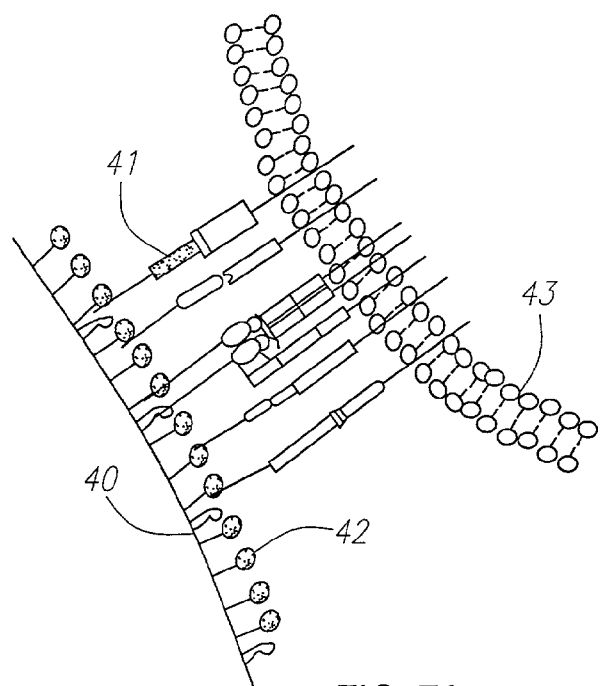
FIG. 7a represents a solid support (40) having a non-covalently associated lipid layer (42) containing various components; of artificial APCs (41) that bind a T-cell (43).
Figure 7B:
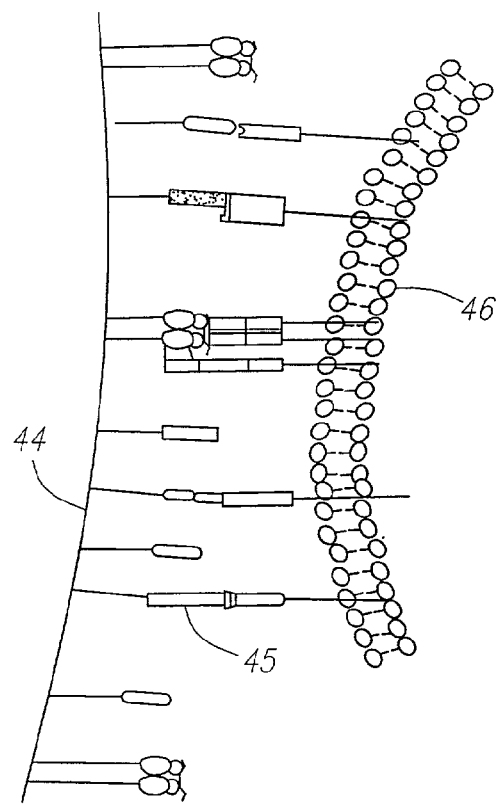
FIG. 7b shows a solid support (44) having the various components of artificial APCs (45) without a lipid component that can bind to a T cell (46).
Figure 8:
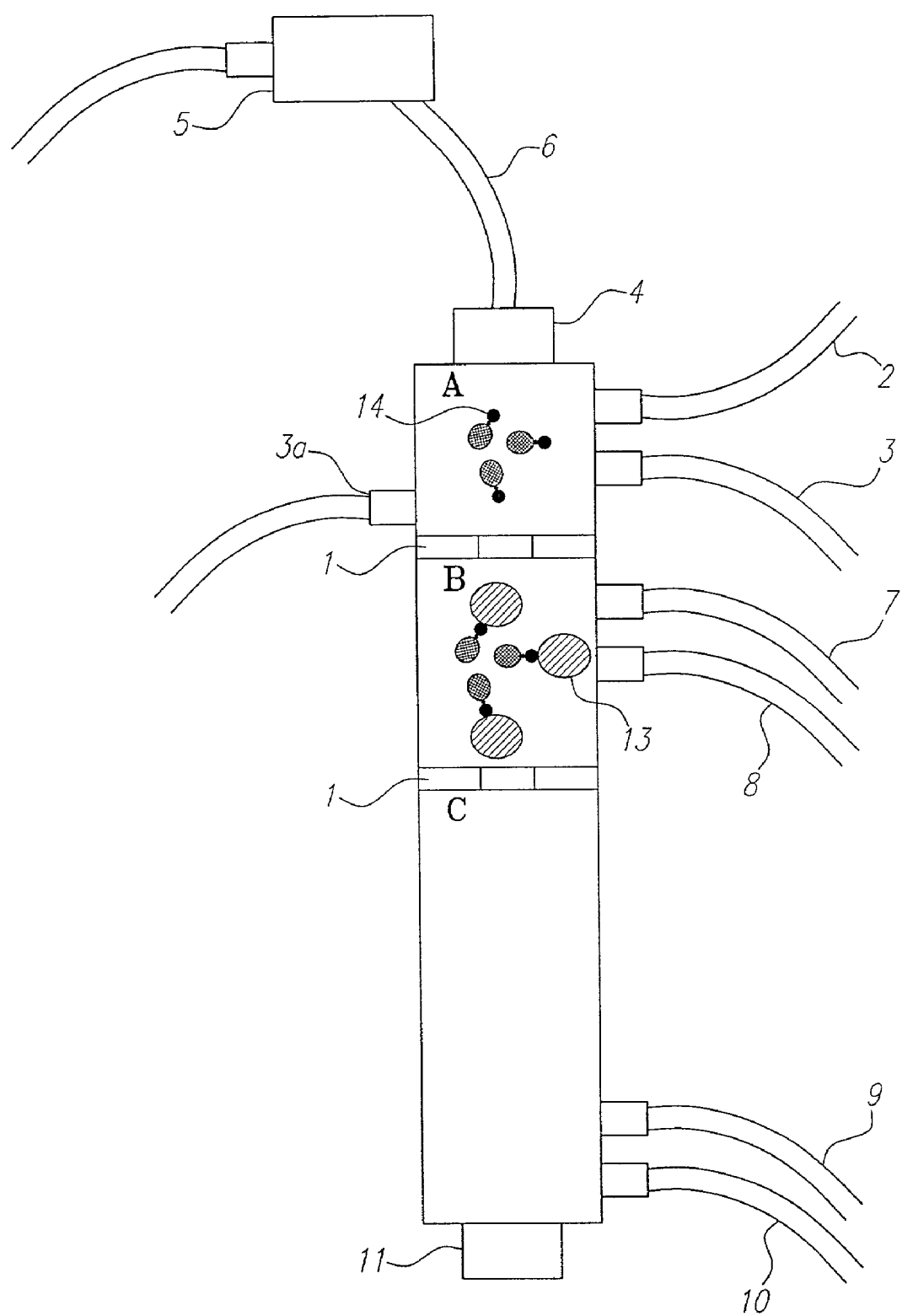
FIG. 8 shows a column device having a multiplicity of compartments for processing antigen-specific T cells. The column, as shown, also contains APCs and various embodiments of solid supports.

In yet another aspect of the invention, a column device is provided comprising a multiplicity of compartments that are arranged in series. As shown in FIG. 8, one embodiment of such device has compartments A, B, and C. Each compartment is contiguous with the adjacent compartment by a valve 1. The valve between each compartment may be opened or closed. Compartment A also has entrance ports 2 and exit ports 3 for receiving a flowable medium. Any of the compartments may contain solid supports as seen in FIGS. 6, and 7 for binding either a molecule that can bind to an irrelevant molecule for immobilizing an artificial APC, or for binding directly MHC:antigen:functional molecule complexes. The entrance port 4 of compartment A is attached to an external device 5 (e.g., a device where a patient's T cells are separated from whole blood and concentrated) prior to export through a sterile tube 6 to entrance port 4. Once the patient's enriched T cell population is transported into compartment A via entrance port 4, the T cells containing TCR specific for the MHC:antigen complexes bind to MHC:antigen complexes that are themselves attached either directly to the solid supports or are associated with an artificial APC which is bound to a solid support via an irrelevant molecule. In the configuration demonstrated in FIG. 8, artificial APCs 14 are attached to solid supports in compartment β awaiting interaction with incoming cell through entrance port 4. Compartment A thus provides a chamber wherein the APCs and cells can interact so that antigen-specific T cells can be isolated while non-binding T cells are allowed to wash out of the compartment A via exit port 3a. After the non-binding cells are removed (and either discarded or returned to the patient's circulatory system, or addressed to a device for monitoring the cells such as a FACS), the bound antigen-specific T cells may be released from the solid supports in A and allowed to channel or flow through valve 1 located between compartment A and B and into compartment B. The artificial APC-cell bound complexes or just the antigen-specific T cells alone may be released from solid support of compartment A by adjusting the temperature of the medium in the compartment A. Once the antigen-specific T cells are in compartment B, they may again be captured as shown in FIG. 8, or simply be treated without recapture in any number of ways to induce cell modulation. For example, artificial APCs containing antigen-specific MHC:antigen:functional molecule complexes may be infused into compartment B via entrance port 7. With the infusion of the antigen-specific APCs into compartment B, the antigen-specific T cells may then bind and be induced to modulate their respective response or be acted upon otherwise as desired. FIG. 8 shows T cells 13 that have been released from compartment A and are shown bound to APCs that are in turn bound to solid supports. As described above, and hereinafter, numerous types of modulation of the T cells may occur. For example the T cells may be modulated to (1) increase a Th 1 and/or decrease a Th2 response, (2) increase a Th2 and/or decrease and Th1 response, (3) be generally induced to proliferate regardless of Th1 or Th2 response, (4) enter a state of anergy, (5) become apoptotic, (6) shed certain adhesion molecules known to those skilled in the art to be involved in the entry of cells into specific diseased areas, (7) upregulate/downregulate chemokine or cytokine receptors associated with a Th1-type response, (8) upregulate/downregulate chemokine or cytokine receptors associated with a Th2-type response. The T cells may also be captured on such APCs for the purpose of (1) depleting allo-antigen-specific T cells from a donor's T cell population in transplantation oriented therapy, such as bone marrow transplant therapy or (2) from a patient's T cell population such as to facilitate a graft of allogenic solid organs, or (3) used in identifying TCRs that bind to pathogen-recognizing MHCs or self-derived pathogen-mimic antigenic motifs. Moreover, soluble molecules may be added to the device for inducing such modulation including cytokines, adjuvants, and hormones.

Once isolation or other modulation has been performed in compartment B, the T cell:artificial APC complex may be addressed to compartment C via the valve 1 between compartments B and C. The entrance port 7 of compartment B may be additionally connected to external units for supplying buffers and the like that may be necessary for carrying out manipulations of the T cells in compartment B. The exit port 8 of compartment B may also be used to transport modulated T cell:artificial APC complexes to sampling devices such as FACS or to other devices for such things as cell proliferation and the like.

Compartment C may also contain solid supports and the like for binding artificial APC:T cell complexes and further treatment. In compartment C, the modulated and isolated T cells may be eluted from the APCs (via the adjustment of the medium's temperature) and addressed to other devices through ports 9 and 10, or addressed out of the column through exit port 11 to, for example, the patient, a FACS, a culture device, or to another location for further manipulation.

Specific embodiments of the present invention are exemplified in the following Examples. These Examples are not to be interpreted as limiting the scope of the invention in any way, the scope being disclosed in the entire specification and claims.

EXAMPLE 1

Liposome Assay for Detection of Antigen-Specific T Cells

In this example, experiments are described which demonstrate the capacity of T cells to bind to liposomes containing cholesterol having MHC:antigen complexes inserted into the liposome membrane. The capacity of T cell binding was quantified by flow cytometry analysis (FACS). Negative controls for the binding include the use of a control T cell line (i.e., non-reactive) having specificity for an irrelevant peptide, incorrect MHC restriction, peptide and antibody inhibitions, limiting dilutions, and the use of MHC without peptide.

The ability of the method to provide for discrimination between antigen-specific T cells was facilitated by use of two T cell hybridomas specific for the same peptide. These hybridomas were $OVA^{323-336}$ (which correspond to residues 323–326 of ovalbumin) (obtained from Research Genetics, Huntsville Ala.) which were restricted by two different MHCs, $I-A^S$ and $I-A^d$. Specifically, the designations for the restrictions were $I-A^S$ restricted $OVA^{323-336}$ specific T cell hybridoma, AG111.207, and the $I-A^d$ restricted $OVA^{323-336}$ specific T cell hybridoma 8D051.15. A peptide containing 2 identities and one conservative substitution, Hi 15 (Research Genetics), which corresponds to residues 15–31 of *H. influenzae* isoleucyl tRNA transferase, was used as a negative control.

Materials and Methods

Preparation of Liposome:MHC:Antigen Complexes.

Liposomes were prepared similarly to that described by Brian et al, *PNAS,* 81:6159–63. Briefly, cholesterol (Ch) and L-α-phosphotidylcholine (PC) (Sigma) were mixed at a molar ratio of 2:7 of Ch and PC, respectively. The mixture was placed under an argon stream for 30 minutes to evaporate chloroform used in the preparation, and resuspended in 140 mM NaCl, 10 mM Tris HCl, and 0.5% deoxycholate at pH 8. The suspension was sonicated for three minutes or until clear.

Complexes of affinity-purified MHC molecules $I-A^S$ and $I-A^d$ (each expressed in a B cell lymphoma and purified via immunoaffinity column) were inserted into liposomes by a 72 hour 4° C. dialysis against three changes of PBS (Slidalyzer, Pierce) at a 1:10 molar ratio of MHC to liposomes to form liposome:MHC complexes.

The $OVA^{323-326}$ peptide and the control peptide, Hi 15, were biotinylated, (post synthesis, Sigma), and the biotinylated peptides (b-peptides) were incubated with the liposome:MHC complexes for 18 hours at room temperature at a physiologic pH to form liposome:MHC:b-peptide complexes.

Flow Cytometry.

Viable cells were separated from debris using a ficolhypaque gradient. (Lymphocyte M) Cells were blocked with 10% PCS in PBS for 10 minutes on ice, then washed in PBS. Incubations with antibodies (used at concentrations of 400–600 ng/ml) were performed on ice in the dark for 20 minutes. The antibodies used included anti-CD3e (clone 145-2C11), anti-CD4 (clone GK 1.5), anti-CD8a (clone 53-6.7), anti-HSA (clone M1/69), and anti-CD69 (H1.2F3) (Pharmingen, San Diego, Calif.). Liposome:MHC:b-peptide complexes were preincubated with fluorescent streptavidin molecule (f-strep) at room temperature for ½ hour. When two peptides were used in the same assay, the liposome: MHC:b-peptide complex was preincubated with streptavidin molecules of differing fluorescence prior to addition to cells. Sorted cells were either (a) cultured (using a 3:1 ratio of irradiated BALB/c spleen cells, 20 U/ml rIL-2, 10 µg/ml Hi 15 or Iα52, 10% FCS, 1% Penicillin/Streptomycin/ Glutamine (P/S/G), in RPMI 1640 at 37° C. and 6% $CO_2$), (b) processed for variable beta chain (Vb) analysis by PCR, or (c) reanalyzed by a fluorescent antibody cell sorter (FACS).

Yields ranged from 2,000 to 16,000 events. Bulk-sorted cells used for reanalysis were incubated for ½ hour on ice and spun down through 100% FCS at 325xg for 10 minutes to remove liposome:MHC:b-peptide complexes, prior to restaining with liposome:MHC and a different b-peptide. Single-cell sorts were dispersed in 96-well culture plates containing fresh irradiated APCs obtained from the spleen of a syngeneic BALB/c mouse. Generally 8–12 wells showed proliferation over six weeks. Cells were visualized with a Becton Dickinson FACS Star equipped with LYSIS II software.

Figure 9A:
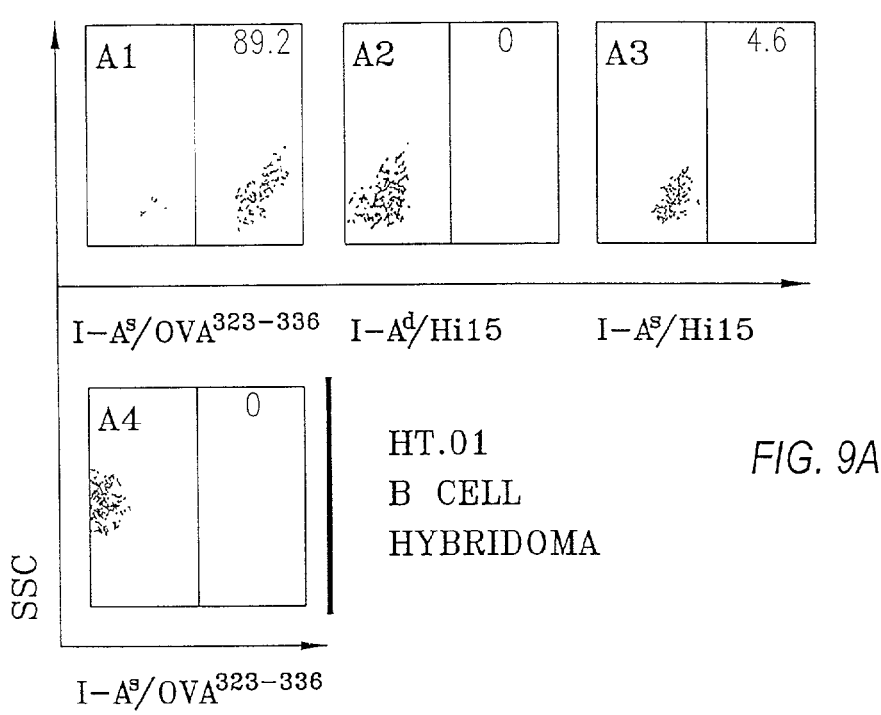
FIGS. 9A and B is a series of FACS figures detailing the specificity of the embodiment of the method diagramed in FIG. 2 using two different murine hybridomas specific for the OVA peptide in the context of either I-$A^d$ or I-$A^S$. The Hi 15 peptide has two identities and one conservative substitution with the OVA peptide, thus being a stringent control of specificity.
Figure 9B:
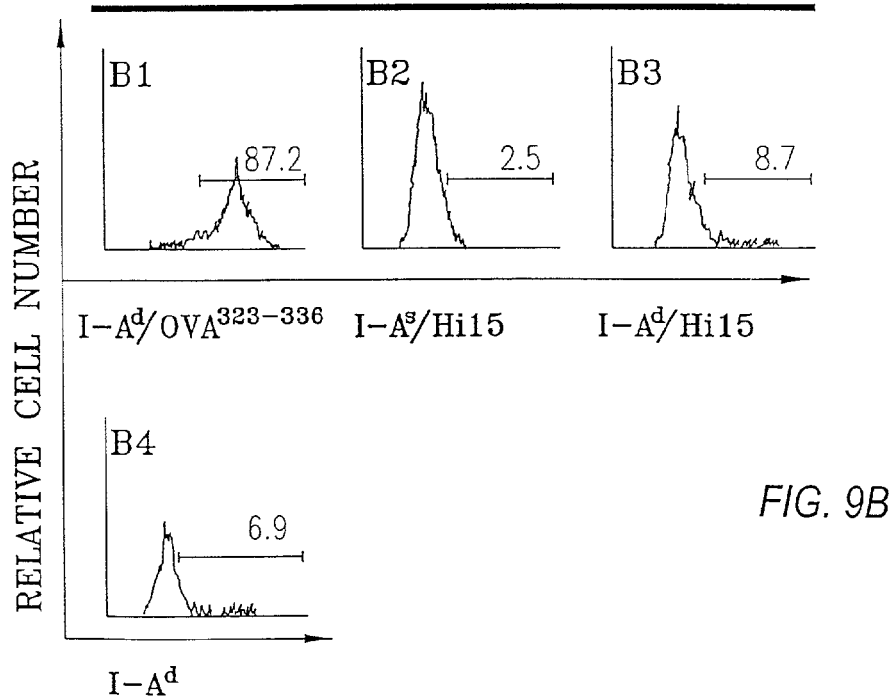

As shown in FIG. 9, specific recognition of MHC/peptide complexes by T—T hybridomas AG111.207 (I-$A^s$/$OVA^{323-336}$ specific) and 8D051.15 ($IA^d$/$OVA^{323-336}$ specific) were observed. Cultured AG111.207 or 8D051.15 cells were analyzed by flow cytometry using anti-CD4 antibodies and I-$A^d$% b-peptide or $IA^s$/b-peptide combinations complexed into liposomes and visualized by addition of f-strep. The ratio of cells specific to either the I-$A^d$/antigen or $A^s$/antigen was constant between experiments. (All figures are gated on CD4+ cells unless otherwise stated.) FIG. 9(a) shows AG111.207 cells which were stained with anti-CD4 antibody and differing combinations of MHC/antigen including an irrelevant peptide known to bind to I-$A^d$ (Hi 15). Cellular specificity is shown by use of a B cell hybridoma (FIG. 9-a4). FIG. 9(b) shows 8D051.15 cells which were analyzed with differing combinations of MHC:antigen. Included is a control using biotinylated I-$A^d$ alone to detect the T cell hybridoma (FIG. 9-b4).

Results

In the series of experiments for which results are shown in FIG. 9, purified I-$A^S$ or I-$A^d$ MHCs were inserted into liposomes and then complexed to the biotinylated $OVA^{323-336}$ peptide. These complexes were incubated with streptavidin-FITC, and then with a standard amount of AG111.207 or 8D051.15 cells (final MHC concentration of 66 µg/ml). When analyzed by flow cytometry, nearly 90% of the AG111.207 (FIG. 9a1) and 87.2% of 8D051.15 (FIG. 9b1) cells stained positive when using the correct restriction and peptide.

The specificity of the entire interaction was demonstrated by lack of staining of AG 111.207 and 8D051.15 cells when incubated with anti-CD4 Ab and complexes of the incorrect restriction for each hybridoma, I-$A^d$ and I-$A^S$ respectively, and Hi 15 which has two identities (p2, p10) and one conservative substitution (p5) with $OVA^{323-336}$ (0% positive cells FIG. 9a2; 2.5% positive cells, FIG. 9b2). The peptide specificity of the interaction was demonstrated when AG111.207 and 8D051.15 cells were incubated with anti-CD4 antibody, the correct restriction element, but irrelevant peptide for each hybridoma, I-$A^s$/b-Hi15 or I-$A^d$/b-Hi15, respectively (4.6% positive cells, FIG. 9a3; 8.7% positive cells, FIG. 9b3). The binding between MHC:b-peptide complexes and AG 111.207 T cells was also concentration dependent. Only 13.1% of AG 111.207 cells tested positive when the I-$A^s$$OVA^{323-336}$ concentration in the assay was reduced five fold to 13 µg/ml (not shown). The signal was also reduced by the addition of 300 µg/ml of the same, non-biotinylated $OVA^{323-336}$ peptide as a competitive inhibitor during preparation of the I-$A^s$/OVA complexes (5.1% of CD4+ cells positive, not shown). This finding suggests that biotinylation of the peptide does not interfere with the trimolecular interactions among peptide, MHC and TCR. Moreover, this assay was seen to be dependent on both TCR and MHC:peptide complexes, insofar as binding can be inhibited by simultaneous addition of anti-TCR and anti-I-A antibodies (6.9% of CD4+ cells positive). As shown in FIG. 9a4, no binding to TCR-negative cells, such as B cell hybridoma HT.01, was detected (0% of cells positive). Using biotinylated I-$A^d$ in liposomes without peptide, 6.9% of 8D051.15 cells bound the MHC alone (FIG. 9b4). Hence, the interaction requires the presence of the specific peptide.

Figure 15:
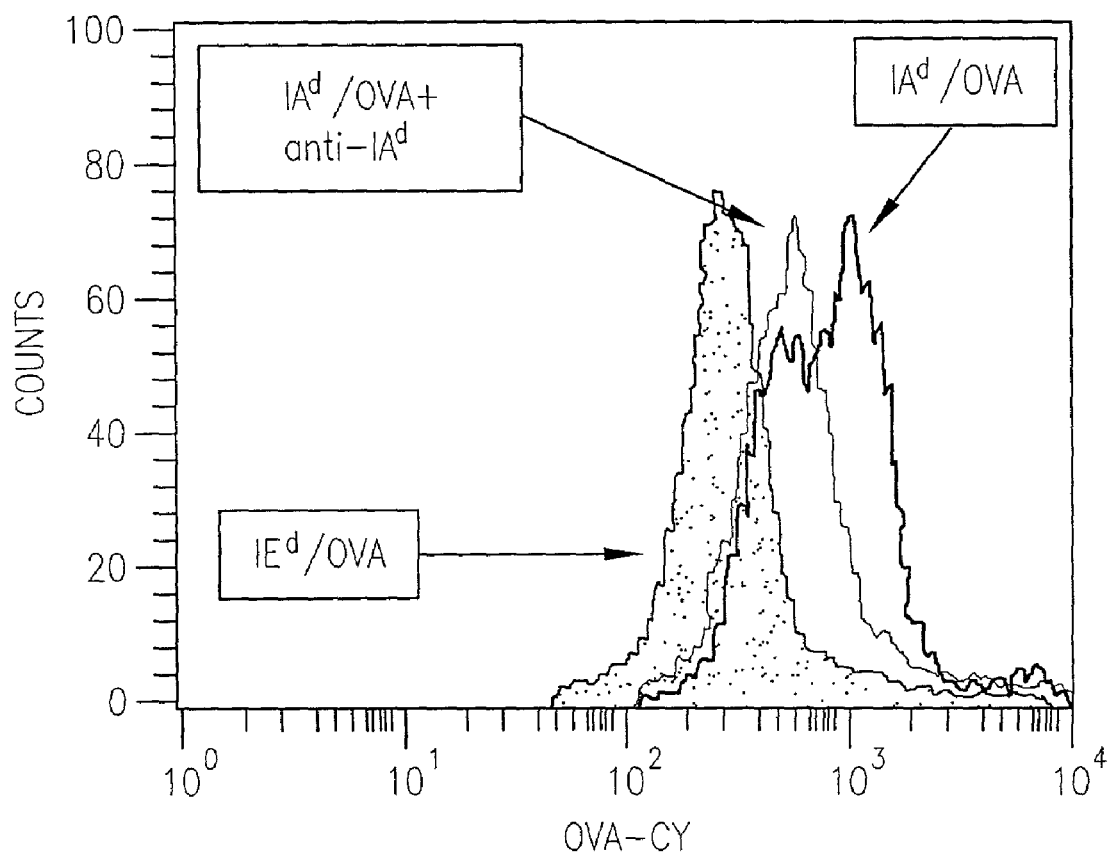
FIG. 15 shows the identification of antigen specific cells with T cell capture in a monoclonal TCR population wherein $OVA^{323-339}/IA^d$ specific T cell hybridoma 8DO cells were incubated with artificial APCs complexed with $IA^d$ and biotinylated $OVA^{323-339}$. Prior to the incubation, the hybridoma cells were stained with CD4 PE (phycoerithrin, i.e., a fluorochrome) and the artificial APCs, complexed with $IA^d$ and biotinylated $OVA^{323-339}$, were stained with streptavidin labeled with CY. As control for specificity of the binding, T cells of the same hybridoma were incubated with liposomes complexed with $IE^d$ and biotinylated $OVA^{323-339}$. Binding of hybridoma T cells to artificial APCs could be inhibited by co-incubation with monoclonal anti-$IA^d$ antibody. The histograms show the intensity for staining for streptavidin CY in CD4 gated hybridoma cells. Gates were set on irrelevant isotype controls for CD4, and on binding of cychrome-conjugated streptavidin to T cells/artificial APC with unbiotinylated $OVA^{323-339}$ peptide.
Figure 17A:
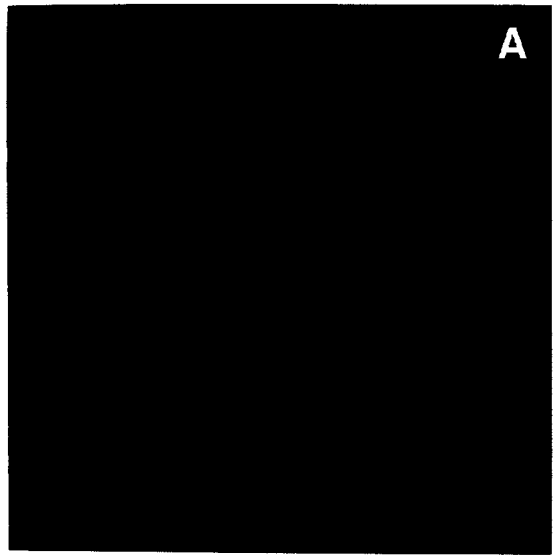
FIGS. 17A–D shows 8DO cells incubated for 20 minutes with artificial APCs expressing $IA^d/OVA^{323-339}$ complexes. Artificial APCs were stained with Alexa568 anti MHC (red) (i.e., the MHC is labeled red), and FITC cholera toxin (green) (i.e., the cholera toxin bound to the T cell receptor is labeled green). Thus.
Figure 17B:
Figure 17C:
Figure 17D:
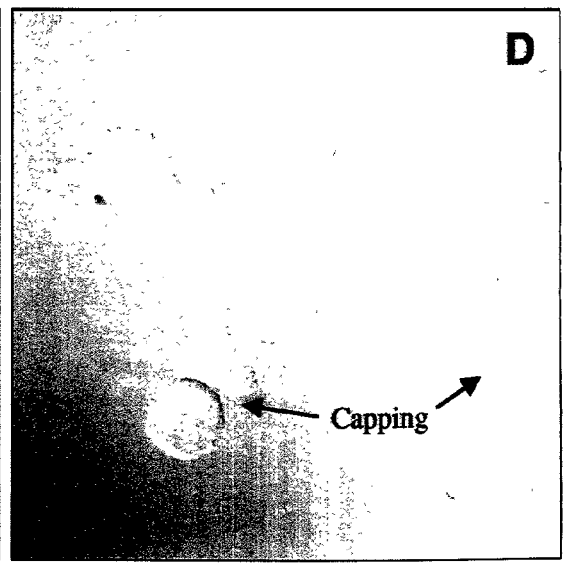
Figure 18A:
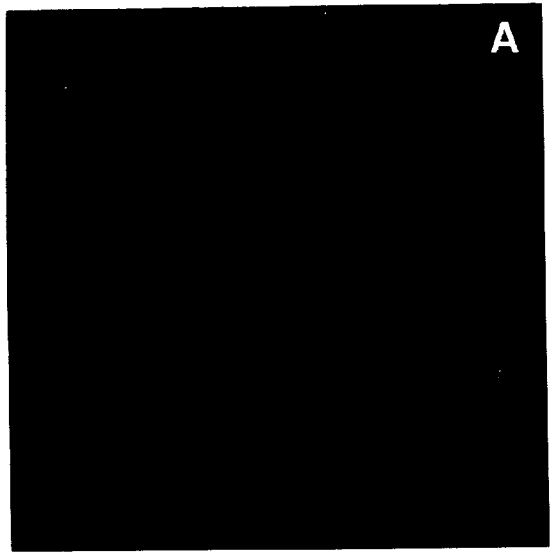
FIGS. 18A–D shows 8DO cells incubated for 20 minutes with artificial APCs expressing $IA^d/OVA^{323-339}$ complexes. Artificial APCs lipid membranes were labeled using FITC (green). The T cell receptor were labeled with Alexa568 anti CDS (red). Thus, FIGS. 18A–D further confirms the data shown in FIGS. 17A–D.
Figure 18B:
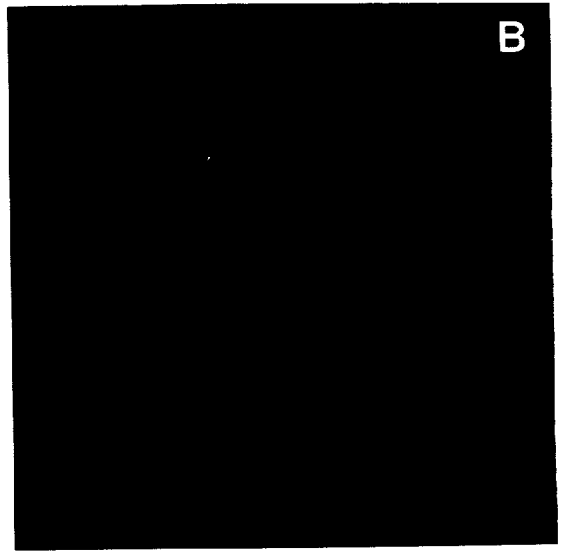
Figure 18C:
Figure 18D:
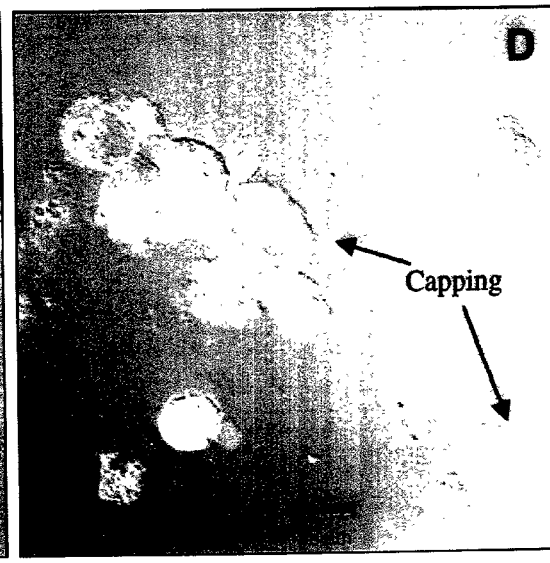

Artificial APCs Identify T Cell Hybridoma 8DO Specific for $IA^d$/OVA Combination In another experiment we evaluated the capability of artificial APC, presenting synthetic biotynilated peptide OVA in the context of IA d, to visualize by FACS analysis hybridoma 8D0, which is OVA/$IA^d$ specific. As shown in FIG. 15, the percentage of hybridoma cells was visualized by binding with cychrome-tagged artificial APC. This interaction was specific, insofar as TCR binding was dependent on the availability of the MHC/peptide complexes. The interaction was inhibitable by addition of antibodies interfering with such interaction (% positive cells, FIG. 15 middle graph), and 8D0 hybridoma cells did not bind to the artificial APC presenting the correct peptide in the context of $IE^d$ (% positive cells, FIG. 15 left graph). The result indicates that highly specific and sensitive interaction occurs between T cells and artificial APCs. Moreover, addition of competitive inhibitors in reducing the specific binding proves that the labeling of this method does not interfere with the APC/T cell interaction.

EXAMPLE 2

Identification of Antigen Specific T Cells in Mouse Embrionic Thymuses

In this example, a murine model is used to investigate the effects of a naturally processed self-peptide on the maintenance and proliferation of T cells which may cross-react with homologous peptides of exogenous origin, all performed in a non-transgenic system. The example emphasizes the fact that without a method such as that of the current invention to capture T cells, it is not possible to evaluate polyclonal antigen specific chimeric T cell selection in a non-transgenic system. This is because conventional methods that examine cytokine presence or cell proliferation cannot identify cells specific for relevant antigen.

The self-peptide I α 52 (ASFEAQGALANIAVDKA) (Seq. Id. No. 1), used in these experiments corresponds to residues 52 to 68 of the α chain of the I-E molecule. It represents one of the most abundant peptides naturally processed and presented in the context of I-$A^d$ (Hunt et al., Science, Vol. 256:1817–20; 1992; Rudensky et al., Nature, Vol. 353:622–27; 1991). These experiments demonstrate that T cells specific for a particular antigen can be identified from a polymorphic population of cells. In addition, functional and genetic characteristics of the cell population were demonstrated (Table 1).

TABLE I

Phenotypic and Functional Characteristics of Thymocytes Before and After Fetal Thymic Organ Culture

| | Day 16 of Gestation | Day 6 of FTOC | Day 6 of FTOC+ $10^{-2}$ mM Iα52 |
|---|---|---|---|
| CD3$^{lo}$CD4$^+$CD8$^+$ | 6% | 1.3% | 1.1% |
| CD3$^{lo}$HSA$^{hi}$ | 99 | 3.9 | 4.1 |
| CD3$^{lo}$CD69$^+$ | 2 | <1 | <1 |
| CD3$^{hi}$ CD4+CD8+ | <1 | 47 | 34 |
| CD3$^{hi}$HSA$^{hi}$ | <1 | 82 | 84 |
| CD3$^{hi}$CD69$^+$ | <1 | 10 | 11 |
| Cell Number | N/D | 1.55 × 10$^{5\#}$ | 1.65 × 10$^{5\#}$ |
| Iα52 Stimulation Index | N/D | 0.5 × $^+$/−0.1 | 6.2 × $^+$/−2.7 |
| Hi15 Stimulation Index | N/D | 0.1 × $^+$/−0.06 | 2.5 × $^+$/−1.1 |

BALB/c embryonic thymus lobes were made into single cell suspensions, and analyzed by flow cytometry.
Cell numbers are an average of eight to ten thymus lobes from FTOC.
Data in the table represent between two and four experiments.
Standard deviations are 3.1 × 10$^4$ and 1.5 × 10$^4$ respectively.

BALB/c embryonic thymus lobes were made into single cell suspensions, and analyzed by flow cytometry. Cell numbers are an average of eight to ten thymus lobes from FTOC. Data in the table represent between two and four experiments. #Standard deviations are 3.1×10$^4$ and 1.5×10$^4$ respectively.

Materials and Methods

Antigens.

The I-A$^d$-derived peptide Iα52 (ASFEAQGALANIA-VDKA) (Seq. Id. No. 1) was synthesized (Research Genetics) using standard solid phase peptide synthesis method. Peptides used for flow cytometry were biotinylated (b-peptides) using a kit (Sigma) and were separated from free biotin by HPLC.

Generation of Lymphocytes from Fetal Thymic Organ Cultures (FTOC).

BALB/c embryonic thymi were harvested day 16 of gestation and placed onto 0.4 μm cell culture inserts (Fisher) in six-well plates containing RPMI 1640, 10% FCS, 1% P/S/G, with or without Iα52 ($10^{-1}$ mM to $10^{-10}$ mM), at 37° C. and 6% CO$_2$ for six days. Cells were dissociated with a glass grinder (Kontes). Cell recovery was between 1.0×10$^5$ and 2.8×10$^5$ cells/lobe. Post-FTOC cultures were performed using a 3:1 ratio of irradiated BALB/c spleen cells, 20 U/ml rIL-2, 10 μg/ml Hi 15 or Iα52, 10% FCS, 1% P/S/G, in RPMI 1640 at 37° C. and 6% CO$_2$.

Preparation of Liposome:MHC:Antigen Complexes.

Liposomes were prepared as described in Example 1.

Flow Cytometry.

Flow cytometry was performed as described in Example 1.

Results

It has been shown previously that different concentrations of the same peptide have strong implications for T cell selection (see Sebzda et al., Science, Vol. 263:1615–18). We confirmed this phenomenon using various concentrations of Iα52 peptide to demonstrate its influence upon peptide-mediated positive selection and to define, directly, the antigen specificity of a positively selected T cell population in a non-transgenic BALB/c model.

Figure 10A:
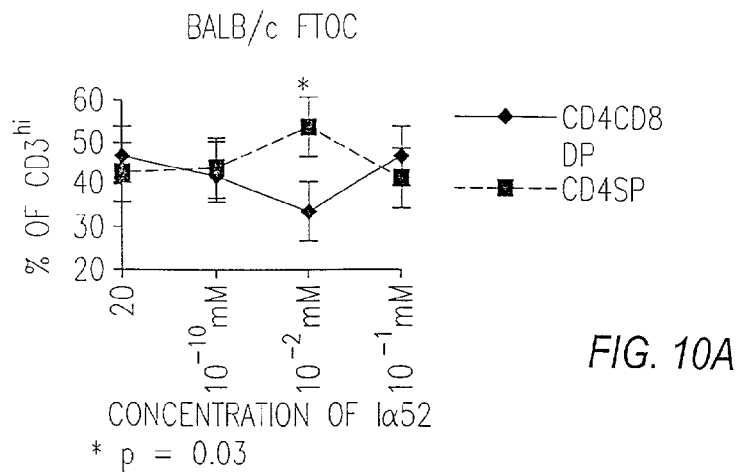
FIG. 10A, B, and C shows a series of experiments from a non-transgenic murine model in which the characterization of the antigen specificity (the Iα52 peptide) of a T cell population without the use of the current invention was attempted.
Figure 10B:
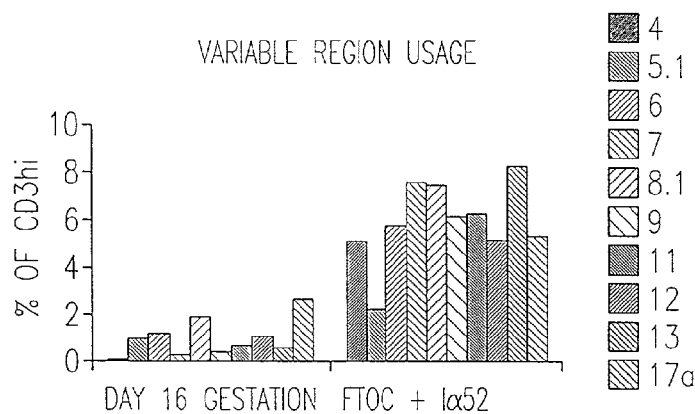
Figure 10C:
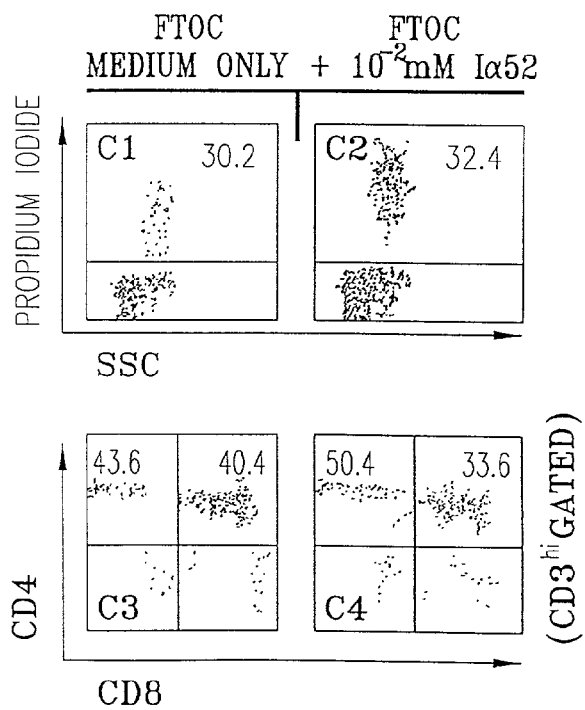

FIG. 10 shows the influence of Iα52 on the maturation of antigen specific thymocytes in fetal thymic organ cultures. FIG. 10(a) represents differing concentrations of Iα52 added to 6-day FTOC using day 16 of gestation BALB/c embryonic thymus lobes. Thymocytes were analyzed by three color flow cytometry to determine the percentages of CD3HI, CD4, and CD8 double positive and CD3HI CD4 single positive cells. With FTOC alone in the absence of any added peptide, 20.7% of CD4$^+$ cells bound liposome:I-A$^d$:biotinylated-Iα52 complexes during one week. This finding reflects the availability of Iα52 as an abundantly represented, naturally processed peptide available for thymic selection.

FIG. 10(b) shows VP analysis by FACS of cells taken directly from day 16 of gestation embryonic thymus lobes, and from FTOC supplemented with $10^{-2}$ mM Iα52.

FIG. 10(c1) represents thymocytes from FTOC without antigen, or with addition of the Iα52 peptide (c2), which were analyzed by FACS using propidium iodide to measure cell viability. Analysis of CD4, CD8 ratios from the two cell cultures (c3,4) is representative of those used in the above titration.

Figure 11:
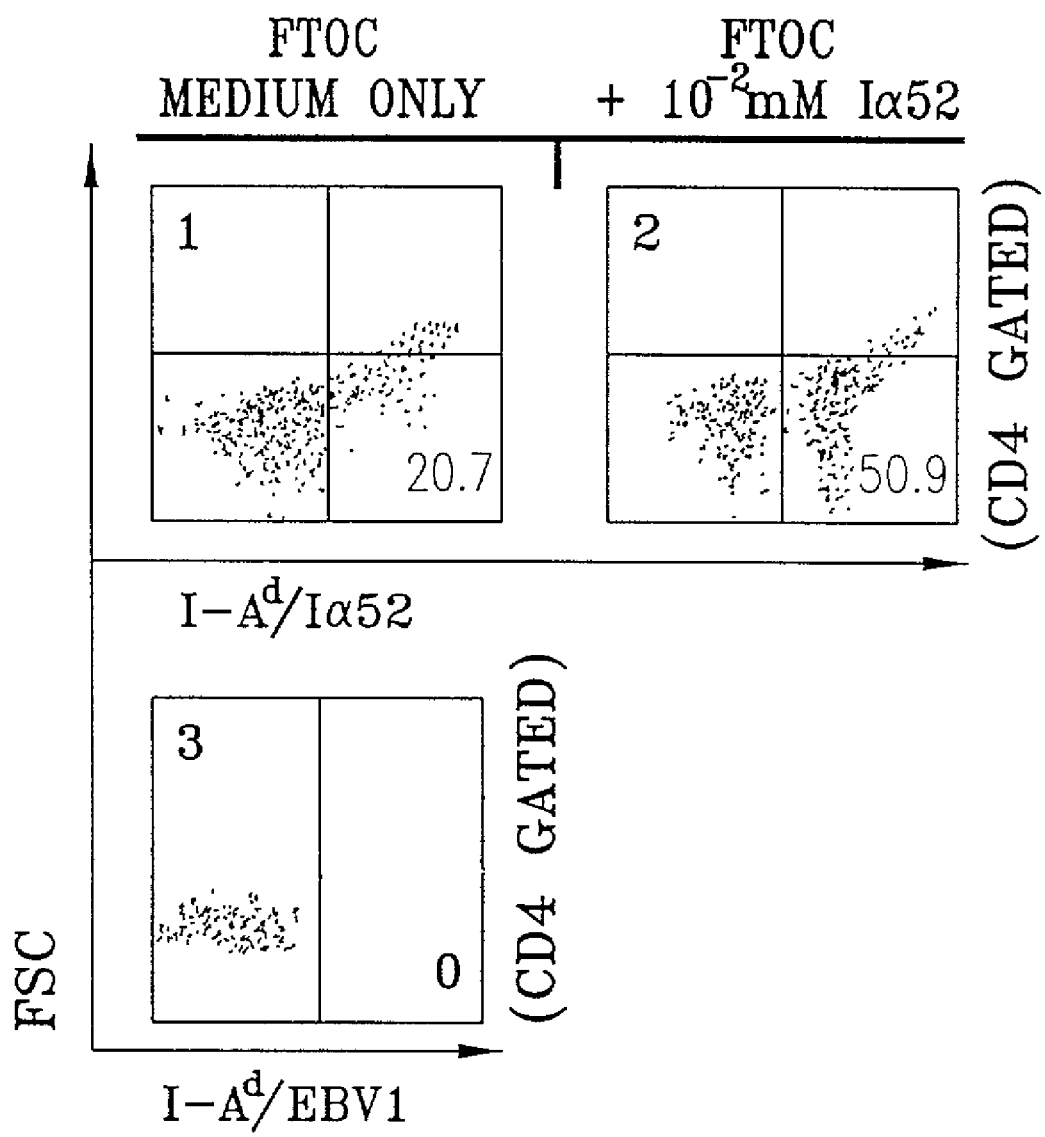
FIG. 11 shows the ability of the invention to determine directly the antigen specificity of a T cell population in the non-transgenic mouse model that could only be inferred in FIG. 10.

Performance of the detection of antigen specific thymocytes by FACS using anti-CD4 antibody and liposome: I-A$^d$:b-Iα52 complexes bound to f-strep is shown in FIG. 11. When thymic lobes were cultured for one week without the presence of $10^{-2}$ mM Iα52 (FIGS. 11-1), a relative increase (to 50.9%, FIGS. 11-2) of liposome:I-A$^d$:biotinylated-Iα52.TCD4$^+$ cells was seen in the presence of $10^{-2}$ mM Iα52. These data demonstrate for the first time that a self-derived peptide can induce positive selection in a non-transgenic system. As a control for antigen specificity in the T cell capture assay, the unrelated, biotinylated peptide EBV1 (TRDDAEYLLGRESVL), (Seq. Id. No. 2) derived from the EBV protein balf2 (residues 1030–1045) was used. EBV1 binds efficiently to I-A$^d$, and is a good immunogen in adult BALB/c mice (La Cava et al, submitted). Biotinylated EBV1 peptide complexed to I-A$^d$ in liposomes bound 0% of CD4+ cells from FTOC (FIG. 11-3).

EXAMPLE 3

Identification of Cross Reactive T Cells With Specificity for Homologous Peptides The method of the invention was used to further examine the capacity for closely related antigenic moieties to cross-react, in this case using the murine model seen in Examples 1 and 2. Evidence of such cross-reaction provides the basis for an explanation of some autoimmune disease states. In this Example, the ability of T cells selected by the self-MHC-derived peptide Iα52 to cross-react with the homologous peptide of non-self origin Hi15, was examined by performing antigen-specific T cell analysis.

Materials and Methods

Antigens.

The I-A$^d$ derived peptide Iα52 was synthesized as described in Example 2. Hi15 (TSFPMRGDLAKREPDK) (Seq. Id. No. 3) was synthesized by standard solid phase peptide synthesis technique (Research Genetics). Hi 15 was identified among 20 candidates with an arbitrary homology score of 20, based on homologies including potential MHC-binding residues. The search was performed on the non-redundant database scanned by Blast 2 program, available on the NCBI website. Peptides were >90% pure (Research Genetics). Peptides used for flow cytometry were biotinylated (b-peptides) using a commercial kit (Sigma) and were separated from free biotin by HPLC. Experiments were performed to determine the possible interference of the biotin label en the specificity of T cell receptors for the Hi15 peptide using the post-synthesis biotinylated Hi 15 and N-terminus biotinylated peptide separately complexed to MHC molecules in liposomes and labeled with different colors of conjugation to streptavidin molecules. Results showed equal binding of the two preparations to a T cell line having specificity for both Iα52, and Hi 15 (not shown).

Generation of Lymphocytes from Fetal Thymic Organ Cultures (FTOC).

FTOC was prepared as described in Example 2.

Preparation of Liposome:MHC:antigen Complexes.

Liposomes were prepared as described in Example 1.

Flow Cytometry.

Flow cytometry was performed as described in Example 1.

Results

These experiments show that a T cell population derived from Iα52-supplemented FTOC can be determined, characterized and expanded. Essentially, an artificial APC will comprise MHC:peptide complexes stabilized into liposomes, with the addition of transmembrane proteins which accomplish stabilizing, co-stimulatory, and/or modulator/functions. These accessory and co-stimulatory molecules comprise, but are not limited to, any or all of the following:

(i) ICAMI as adhesion molecule to facilitate initial interaction between the T cell and the APC.

(ii) anti-CD28 transmembrane antibody facilitates the propagation of antigen-specific T cells isolated by T cell capture using artificial APCs such that up to 20 replicative cycles have been obtained, which represents a valid alternative to T cell expansion and cloning using autologous APC systems, often an insurmountable hurdle in human systems.

(iii) B7-1 may be used instead of anti-CD28. The cells obtained from this treatment may exert immunoregulatory function in autoimmunity.

(iv) B7-2 may be used instead of anti-CD28. Cells obtained from this treatment may have immunomodulatory properties in settings such as cancer or infectious disease.

All of the aforementioned molecules are transmembrane proteins which can be incorporated into liposomes according to above examples, or as an alternative, bound to a solid support as in above examples.

Isolation and immunomodulation of antigen specific T cells.

Figure 12:
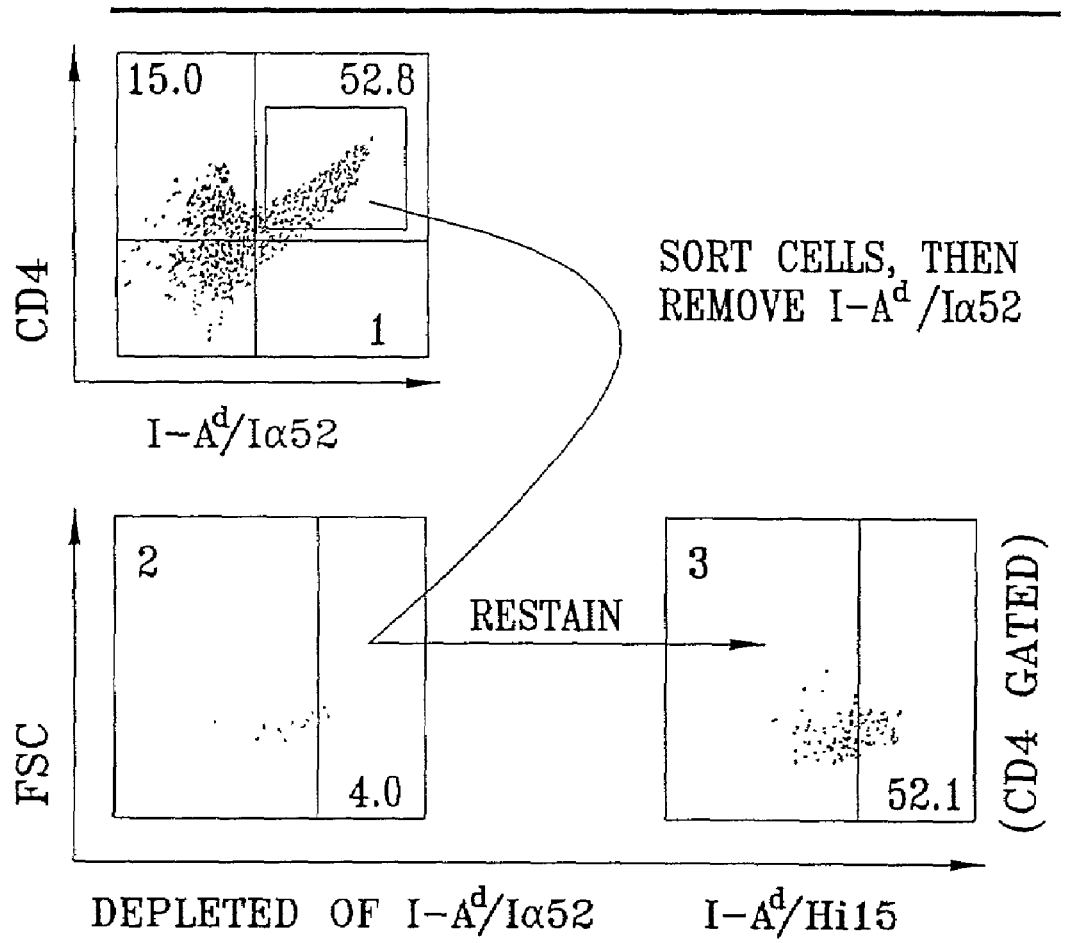
FIG. 12 shows the ability of the invention to determine the cross-reactivity of a singular group of antigen-specifically defined T cells seen first in FIG. 10, then in FIG. 11. Such a technique represents an improvement over prior art, as internalized antigen cannot be removed.
Figure 12:
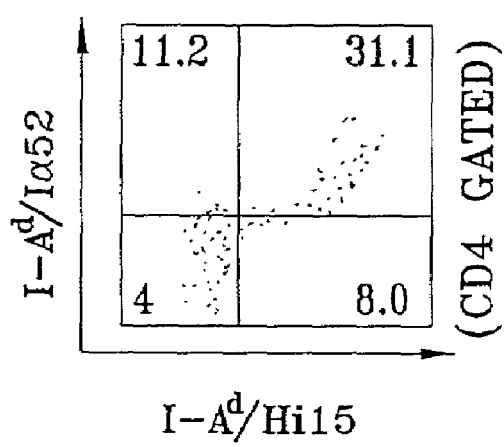
Figure 13A:
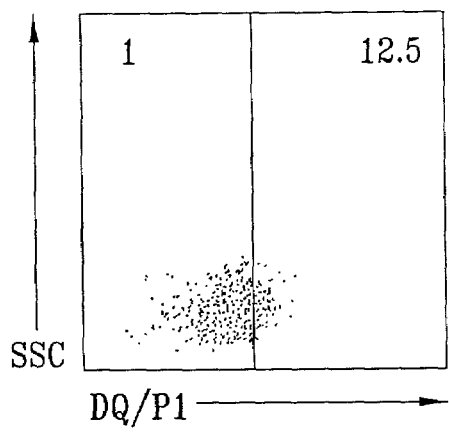
FIGS. 13A–E is a series of FACS figures showing the use of the invention to identify T cells based on the specificity of the TCR in the PBMC of a patient with RA.
Figure 13B:
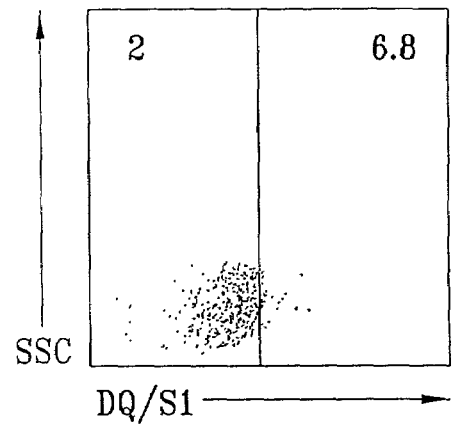
Figure 13C:
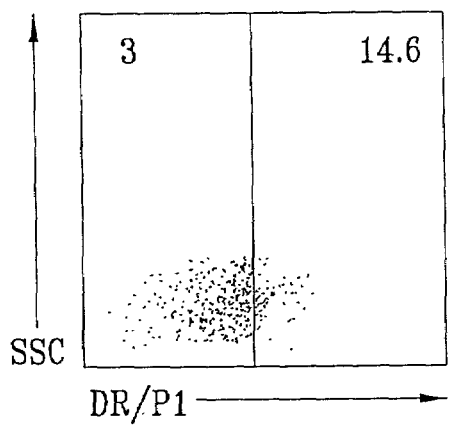
Figure 13D:
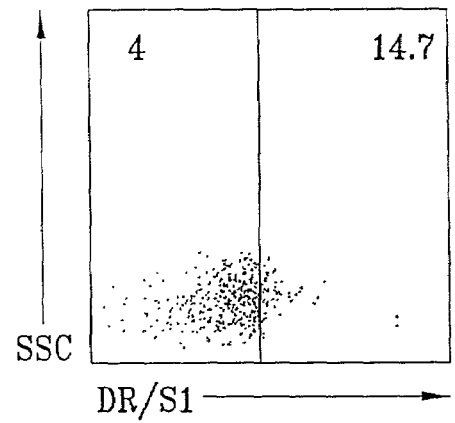
Figure 13E:
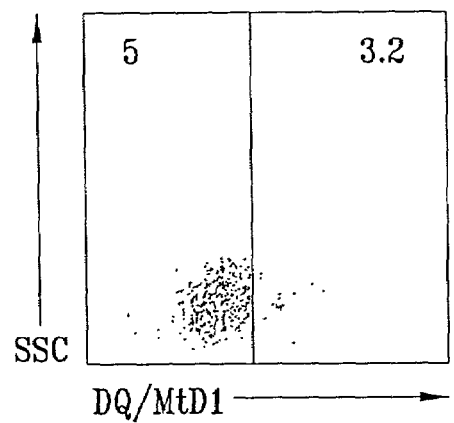
Figure 14A:
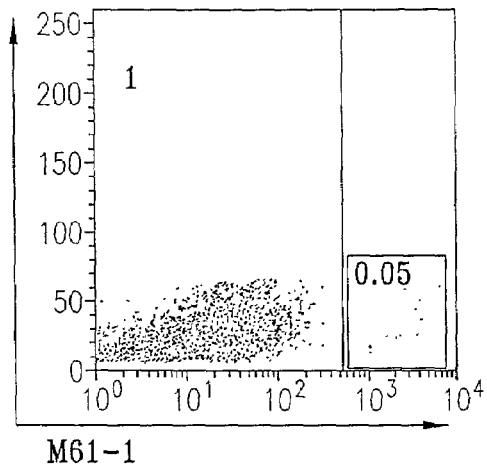
FIGS. 14A–D is a series of FACS figures showing the use of the invention to identify T cells based on the specificity of the TCR in the PBMC of a patient with JDM.
Figure 14B:
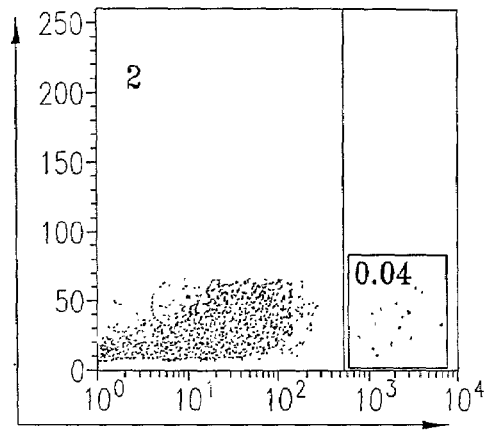
Figure 14C:
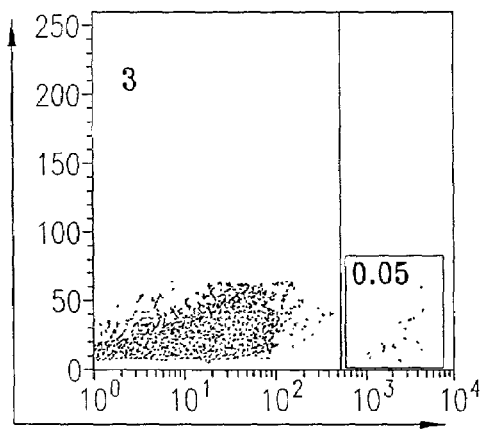
Figure 14D:
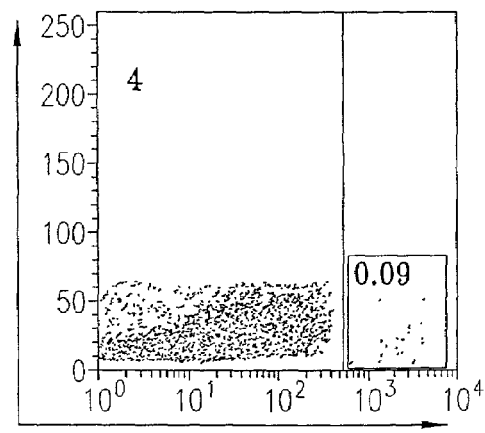

Antigen-specific T cells isolated according to above examples are incubated with the appropriate variant of the artificial antigen presenting cells according to the desired objective, i.e. expansion, functional phenotype switch, etc. Day 16 of gestation BALB/c embryonic thymus lobes were harvested and cultured on 0.4 µm filters in medium supplemented with $10^{-2}$ mM Iα52. Lobes were dissociated and cultured with autologous, irradiated APC, IL-2 and the Hi 15 peptide. After two weeks of incubation with 10µg/ml of Hi15, FACS analysis showed that 52.8% of cells bound anti-CD4 and the self-derived I-$A^d$:Iαx52 peptide complexes (FIGS. 12-1). The liposome:I-$A^d$:biotinylated Iα52$^+$:CD4$^+$ cell complexes were sorted and depleted of their liposome: I-$A^d$:Iα52$^+$ components by incubation at 4° C. for thirty minutes followed by centrifugation at 325×g for 10 minutes through 100% PCS (FIGS. 12-2). The sorted cells were then restained with liposome:I-$A^d$ and the exogenous, biotinylated peptide Hi 15 which was complexed to a streptavidin molecule conjugated to a fluorochrome. The restained T cells were then reanalyzed by three-color flow cytometry using anti-CD4 antibody, liposome:I-$A^d$:b-Hi15 complexes, and liposome:I-$A^d$:b-Iα52 complexes bound to different color f-strep molecules. Results showed that 52% of the cells tested positive (FIGS. 12-3). To further demonstrate the ability of TCRs selected by Iα52 to recognize the exogenous antigen Hi 15, T cell populations derived from Iα52 FTOC were expanded with Hi 15 and incubated with anti-CD4 antibodies and lipsome:I-$A^d$ complexes bearing either biotinylated-Iα52 or Hi15 bound to streptavidin molecules labeled with different fluorochromes. Our results indicated that 31.1% of the CD4$^+$ cells were positive for both peptides (double positive) (FIGS. 12-4). The results of this Example 3 show that positive selection by a self-peptide generates CD4$^+$ T cells that can recognize a homologous, exogenous peptide.

EXAMPLE 4

Identification of TCR Usage by Antigen Specific T Cells

Variable regions of TCRs on the cross-reactive cells identified in Example 3 were evaluated in order to demonstrate the absolute ability of the method of the current invention to evaluate TCR specificity and potential cross-reactivity seen at a molecular level.

Materials and Methods

Antigens.

The Iα52 (ASFEAQGALANIAVDKA) (Seq. Id. No. 1) peptide (Research Genetics) and the Hi15 (TSFPMRGD-LAKREPDK) (Seq. Id. No.3) peptide (Research Genetics) were >90% pure. Peptides used for flow cytometry were biotinylated (b-peptides) using a commercial kit (Sigma) and were separated from free biotin by HPLC.

Generation of Lymphocytes from Fetal Thymic Organ Cultures (FTOC).

FTOC were prepared as described in Example 2.

Preparation of Liposome:MHC:Ag Complexes.

Liposomes:MHC:antigen complexes were prepared as described in Example 1.

Flow Cytometry.

Flow cytometry was performed as in Example 1.

Analysis of T Cell Receptor Gene Usage.

To analyze the TCR-Vβ repertoire, 500 FACS-sorted cells were washed twice and poly (A) mRNA was isolated with the Invitrogen Micro Fast Track mRNA Isolation kit (Invitrogen, San Diego). The resulting mRNA was quantified with DNA DipStick kit (Invitrogen) and equal amounts of mRNA from each source were reverse transcribed using Invitrogen's cDNA Cycle kit. The cDNA was then submitted to a first PCR by using specific Vβ sense primers and a common Cβ antisense primer (Lessin, et al., *J. Invest. Dermatol*, 96:299–302, (1991) herein incorporated by reference). PCR conditions were 200 uM dNTPs, Ix Taq polymerase buffer, cDNA, 20 µM each primer, 0.6 U Taq DNA polymerase (Boehringer Mannheim) in a 25 ul total reaction volume. After 3 minute hot start at 94° C. and addition of Taq DNA polymerase at 80° C. using a Perkin Elmer 2400 thermal cycler, reactions were cycled 40 times consisting of 30 seconds at 94° C., 30 seconds at 55° C. and 40 seconds at 72° C., last extension 6 minutes. Five microliters were used as template for a second PCR, whose conditions were identical to the previous PCR, except that reactions were cycled 35 times and 0.125 U of Taq DNA polymerase was used. Twenty-five microliters of the resulting PCR products were then analyzed by electrophoresis through a 4% agarose gel and ethidium bromide staining. DNA sequencing was performed at The Scripps Research Institute Core Facility using an ABI system.

Results

T cell lines obtained from either FTOC supplemented with $10^{-2}$ mM Iα52, or from peripheral lymph nodes of animals immunized with Iα52, were subsequently expanded in the presence of Hi 15 and IL-2. Cells were sorted by FACS, as described in Example 1 using cytometry based on anti-CD4, liposome:I-$A^d$:biotinylated-Hi15 and liposome:I-$A^d$:biotinylated-Iα52 triple binding. Then, RT-PCR specific for the known TCR Vβ families was performed.

The results of these experiments showed almost exclusive use of Vβ1 by cells that recognized both the selecting self-peptide Iα52 and the cross-reactive, non-self homologue—Hi 15-(Table II). We also obtained DNA sequences from three representative clones. This analysis showed only modest differences in amino acid sequence for various representative clones, which all utilized Vβ1 genes (Table II). Molecular modeling showed that these amino acid sequences had little effect on the predicted conformation of the Vβ chain used by the different clones (FIG. 9).

TABLE II

CDR3 Sequence Comparison and Variable Region Gene Usage of Iα52 and Hi 15 Cross-Reactive T Cell Receptors

| T Cell Line | Isolated VDJ sequences |
|---|---|
| R3 F17 | LHIS AVDPEDS AVYFCASSQEFFSS YEQYFGPGTRL* |
| R3F16 | I |
| R3F15 | T |
|  | Variable Region (Vβ) Gene Usage |
| F7d | 1, 8 |

Lines were generated from single cell sorting by flow cytometry using the T cell capture assay.
Detection in the assay was based upon I-Ad/b-Iα52 and I-Ad/b-Hi 15 double binding.
These sequences contain the Vβ1 region of murine TCR in positions 78–107.
*Seq. Id. No. 4.

EXAMPLE 5

Identification, Isolation and Characterization of T Cells Specific for Rheumatoid Arthritis-Related Antigens Initiation of autoimmune diseases such as rheumatoid arthritis is thought to be dependant on the recognition by T cells of one or more "pathogenic" antigens which may be responsible for triggering proinflammatory events which lead to chronic autoimmune damage. Several different hypotheses and experimental approaches have led to the identification of a pool of potential pathogenic antigens.

In this Example 5, it is demonstrated how T cells specific for rheumatoid arthritis-related antigens can the identified and enumerated starting from polymorphic T cell populations with very diverse specificities. Peripheral blood mononuclear cells (PBMC) from a patient with rheumatoid arthritis are incubated with a peptide called dnaJp1 (U.S. Pat. No. 5,773,570) corresponding to certain positions of the *E. coli* heat shock protein dnaJ. Certain peptides derived from dnaJ are homologous to rheumatoid arthritis-associated HLA alleles, and have been shown to be immunogenic in patients with rheumatoid arthritis. (Albani et al., "Positive selection in autoimmunity: Abnormal immune responses to a bacterial dnaJ antigenic determinant in patients with early rheumatoid arthritis," *Nat. Med.* 1:448–452 (1995); Albani & Carson, "A multistep molecular mimicry hypothesis for the pathogenesis of rheumatoid arthritis," *Immunology Today* 17:466–470 (1996); La Cava et al., "Genetic bias in immune response to a cassette shared by different microorganisms in patients with rheumatoid arthritis," *J. Clin. Invest* 100: 658–663 (1997). Each of the above reference are herein incorporated by reference).

Materials and Methods

Preparation of DNA.

Genomic DNA is prepared from white blood cells by methods known to those skilled in the art utilizing ammonium acetate and isopropyl alcohol precipitation with resuspension in TE (1 mM Tris, 0.1 mM EDTA, dH2O, pH 7.5).

PCR amplification.

DNA is enzymatically amplified by the polymerase chain reaction and amplification primers that have previously been reported for DQA1 and DQB1, for level I DRB typing, for level 2 allele assignment of DRB1 specificities associated with DR52, and for DR4 and DR1 (Vooter, C. E. *Tissue Antigens* 51:1:80–87.; Barnardo, M. C. *Tissue Antigens* 51:3:293–300; Mitsunaga, S. *Eur J Immunogenet.* 25:1: 15–27). Genomic DNA (5–10 µl at 80–150 µg/ml) is added to PCR mix consisting of 5 µl of 2 mmole/µl dNTPs, 3 µl of each primer at 10 pmole/µl, 5 µl of 10× PCR buffer, 0.5 µl of Taq polymerase (5 U/µl) and 23.5 µl sterile dH20. Total reaction volume is 50 µl. DNA is amplified for 30 cycles in a DNA Thermal Cycler (Perkin Elmer Cetus) with denaturation, annealing and extension parameters that vary depending upon the locus studied. In general, annealing is at 53° C. for DQ and DRB level I, and at 60° C. for DRB 1-specific families. Positive and negative controls are included with each run and care is taken to avoid any source of contamination.

SSOP hybridization and detection.

After amplification, 5.0 µl samples (10% of total PCR mixture) are run on a 1.0% agarose gel to verify sufficient quantity of amplified product. The remaining portion of the samples (90% of total PCR mixture) are denatured prior to blotting and hybridization using chem-luminescence using methods known to those skilled in the art. Membranes are washed twice with 2×SSC+0.1% SDS (0.3 M NaCl, 0.03 M Na-citrate, 0.1% SDS, dH2O, pH 7.0) for five minutes at room temperature, and then twice with 3 M TMAC buffer in the appropriate temperature for the length of the probe. Fifteen-base pair probes are washed at 50–52° C. and 18-base pair probes are washed at 59–61° C. Membranes are wetted with Lumi-Phos (Boehringer Mannheim), sealed in acetate sheets, and exposed to X-ray film for 1 to 5 minutes. Results are graded using 11th International Workshop criteria as follows: 1: negative (definite) 2: negative (probable) 4: indefinite 6: positive (probable) 8: positive (definite) 9: positive (definite, more than double intensity). If unique hybridization patterns are found in the course of these studies sequence analysis is done. The patient employed in the example was HLA typed by PCR.

HLA Purification.

Lymphoblastoid cell lines from RA patients are used as a source of HLA molecules, as known to those skilled in the art. Allele and species-specific monoclonal antibodies, whose corresponding hybridomas are already available, are produced as ascites liquid from BALB/c mice and purified on protein A, and covalently bound to a solid support (AffiGel, Bio-Rad, Richmond, Calif.). HLA molecules are purified by immunoaffinity chromatography from lysates of $10^8$ lymphoblastoid cells. The yield ranges from 1 to 4 mg/preparation. Purity is assessed by SDS/Page and Western blotting. Molecules in an elution buffer containing 0.2% octasilglucoside are stable for more than 4 months at 4° C.

Preparation of Liposome:MHC:Antigen Complexes.

Liposomes are prepared as described in Example 1.

Flow Cytometry.

Flow cytometry is performed as described in Example 1.

Results.

T cells specific for the various combinations of the HLA, DR/DQ, and SI or dnaJp1 peptides were enumerated. T cells binding the SI or dnaJp1 peptides in the context of HLA DR are more abundant (FIGS. 13A–E). Seen in the figure are PMBC from an RA patient expressing disease associated alleles DRB* 10401 and DQ*30301 captured with DQ/PI (FIG. 13-A), DQ/SI (FIG. 13-B), DR/PI (FIG. 13-C), DR/SI (FIG. 13-D), and DQ/Mtd1 (FIG. 13-E).

In order to demonstrate cross-reactivity, T cells specific for the various HLA/peptide combinations are sorted and RT-PCR for TCR VP gene usage is performed. The results, shown in Table III, demonstrate that T cells specific for the self-HLA derived peptide SI cross-react with the homologous peptide dnaJp1. Identification and isolation of T cells with a high pathogenic potential, as described in this Example 5 allows manipulation ex vivo to induce tolerization.

TABLE III

TCR Vβ Usage of T cells Isolated by Detection with RA Associated HLA Molecules Bound by Self or Exogenous Peptides.

|  | HLADQ | HLADR |
|---|---|---|
| dnaJP1 | 1, 8, 12 | 8, 14 |
| SI | 4, 12, 21 | 1, 9, 14 |

Peripheral blood mononuclear cells were isolated from an RA patient expressing the RA associated HLA alleles DRB*10401 and DQB*30301. The cells were cultured for five days in the presence of IL-2 and the bacterial heat shock protein peptide dnaJP1 then sorted by flow cytometry using HLA/Antigen combinations complexed into liposomes. RT-PCR was performed on sorted cells using primers specific for the known Vβ regions. Data are representative of two separate experiments.

The numbers in the above Table III show that of the 23 genes of the Vβ gene family, cross reaction occurs with only a few even though the family is highly related. Additionally, the results show that individual members of the family can be detected using the T cell capture method of the invention using artificial APCs.

EXAMPLE 6

Identification, Isolation and Characterization of T Cells Specific for Juvenile Dermatomiosytis-Related Antigens Juvenile Dermatomiosytis is a chronic autoimmune disease of unknown etiology. It has been reported that in several patients there is an association between relapse of the disease and documented *Streptococcus pyogenes* infection (Martin, A., Ravelli, A., Albani, S., J. *Peds*, 121: 739–742 1992). Sequences shared between *Streptococcus* M5 protein and the human skeletal myosin, the target of the autoimmune process have been reportedly identified. It has also been demonstrated that the shared sequences contain epitopes which elicit cross-reactive T cell responses. In this Example 6, it is demonstrated that the homologous sequences are actually recognized by T cells which bear the same TCR Vβ gene.

Materials and Methods

Sequence-specific oligonucleotide probe HLA typing was performed as described in Example 5.

Preparation of Liposome:MHC:Antizen Complexes.

Liposome:MHC:antigen complexes are prepared as described in Example 1.

Flow Cytometry.

Flow Cytrometry is performed as in Example 1.

Two alternative methods for visualization of the antigen-specific T cells were employed. In the first method, affinity-purified HLA molecules were stabilized by incorporation within the interior of liposomes using a method similar to that described in Examples 1–5 and then incubated with biotinylated peptides which were labeled using a method similar to that described in Examples 1–5. In a second alternate method, a label, in this case fluorescent (FITC), was incorporated directly into the liposomes themselves. Thus, the liposomes, rather than the peptides were labeled. FIGS. 14A–D shows data representing PBMC from a patient with JDM capture with a class I HLA and M61-1, M61-1*, M61-2, and M61-2* (FIGS. 14-A to 14-D, respectively).

Results from these experiments show that T cells which recognize homologous peptides of either self or bacterial origin use the same TCR Vβ genes, confirming cross-reactivity at a molecular level. In addition, a direct identification and enumeration of CD3+ antigen-specific T cells is possible without detectable differences in sensitivity between the two labeling methods used. These results also suggest that direct incorporation of a label, e.g., FITC, into the liposomes themselves, or incorporation of a labeled (e.g., biotinylated) transmembrane protein which may or may not interfere with the TCR:antigen:MHC interactions, represent valid methods as alternatives in labeling of the liposome. This may be advantageous in that a label (e.g., a biotin molecule) when complexed with the peptide, may interfere with the interactions among agretopes and epitopes within the TCR:antigen:MHC complex. This may be especially true with class I MHC molecules, in which the antigen binding groove is open only at one end. Our diverse approaches bypass these potential limitations.

EXAMPLE 7

Identification and Enumeration of T Cells Specific for Peptides from Pathogenic Organisms Physiologic, as well as vaccine-induced, immune responses to infectious agents are based on T cell recognition of, and reactivity to, immunogenic epitopes of the infectious agents. In several instances, immunogenic epitopes of microorganisms employed in vaccines, and their HLA restrictions, have been identified. One example is the influenza vaccine.

In this Example, quantitative and qualitative T cell response abnormalities in response to influenza vaccination can be identified. Peptides encompassing the major epitopes of the influenza virus are employed for analysis. Antigen specific T cells are identified and isolated as described in Example 1. The population to be screened is comprised of elderly persons who are vaccinated and then screened for immune responses. Antigen specific T cells are quantified and isolated from both the responder and non-responder groups. Phenotypical and functional characteristics are then evaluated, and the results compared between the two groups to analyze whether hyporesponsiveness in some of the vaccinated subjects is related to lack of specific T cells.

PBMC are incubated with the relevant and control peptides for five days in order to increase precursor frequency. Cells are then incubated with HLA-peptide complexes, and positive cells are enumerated by FACS. Commercially available cell lines are the source of soluble HLA molecules (Corriel Cell Repository).

Antigen specific T cells are evaluated for the production of cytokines which are related to either effective responses to viruses (IFN, IL-2) or associated with anergy (as in the case of using, for example, IL-10). This analysis elucidates differences, if any, between antigen specific T cells of responders versus non-responders. Hence, important functional differences are evaluated at an antigen-specific T cell level. Membrane phenotype of the isolated antigen specific T cells is evaluated, with particular attention to early activation markers, such as CD69, and memory, such as CD45RO. This test helps distinguishing anamnestic from recently induced responses. mRNA is purified and RT-PCR using Vβ chain for the T cell receptor specific primers is performed. The definition of the T cell receptor (TCR) used by the various subjects may help in pointing out differences between responders and non-responders due to genetic differences in the TCR repertoire. This shows the potential for the technology of the current invention to discriminate between anamnestic and recall immune responses at the level of antigen-specific T cells.

Materials and Methods

Lymphocyte proliferation assays.

Preliminary experiments are performed to identify the optimal conditions for culture. Initially, cell cultures are performed in duplicate for three to seven days, using 5 million cells/well. (All antigens have shown a range of optimal responses between 1 and 10 µg/ml). The proliferation assays are conducted as controls to compare against the T cell capture specificity of the invention.

Lymphocyte cytotoxicity tests.

Cytotoxic responses are measured using a LDH-release kit (Promega). The tests are performed according to manufacturer's instructions. Effectors are incubated for 5 days with IL2 and the relevant peptides or with irrelevant antigens. Targets are irradiated autologous PBMC or, when available, EBV-transformed lymphoblastoid cell lines. Targets are pulsed with the relevant antigens overnight. The cytotoxicity assays are conducted as controls to compare against the T cell capture specificity of the invention.

Antigens.

Synthetic peptides (Matrix 58–66:GILGFVFTL (Seq. Id. No. 5); Nucleoprotein 82–94:VKLGEFYNQ (Seq. Id. No. 6)) are purchased from Research Genetics.

MHC purification.

Commercially available lymphoblastoid cell lines (Corriel Cell Repository) are used as a source of MHC molecules and purified by immunoaffinity chromatography using anti-HLA class I antibodies in a manner similar to that shown in Example 5.

Liposome:MHC:antigen complexes are prepared as described in Example 1. Antigen specific T cells are prepared as described in Example 1. Intracellular immunofluorescence staining of cytokines was performed as described in Example 10.

Cytokine measurement by RT/PCR.

mRNA is extracted from approximately $7\times10^6$ cells by using Oligotex Direct mRNA Kit (Qiagen, Chatsworth, Calif.). mRNA is reverse-transcribed into cDNA with the oligo dT primer (RT-PCR Kit, Stratagene, La Jolla, Calif.). Two µl of single strand cDNA are amplified using the cytokine specific forward and reverse primer sets, IL-2, IL4, TNF-a, INF-γ. Quantitative measurement of various cytokines using competitive PCR is performed (Biosource reagents). In this method, a known copy number of an exogenously synthesized DNA used as an internal control sequence (ICS) is mixed with the sample prior to amplification. The ICS is constructed to contain identical primer binding sites as the cytokine to be analyzed, and a unique binding site that allows the resulting amplicon to be distinguished from the cytokine product. Detection of the amplification product is by non-radioactive microplate techniques.

T cell receptor analysis by PCR.

Messenger RNA is extracted from a minimum of 70 cells by using Micro-FastTrack Kit (Invitrogen, Carlsbad, Calif.). The yield of mRNA is about 2 µg that is resuspended into 20 µl of water. Two µl of mRNA for each reaction is reverse-transcribed into single strand cDNA with the oligo dT primer (cDNA Cycle Kit, Invitrogen, Carlsbad, Calif.). 1.5 µl of single strand cDNAs are amplified with constant primer and various V region primers (Vb1–Vb24), the sequences of which may be designed by those knowledgeable in the art. For example, 20 pico moles of each primer and 1.25 units of Taq polymerase (Boehringer Mannheim, Germany) are used. The total volume is 25 µl. The cycling parameters for PCR is indicated as: heat PCR reaction mixture without Taq and dNTPs at 94° C. for 4 min, then perform 40 cycles of 30 seconds at 94° C., 30 seconds at 58° C. and 30 seconds at 72° C. The final elongation is 7 minutes at 72° C. Add 0.5 µl of 100 mM dNTPs and 0.25 µl of Taq Polymerase (1.25 units, Boehringer Mannheim) at end of 58° C. of first cycle. The PCR-amplified products are analyzed on 4% agarose gel.

In summary, the experiments described in this Example 7 are accomplished according to the following steps:

i) MHC typing by PCR of the test sample derived from a test subject, (e.g. a patient that is to receive treatment against an infectious agent);

ii) Purification by immunoaffinity chromatography or by other methods known to those skilled in the art, of MHC molecules corresponding to that of the test subject's. The source for these molecules may be directly from an individual or from cell lines homozygous for the HLA alleles.

iii) Synthesis of liposomes containing MHC:peptide complexes. (These liposomes may be tagged according to any of the methods described herein or known by those in the art.);

iv) Incubation of PBMC from the test subject with the MHC:peptide tagged liposomes, and;

v) counting of the binding T cells for the purpose of determining which peptides have bound thereby indicating the specific peptides effective in binding antigen-specific T cells.

Methods described in this Example are useful in determining the number of vaccine-specific T cells in peripheral blood, both in normal and immune compromised individuals, for example, as a tool for decisions regarding the opportunity for vaccination in immune compromised subjects, and in determining the efficacy of vaccination, measured as increase in the number of vaccine-specific T cells after vaccination.

EXAMPLE 8

Diagnosis and Immunomodulation of Allergic Disease

Allergy is mediated by release of pro-inflammatory and vasoactive mediators triggered by binding of allergen specific immunoglobulins with receptors of inflammatory cells at the site of allergen contact with cellular tissues. The production of allergen specific immunoglobulins-appears to be mediated by strong interactions between B and T cells, an example being Casein in the pathogenesis of lactose intolerance (Albani, S. *Annals of Allergy.* 63:12:489–492.). It is therefore of importance to have the possibility to identify allergen specific T cells, isolate them and manipulate them ex vivo. An outline of the strategy to be employed is:

i) MHC typing of the test subject by PCR technology;
ii) Identification of candidate "allergenic" peptides, based on current knowledge of the field. (When a candidate epitope on a given proteic allergen will not be already available, computerized analysis of MHC binding motifs will enable the identification of candidate peptides to be used.);
iii) Synthesis of liposomes containing relevant MHC:peptide complexes. (Such liposomes can be tagged using any of the techniques described herein or known by those in the art.);
iv) Incubation of PBMC of the test subject with the MHC:peptide:tagged liposomes complexes;
v) Identification and enumeration of allergen specific T cells;
vi) manipulation ex vivo of such cells, by stimulation in culture with the antigenic peptide in the presence of stimuli related to induction of Th-1 phenotype.

Materials and Methods

Lymphocyte proliferation assays are performed as described in Example 7.

Lymphocyte cytotoxicity tests are performed as described in Example 7.

Antigens.

Peptides are identified based on scanning the sequences of the proposed allergens for MHC-binding motifs and synthesized according to standard peptide synthesis methods know to those in the art.

MHC purification is performed as described in Example 7.

Liposome MHC:antigen complexes are prepared as described in Example 1.

T cells, generated as described in Example 1, are captured by separation using flow cytometry as described in Example 1.

Intracellular immunofluorescence staining of cytokines, is performed as described in Example 5.

Cytokine measurement by RT/PCR is performed as described in Example 7.

T cell receptor analysis by PCR is performed as described in Example 7.

This Example therefore shows that artificial APCs may be used to diagnose and monitor progress of therapies and modulation level of specific responses in a patient's T cells.

EXAMPLE 9

Identification of Cancer-Specific T Cell Epitopes

It is commonly accepted that lack of immunity to cancer (e.g., melanoma), depends on low antigenicity of the neoplasm, as well as on functional and/or numerical deficiencies of antigen-specific T cells.

Several therapeutical approaches are currently underway to improve the efficiency of recognition of and reactivity to cancer antigens by T cells. Unfortunately, the efficiency of the treatment can be measured, to date, only in terms of clinical outcome. This Example 9 describes a solution to this problem, by enabling identification, enumeration, characterization and possible manipulation of cancer-specific T cells. Hence, efficiency of the treatment will be measured in terms of increase in antigen-specific precursor frequency, and also in terms of functional outcome of antigen recognition. This latter aspect is of particular importance in those instances where the therapy is aimed at activation of otherwise dormant T cells.

The following protocol is applied:

i) MHC typing by PCR of the test subject;
ii) Identification of candidate peptides. For example, sources for antigen in the treatment of melanoma include MAGE-1, MAGE-3, MART-1/melan-A, gp100, tyrosinase, gp75, gp15, CDK4 and beta-catenin. When a candidate epitope on a given protein allergen will not be already available, computerized analysis of MHC binding motifs will enable the identification of candidate peptides to be used;
iii) Synthesis of liposomes containing relevant MHC:peptide complexes;
iv) Incubation of PBMC of the test subject with the MHC:peptide:tagged liposomes complexes;
v) Identification and enumeration of antigen specific T cells.

Materials and Methods

Lymphocyte proliferation assays are performed as described in Example 7.

Lymphocyte cytotoxicity tests are performed as described in Example 7.

Antigens.

Synthetic peptides will be identified based on scanning the sequences of the proposed allergens for HLA-binding motifs.

MHC purification.

MHC purification is performed as described in Example 7. Commercially available lymphoblastoid cell lines (Corriel Cell Repository) are used as a source of MHC molecules, and purified by immunoaffinity chromatography using anti-MHC class I antibodies, available in our laboratory.

Liposome MHC:antigen complexes are prepared as described in Example 1.

T cells, generated as described in Example 1, are captured by separation using flow cytometry as described in Example 1.

Intracellular immunofluorescence staining of cytokines, is performed as described in Example 5.

Cytokine measurement by RT/PCR is performed as described in Example 7.

T cell receptor analysis by PCR is performed as described in Example 7.

As shown, a peptide based method for monitoring cancer therapy is established using antigen-specific artificial APCs. This methods allows for studying the progress of the therapy and the state of the cancer.

EXAMPLE 10

Methods for Distinguishing "Bystander T Cells" from Antigen-Specific T Cells The experiments described in this Example demonstrate that antigen-specific T cells can be identified and enumerated and distinguished from antigen non-specific T cells present in the same tissue. These latter cells (so-called "bystander T cells") may participate in pathogenic processes. This has particular relevance for autoimmune and allergic diseases, where the initiating event may be the recognition of a pathogenic antigen by a specific T cell population. This interaction leads to production of pro-inflammatory or pro-allergic mediators (i.e., cytokines) by the antigen-specific T cells. The cytokine cascade will subsequently involve T cells that are not specific for the antigen (bystander T cells), which may then participate in the pathogenic processes, amplifying significantly the degree of the damage. It is important in a clinical or research setting to discriminate between the antigen-specific and bystander populations in order to evaluate, for instance, the efficacy of a treatment. The strategy may be summarized as follows;

i) Identification of candidate peptides, based on current knowledge of the field. When a candidate epitope on a given protein antigen is not already available, computerized analysis of MHC binding motifs will enable the identification of candidate peptides to be used in the "T cell capture". Such analysis is standard practice to those skilled in the art;

ii) Synthesis of liposomes containing relevant MHC: peptide complexes. Such liposomes can be tagged using any of the techniques described herein;

iii) Incubation of PBMC of the test subject with the MHC:peptide:tagged liposomes complexes;

iv) Identification and enumeration of antigen specific T cells.

Materials and Methods

Lymphocyte proliferation assays.

Preliminary experiments may be performed to identify the optimal conditions for culture. Cell cultures may be performed in duplicate for three to seven days, at 5 million cells/well. All antigens have shown a range of optimal responses between 1 and 10 µg/ml.

Lymphocyte cytotoxicity tests.

Cytotoxic responses may be measured using a LDH-release kit (commercially available). The tests may be performed according to manufacturer's instructions. Effectors may be incubated for 5 days with IL2 and either the relevant peptides or with irrelevant peptide antigens. Targets may be irradiated autologous PBMC or, when available, EBV-transformed lymphoblastoid cell lines. Targets may be pulsed with the relevant antigens overnight.

Antigens.

Synthetic peptides are identified based on scanning the sequences of the proposed allergens for MHC-binding motifs.

MHC purification.

Commercially available lymphoblastoid cell lines (Corriel Cell Repository) may be used as a source of MHC molecules and purified by immunoaffinity chromatography using anti-MHC class I antibodies.

Preparation of Liposome MHC:Ag Complexes.

Preparation of APCs are the same as that performed for Example 1.

FACS. A Beckton Dickenson FACS Star with LYSIS II software was used to visualize cells. Sortings were performed by the Flow Cytometry Core at UCSD.

T cell Capture.

T cells, generated as described, are captured by separation using flow cytometry. Bulk sorted cells are either cultured as described, immediately used for DNA analysis, or used directly for reanalysis using FACS. Yields from bulk sortings range from 2000–16,000. Single cell sorts utilized 96 well culture plates containing media previously described. Fresh irradiated APCs are added to the single cell cultures once per week, at which time analysis of clonal expansion is performed. Of 96 wells of sorted "events", generally 8–12 show good expansion over a six week period.

Intracellular immunofluorescence staining of cytokines.

Human PBMC are isolated by density centrifugation and stimulated for 36 hours with peptides at 10 µg/ml in the presence of 2 µM monensin. Cells are washed in PBS with 2% FCS and incubated with Fc-block for 5 min. at 4° C. PE-conjugated anti-CD3 monoclonal antibodies (mABs) are added and cells are incubated for 30 min. at 4° C. Cells are washed, fixed 20 min. at 4° C., and resuspended in a solution containing either FITC conjugated anti-IFNγ mAbs or FITC conjugated anti-IL4 or IL2 mAbs. Cells are incubated for 30 min at 4° C., washed twice in PBS with 2% FCS and their fluorescence measured using a Becton Dickinson FACScan. Flow data are analyzed using Lysis II software (Becton Dickinson).

Cytokine measurement by RT/PCR.

Messenger RNA is extracted from approximately $7 \times 10^6$ cells by using Oligotex Direct mRNA Kit (Qiagen, Chatsworth, Calif.). The mRNA is reverse-transcribed into cDNA using oligo dT primer (RT-PCR Kit, Stratagene, La Jolla, Calif.). Two µl of single strand cDNA are amplified using the cytokine specific forward and reverse primer sets for IL-2, IL4, TNF-α, and INF-γ. Quantitative measurement of the various cytokines was carried out using competitive PCR (Biosource). In this method, a known copy number of an exogenously synthesized DNA (ICS) is mixed with the sample prior to amplification. The ICS has been constructed to contain identical primer binding sites as the cytokine to be analyzed, and a unique binding site that allows the resulting amplicon to be distinguished from the cytokine product. Detection of amplicons is allowed by non-radioactive microplate techniques.

T cell receptor analysis by PCR.

Messenger RNA is extracted from a minimum of 70 cells by using Micro-FastTrack Kit (Invitrogen, Carlsbad, Calif.). The yield of mRNA is about 2 µg that is resuspended into 20 µl of water. 2 µl of mRNA for each reaction is reverse-transcribed into single strand cDNA with the oligo dT primer (cDNA Cycle Kit, Invitrogen, Carlsbad, Calif.). 1.5 µl of single strand cDNAs are amplified with constant primer and different V region primers (e.g., Vb1–Vb24). 20 pico moles of each primer and 1.25 units of Taq polymerase (Boehringer Mannheim, Germany) were used. The total volume is 25 µl. The cycling parameters for PCR are: heat PCR reaction mixture without Taq and dNTPs at 94° C. for 4 min, performance of 40 cycles for 30 seconds at 94° C., 30 seconds at 58° C. and 30 seconds at 72° C. The final elongation is 7 minutes at 72° C. Add 0.5 µl of 100 mM dNTPs and 0.25 µl of Taq Polymerase (1.25 units, Boehringer Mannheim) at end of 58° C. of first cycle. The PCR-amplified products were analyzed on 4% agarose gel. The sequences of Vβ-specific primers which may be used may be designed by those knowledgeable in the art.

This example therefore shows that antigen-specific immunotherapy can be used to influence populations of T cells having different specificity which participate in the pathogenic process.

EXAMPLE 11

Immunoaffinity Chromatography for Positive Selection of Antigen-Specific T Cells As demonstrated in this Example, MHC:antigen complexes may be incorporated into liposomes as described in certain embodiments of the invention above and bound to a solid support. By orienting the complexes so as to optimize the chance of interaction between the T cell receptor and the complexes, antigen-specific T cells may be isolated from biological samples.

Immunoaffinity chromatography columns.

MHC:peptide complexes may be bound to hydrazide coated glass beads. Alternatively, molecules having affinity for irrelevant molecules may be bound to glass beads coated with a hydrazide linker and may be used to bind a irrelevant molecule-containing liposome:MHC:peptide complexes. A slurry of either of the above coated bead solid supports is incorporated into a compartment of a column such as that shown in FIG. 8 in a controlled fashion. Polymorphic T cell populations contained in a liquid medium are then introduced into the column, and the mixture is incubated at room temperature for 30 minutes, with gentle turning of the column. T cells with irrelevant specificity are not bound by the slurry and will flow through. Peptide or antigen-specific T cells that bind during mixing are then removed from the solid supports by incubating the column at 4° C. for 30 minutes.

EXAMPLE 12

Ex Vivo Depletion of Cells Related to a Pathogenic Process: Antigen-Specific Leukapheresis In certain situations, it is desirable to deplete living systems of T cells having specificity for a given antigen. In the case of autoimmunity or allergy, these T cells may be involved in pathogenic processes and their depletion may therefore induce clinical improvement. Likewise, in the case of transplantation, recognition of a donor's epitopes and ideotopes as non-self will cause graft vs. host rejection of a transplanted organ. In such instances, depletion of the recipient's T cell population that recognize the foreign epitopes/ideotopes is beneficial. Depletion of such reactive T cells may be accomplished by connecting in line with the general circulation of a patient a device comprising MHC:antigen complexes bound to a solid support and oriented to optimize TCR:complex interaction. For example, MHC:peptide complexes may be associated in liposomes containing irrelevant molecules which may themselves be captured by glass beads coated with molecules having specificity for the irrelevant molecules. Appropriate filters, sterilization and heating procedures may be used in a manner similar to that currently employed in conventional leukaphoresis procedures. In operation, whole blood or blood enriched for T cells is allowed to flow through the device. Antigen-specific T cells are bound and eliminated from solution. The slurry is continuously stirred, and after appropriate time periods portions of it are incubated at 4° C. in order to elute the antigen-specific T cells that have bound to the solid support associated MHC:antigen complexes. For clinical conditions where such antigen-specific T cells are harmful, such cells can be simply discarded.

The specific procedure with respect to autoimmunity comprises:

(i) Preparing a column in which the MHC:antigen:accessory molecule:other molecule complex is designed to interact with T cells which may be involved in the pathogenesis of autoimmune disease using methods described in Example 11.

(ii) Allowing blood from the patient to flow through the column containing artificial APC prepared in step (i), by which means antigen specific T cells will be retained.

The specific procedure with respect to transplantation comprises:

(i) Preparing a column in which the MHC:antigen:accessory molecule:other molecule complex is designed to interact with T cells which may be involved in either the graft vs. host disease of bone marrow transplant or the pathogenesis of graft destruction in allogenic solid organ transplant using methods described in Example 11.

(ii) Allowing blood from the patient to flow through the column containing artificial APC prepared in step (i), by which means antigen specific T cells will be retained.

EXAMPLE 13

Ex Vivo Manipulation of Antigen Specific T Cells: Bidirectional Switch From Th1 to Th2-Type Functional Phenotype In the case of infectious disease or cancer, it may be beneficial to isolate cells with a given antigen specificity in order to change their functional phenotype, for example, by manipulating such cells using the artificial antigen presenting cells described in this Example. Manipulated cells can then be reintroduced for immunomoduation.

Antigen-specific T cells, isolated according to Example 1 or Example 2, are incubated with the appropriate variant of the artificial antigen presenting cells according to the following examples.

Expansion of antigen-specific T cells.

Isolated cells (10,000/ml) are incubated in standard culture medium with APC expressing the relevant MHC:peptide combination, ICAMI as adhesion molecule to facilitate initial interaction, and anti-CD28 transmembrane antibody. The latter is employed as a co-stimulatory molecule to induce T cell proliferation without affecting Th bias. This type of approach is the antigen-specific equivalent of the recent approach at T cell expansion using anti-CD3/anti-CD28 molecules. Up to 20 replicative cycles have been obtained in this system, which represents a valid alternative to T cell expansion and cloning using autologous APC systems, often an insurmountable hurdle in human systems.

Expansion and immunomodulation of cells from a Th1 to a Th2 functional phenotype.

i) In one expansion, B7-1 may be used as a co-stimulatory molecule instead of anti-CD28. The cells obtained from this treatment may exert an immunoregulatory function in the autoimmunity condition.

ii) In another expansion, B7-2 may be used as a co-stimulatory molecule instead of anti-Cd28. Cells obtained from this treatment may have immunomodulatory properties in settings such as cancer or infectious disease.

Specifically, an artificial APC comprises MHC:peptide complexes stabilized into liposomes, with the addition of transmembrane proteins which accomplish co-stimulatory functions. The molecules may comprise any or all of the following:

a) ICAMl as adhesion molecule to facilitate initial interaction between the T cell and the APC.
b) anti-CD28 transmembrane antibody is employed as a co-stimulatory molecule which may induce T cell proliferation without affecting Th bias. This type of approach is the antigen-specific equivalent of T cell expansion using anti-CD3/anti-CD28 molecules. Up to 20 replicative cycles have been obtained in this system, which represents a valid alternative to T cell expansion and cloning using autologous APC systems.
c) B7.1 may be used instead of anti-CD28. The cells obtained from this treatment may exert immunoregulatory function in autoimmunity.
d) B7.2 may be used instead of anti-CD28. The cells obtained from this treatment may have immunomodulatory properties in settings such as cancer or infectious disease.

All of the aforementioned molecules are transmembrane proteins which can be incorporated into liposomes according to above examples, or as an alternative, bound to a solid support as in above examples.

Isolation and immunomodulation of antigen specific T cells.

Antigen-specific T cells isolated according to the above examples are incubated with the appropriate variant of the APC according to the desired objective, i.e. expansion, functional phenotype switch, etc.

EXAMPLE 14

Monitoring Immunological Outcome of Intervention of Antigen-Specific T Cells by Correlation of Clinical Outcome with T Cell Phenotype In this example, the invention is applied to evaluating the clinical outcome of treatment regimens by correlating the phenotype of antigen-specific T cells with clinical outcome. Specifically, the invention is applicable to clinical monitoring and clinical trials where there is a need to evaluate the effectiveness of artificial APC induced T cell responses. The antigen-specific T cells associated with a response (or disease state) are identified followed by the identification of their functional phenotype. The phenotype identified is then correlated and monitored against the progression of a patient's response to various treatment regimens.

EXAMPLE 15

Interaction of Artificial APCs with T Cells to Induce Capping of Transmembrane Proteins The immune synapse is the cluster of transmembrane molecules which ensures specific interaction between antigen specific T cells and antigen presenting cells. The outcome of these interactions is antigen specific response by the T cells, mediated by signaling through the TCR. Several factors contribute to significant quantitative and qualitative differences in the response provided by the T cell. These factors include affinity of interaction between MHC and peptide, and between the TCR and the MHC/peptide complex, the number of moieties Available for interaction, and the relative concentration of the moieties available for interaction. In a physiological situation, the triggering number of interacting molecules is achieved by "capping", a phenomenon, which occurs when transmembrane molecules are allowed to freely migrate to definite zones of the membrane, usually upon initial interaction between two of the ligands involved, in this case the TCR and the MHC/peptide complex. In order to emulate such physiologic mechanisms, we employed artificial APCs loaded with the combination $IA^d$/OVA, and hybridoma 8DO as the specific T cells. To visualize free movement of the TCR in the T cell membrane, we employed a system where FITC-conjugated cholera toxin, a molecule known to combine with the intracellular portion of transmembrane molecules, is introduced into the T cells. We show here for the first time that artificial APCs can effectively emulate the physiologic interactions between T cells and APC, particularly with respect to allowing migration of molecules whose proper density is an essential requirement to induce T cell activation. Our system has also the potential to be a tool to study physiological mechanisms of T cell activation, and to manipulate the intensity and quality of T cell response. This could be accomplished by controlling the affinity of the interaction, and by adding the proper co-stimulatory and adhesion molecules to the artificial APC.

Approximately 100 MHC/peptide binding sites are available on each artificial APC for interaction with a single T cell, increasing therefore the likelihood that artificial APCs will engage, through multiple interactions, low-affinity T cells. This may provide a significant advantage over current methods for the identification of low affinity, class II restricted antigen-specific T cells, such as the ones often involved in physiologic regulatory mechanisms or in disease related autoimmune responses.

We first identified the optimal incubation times for the artificial APC with the T cells, (i.e., about 20 minutes) at different stages of evolution in the capping mechanism. Unlike systems where the interacting molecules are fixed on planar membranes, interactions between T cells and artificial APCs occur in culture medium, and rely on random movement for molecular interactions. This results in the optimal period for a result to be based on formation of "capping" of the TCR in the cell membrane rather than just binding of the TCR and target moieties. In the experiments shown in FIGS. 16–18, we incubated the artificial APC with 8DO cells for 20 minutes, and evaluated the capping by confocal microscopy. In FIGS. 16A–D, we visualized co-migration of the cholera raft and the TCR, by incubating T cells with PE-conjugated monoclonal antibody (Pharmigen). TCR molecules are uniformly distributed in the cells membrane, as expected for cells, which are not interacting with stimulatory triggers. In experiments described in FIG. 17A–D, we visualized interaction of TCR by using the cholera toxin raft, and the MHC in the artificial APC membrane using a specific anti-MHC (Pharmigen) monoclonal, Alexa-red conjugated. In the field shown, the phenomenon of progressive migration of the TCR molecules toward the point of initial interaction of the artificial APC with the TCR is evident at different stages for different cells. In experiments described in FIGS. 18A–D, we visualized the TCR using an Alexa red-conjugated anti CD3 monoclonal (Molecular Probes, Eugene, Oreg.) and the liposomes using FITC-conjugated streptavidin which bound to the biotin at the N-terminal of the OVA peptide. The results of this visualization procedure in FIG. 18 are overlapping with those shown in FIG. 17. Hence, we show here for the first time that artificial APCs can effectively emulate the physiologic interactions between T cells and APCs, particularly with respect to allowing migration of molecules whose proper density is an essential requirement to induce T cell activation. Our system also provides for studying physiological mechanisms of T cell activation and the manipulation of the intensity and quality of T cell response. This "modulation" of T cell response could further be accomplished by controlling the affinity of the interaction by adding the proper co-stimulatory and adhesion molecules to the artificial APC. An additional preferred advantage of the system of the invention is that it allows free movement of transmembrane proteins, enabling the sequential order of interactions among ligands, which occur upon first contact of the TCR with the APC in the immune system.

Immunohistochemistry Methods for FIGS. 16–18

Liposomes and $0.5 \times 10^5$ cells were cytospinned at 300 g for 5 min on poly-L-lysine coated slides (Sigma, St. Louis, Mo.). The cells were fixed for 10 minutes in 4% Paraformaldehyde, washed in PBS and then incubated for 1 hours with the antibodies anti-CD3 1Ad (Pharmingen, San Diego, Calif.), at a concentration of 2–10 µg/ml in I-Block blocking buffer (Tropix, Bedford, Mass.). Alexa 568 (red) species-specific secondary antibodies (Molecular Probes, Oreg.) were used to visualize the proteins. Coverslips were washed successively in PBS and deionized $H_2O$ for 5 min and mounted in Flouromount (Fisher, Calif.). Images were obtained with a Zeiss Confocal Laser Microscope.

EXAMPLE 16

Identification of Class II Restricted T Cells in Polymorphic Populations

Identification of antigen-specific, class II restricted T cells is much more difficult than the same identification analysis for class I restricted T cells. These difficulties stem from the lower affinity of interaction of TCR/peptide/MHC for class II restricted responses, when compared to class I. Known methodologies have identified only high affinity antigen specific T cells based on soluble recombinant molecules that provide anywhere from one to four interaction sites for TCR binding, wherein steric hindrance problems are thought to affect correct folding of the recombinant molecules and their interactions with the TCR. In contrast, our results show that MHC/biotinylated peptide complexes can effectively visualize class II-restricted hybridoma T cells regardless of affinity.

Figure 5:
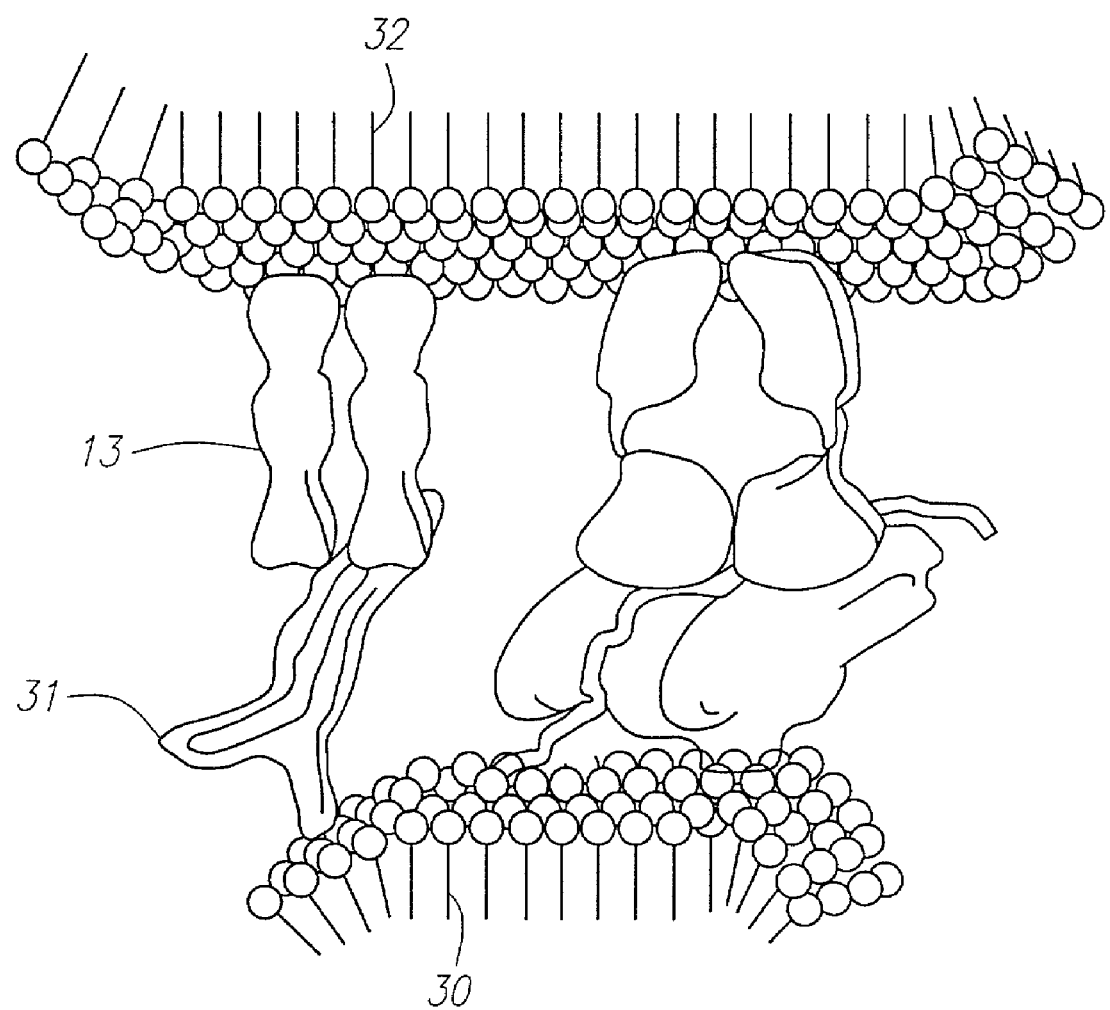
FIG. 5 is a schematic representation of an embodiment wherein the artificial APC (30) includes a functional molecule (31) (such as an accessory, co-stimulatory, adhesion, modulation, cytokine, or chemokine molecule) that interacts with a molecule (33) expressed by a T cell 32.
Figure 25A:
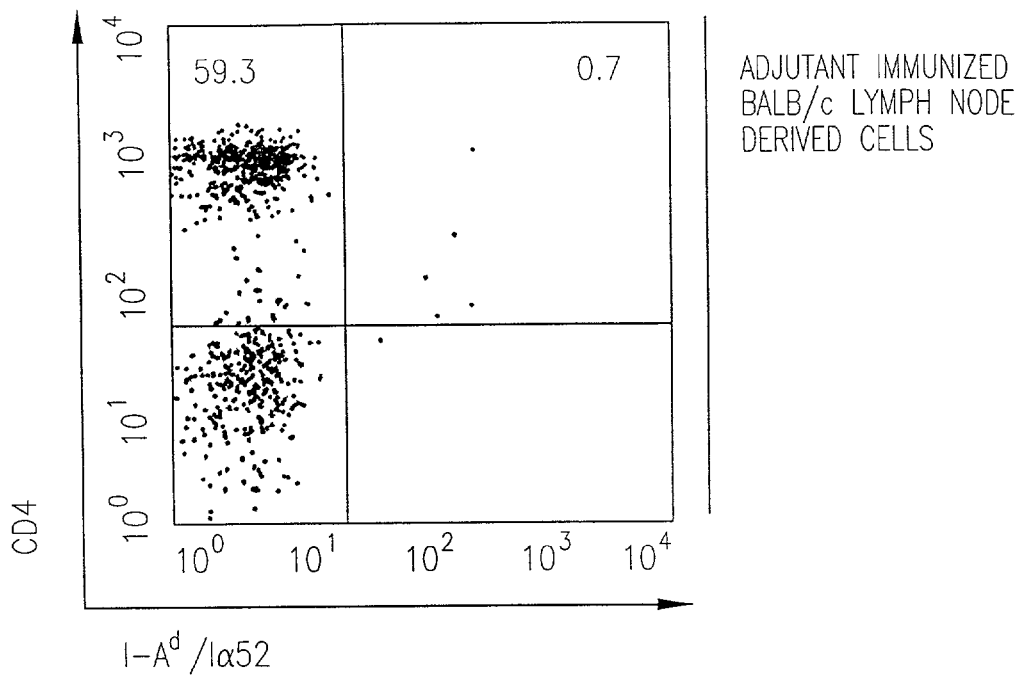
FIGS. 25A and B are FACS plots showing identification by T cell capture using artificial APCs of class II-restricted antigen specific mouse T cells upon immunization and shows increase of $IA^d/I\alpha 52$ specific cells measured after immunization of the mice (at the base of the tail) with $I\alpha 52$ or IFA (adjuvant) alone. Cells were harvested three days after the last immunization from inguinal draining lymphnodes, stained with anti-mouse CD4 PE and incubated with fluorescein labeled artificial APCs complexed with $IA^d/I\alpha 52$.
Figure 25B:
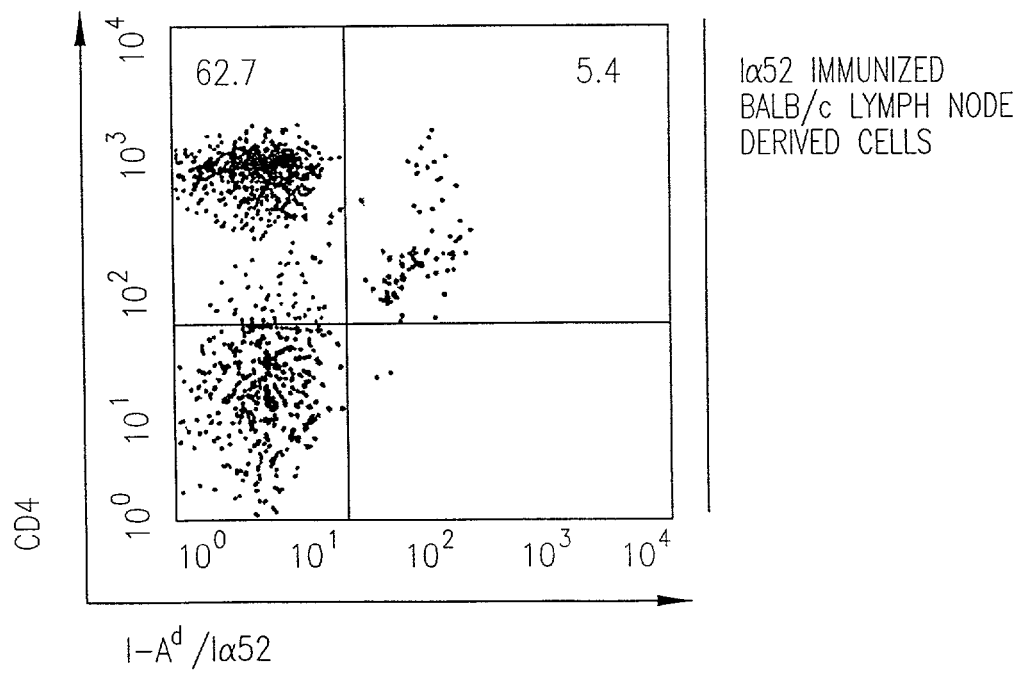
FIG. 25B shows $IA^d/I\alpha 52$-specific CD4 cells. Y axis: CD4; X axis: $IA_d/I\alpha_{52}$ specific T cells. The result indicates that the adjuvant immunized cells showed only 0.7% specific cells whereas the $I\alpha 52$ immunized cells comprised 5.4%. Thus, T cell capture using artificial APCs is useful to show antigen specificity.
Figure 26:
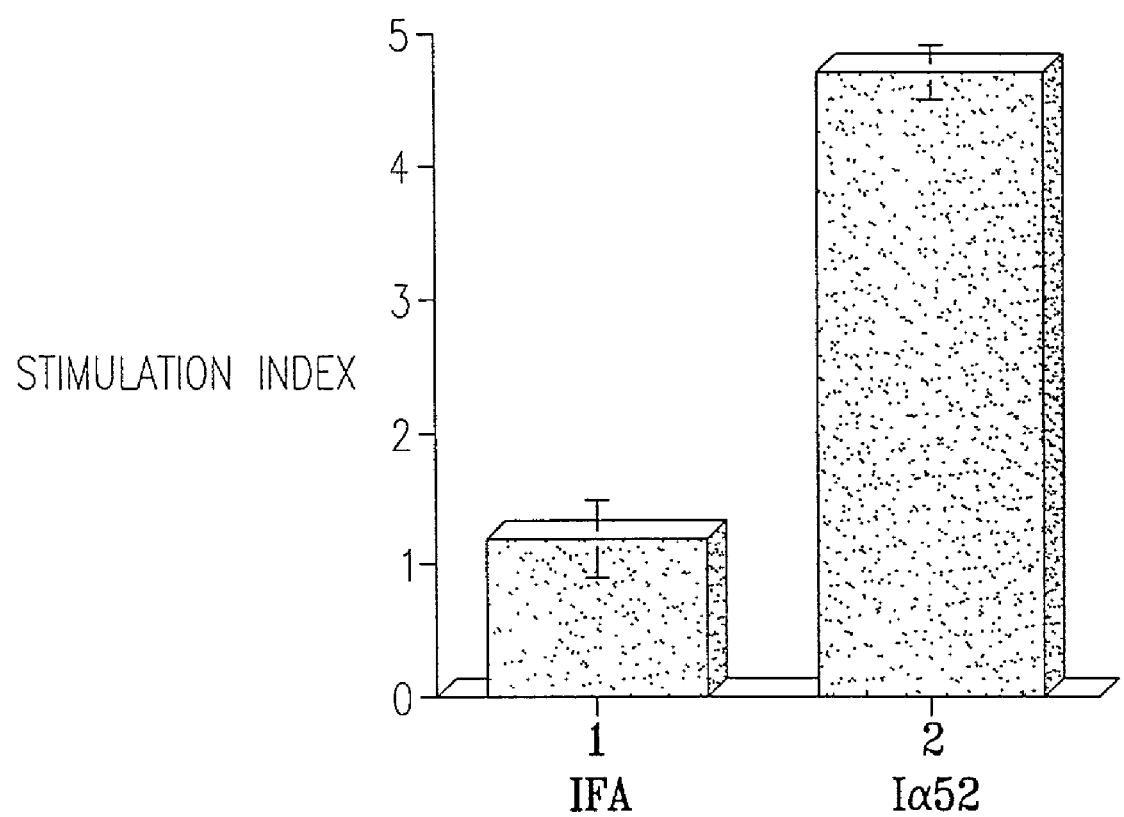
FIG. 26 is a bar graph showing T cell proliferation to $I\alpha 52$ after immunization. Cells were harvested from inguinal lymphnodes and incubated for three days with 10 mg/ml of $I\alpha 52$ peptide. Proliferation was measured by thymidine incorporation and is expressed as stimulation index "SI": cpm of stimulated/unstimulated cultures. The result indicates that conducting T cell proliferation tests to determine specificity is effective in measuring the specificity of T cell populations. However, the specificity is not to the same extent as that using the current invention shown in FIG. 25.

To evaluate the efficiency of our artificial APC system to identify Class II restricted antigen specific T cells, we immunized BALB/c mice with the peptide Iα52. Iα52, is a naturally processed, abundantly presented $IE^d$-derived peptide, which has previously been described as antigenic in BALB/c mice. Cells from regional draining lymphnodes, both from IFA only and Iα52 immunized mice, were harvested. These cells were then incubated with artificial APC presenting $IA^d$/Iα52 complexes. As shown in FIG. 25B, 5.4% of CD4+ T cells were Iα52 specific, while in comparison, only 0.7% CD4 cells were specific for the peptide in the IFA-only immunized mice (FIG. 25A). These data related well to antigen-specific T cell proliferation, measured by standard thymidine incorporation assay (FIG. 26).

Capture of T cells by Artificial APCs is Effective in Identifying Polyclonal Class II Restricted Human T Cells To identify human antigen-specific T cells, we employed as model antigens a system comprising Pan-DR binder peptides (PADRE) of comparable affinity, and the influenza hemoagglutinin HA peptide. The peptides used were pan-DR binding peptide 965.10 PADRE (K(X)VAAWTLKAA Seq. Id. No. 7), HA 307–319 (PKYVKQNTLKLAT Seq. Id. No. 8), and 1Ad binding peptide OVA 323–339 (ISQAVHAAHAEINEAGR Seq. Id. No. 9). Peptides were synthesized as C-terminal amides, purified by reversed-phase HPLC, and checked by fast atom bombardment mass spectrometry. For use in MHC-binding assays and the T cell capture, peptides were biotinylated during peptide synthesis (only one biotin molecule, at the n-terminus, 100% biotinylation).

Figure 23A:
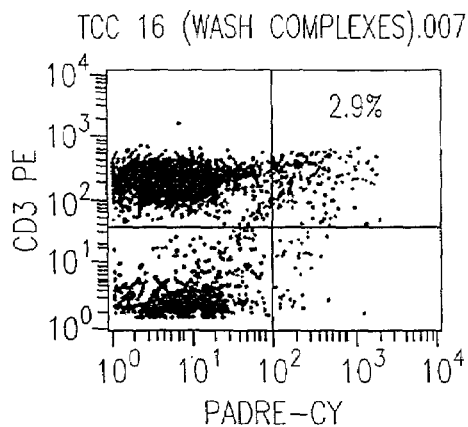
FIGS. 23A–F show plots of FACS analysis showing that T Cell capture is an effective method to identify class II restricted human polyclonal T Cells. The panels show a comparison of CD3+ cells binding PADRE/HLA or HA/HLA (HA is hemoglutinin A) complexes. PADRE is used as positive control because it will bind many MHC molecular species thereby providing an easy means to visualize populations of specific cells. HA is also a pan DR binding peptide but because cells in this example are expanded using PADRE peptide, use of HA for binding should serve as a negative control. The Y axis represents CD3+ cells; The x axis represents HLA/PADRE or HLA/HA complexes. Panels A and B show the % of PADRE antigen specific T cells at day 0 of culture (A) (i.e., 2.9%), and the % of antigen specific T cells at day 10 of culture with PADRE (B) (i.e., 8.1%). Thus, cells appear to be expanding as an antigen specific fashion. To test the specificity of the cell population, the % of HA cells are tested. As shown in panels C and D respectively, the % of HA specific T cells after 0 days of culture with PADRE/HA(C)(i.e. 1.0%) drops to 0.3% HA specific T cells after 10 days of culture with PADRE (D). Panels E and F show the % of antigen specific T cells at day 10 of culture wherein T Cell Capture using APCs was inhibited with an equimolar ratio of non-biotynilated PADRE. Panel E shows that 50% of inhibition was achieved, (i.e., the label does not interfere with testing of specificity using the APC). Panel F shows that 50% of inhibition was also achieved showing that the T cell/APC binding depends on the specific interaction of the T cell receptor, i.e., inhibition of binding using Anti HLA DR antibody at a molar ratio of 0.5:1 antibody to HLA. The FACS plots show results from an experiment wherein PBMC from a HLA DR4 0401+donor were stimulated with 10 µg/ml of PADRE peptide, K(X)VAAWTLKAA (Seq. Id. No. 7) where X is a derivatized amino acid such as cyclohexylalanine. At days 4 and 7, 10 ng/ml IL-2 was added. At day 10 cells were harvested for T Cell capture. HLADR4 was complexed with NBD-labeled liposomes (1:7 ratio HLA to liposomes) through 48 hours dialysis against PBS in 10.000 M cutoff dialysis membrane (Pierce). Complexes were then incubated for 48 hours at RT with n-terminus biotinylated peptides at a molar ratio of 10:1 for peptide/HLA. Excess of unbound peptide was removed through 24 hours of dialysis against PBS. Liposome-HLA-peptide complexes were incubated for 30 minutes with streptavidin-Cy before adding to the cells. The liposome-HLA-peptide complexes were then incubated with the stained cells and run on a Becton Dickinson FACS Star. Gates were set on viable cells, isotype controls and cells incubated with streptavidin CY alone.
Figure 23B:
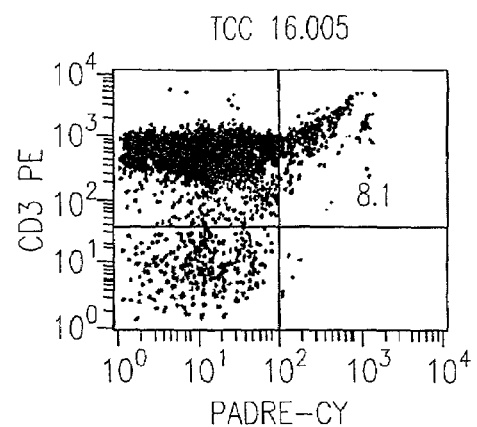
Figure 23C:
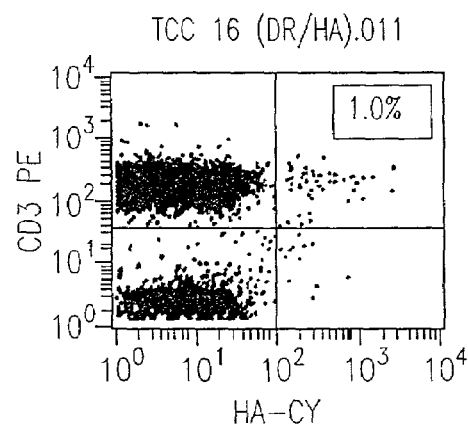
Figure 23D:
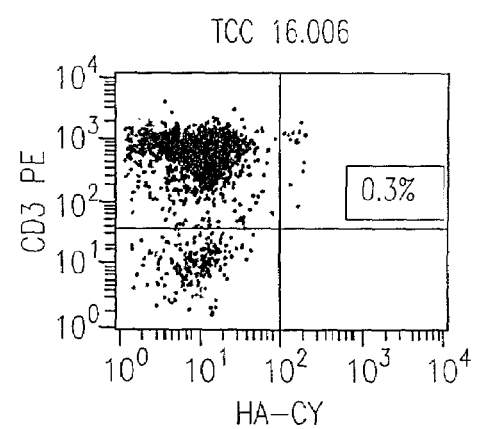
Figure 23E:
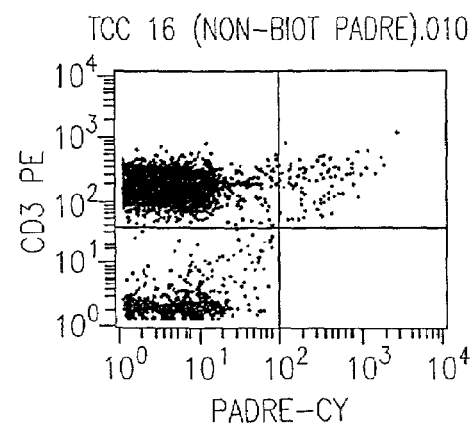
Figure 23F:
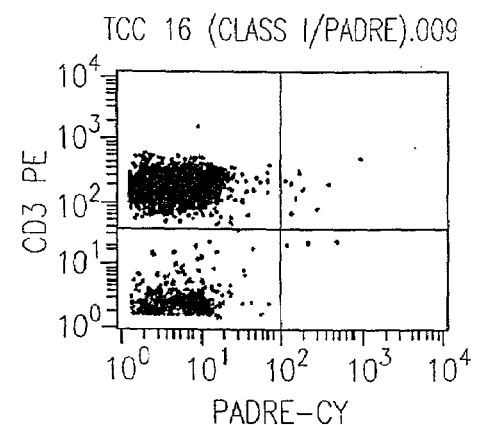

The choice of such antigens was based on the concept that a high number of polyclonal T cells could be found in PBMC if a peptide with high affinity would be employed in the assay. We first defined the optimal molar concentration to employ in loading PADRE pan-DR peptide KXVAAWTL-KAA Seq. Id. No. 7, and showed the specificity of interaction between the PADRE peptide and the HLA molecules. T cells from a normal HLA DRB 1*401 donor were first tested for the number of PADRE and HA-specific T cells (FIG. 23A), and then cultured with 10 µg/ml of PADRE for ten days. As shown in FIG. 23B, PADRE-specific T cells were expanded to 8.1%, while the number of cells specific for the control HA peptide actually decreased from 1.0 to 0.3% (FIG. 23D). Interaction between antigen-specific T cells and artificial APC was, as expected, depending on availability of TCR and HLA/peptide molecules. Our experiment further showed that binding was inhibited by addition of anti-HLA antibody prior to incubation of artificial APCs with the T cells. Moreover, both total cell number and MFI were reduced by 62% when compared with panel 23B upon competition between biotinylated and non-biotinylated PADRE peptides. This control further supports the specificity of the interactions between the various components of the system, and rules out the possibility of steric hindrance from the biotin at the n-terminal of the peptide in interfering with the necessary molecular interactions.

T cell capture by artificial APCs is more sensitive than measurement of cytokine production to assess the number of antigen specific T cells in a culture.

Figure 24:
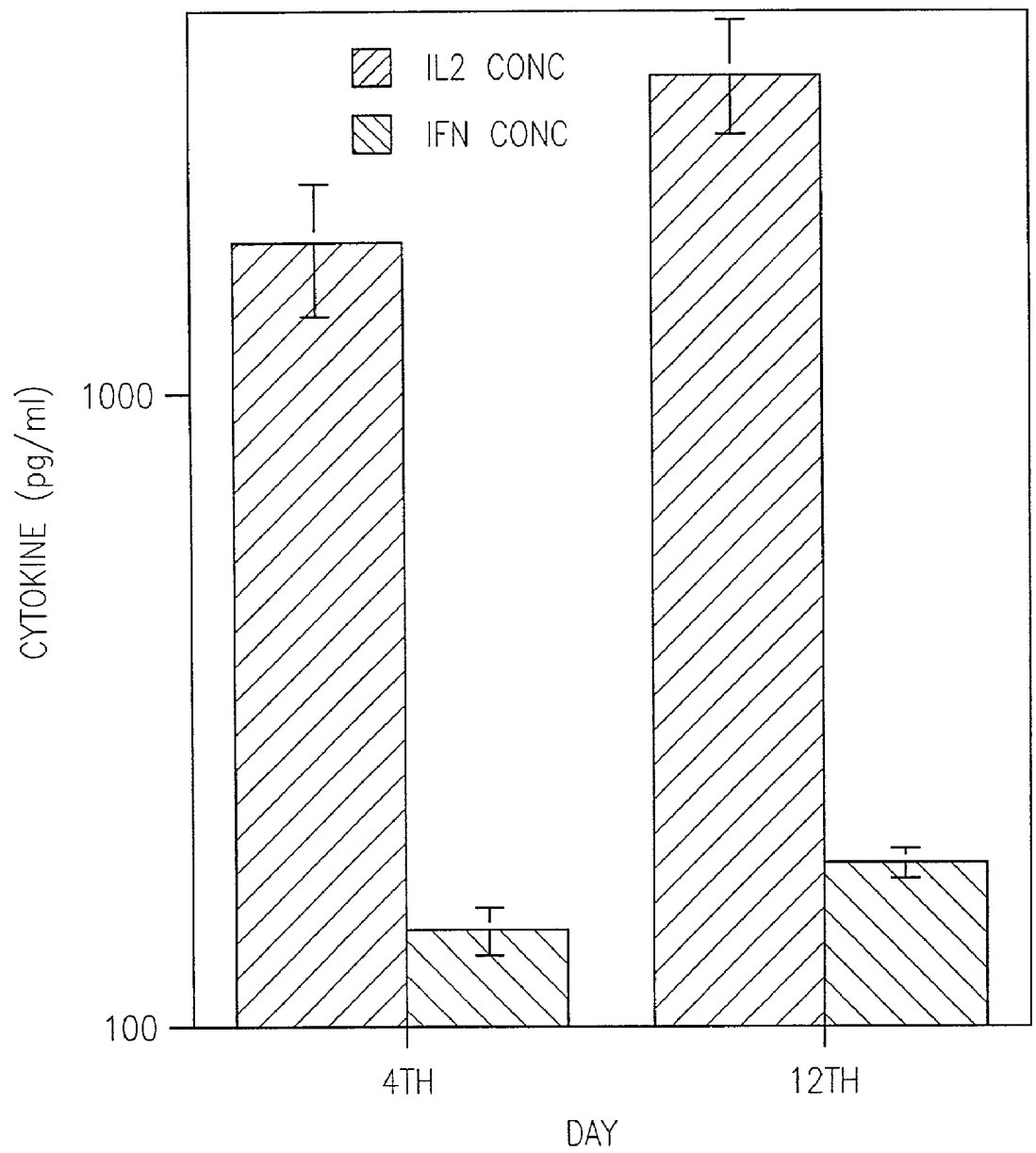
FIG. 24 is a bar graph showing cytokine production by PADRE-stimulated cells. Production of IL2 and IFN in vitro of PBMC from HLA DR 0401 healthy adults. PBMCs were initially stimulated with 10 µg/ml of Pan DR Epitope binding peptide (PADRE) and cultured for 10 days. The cells were restimulated with autologous APCs and 10 µg/ml of peptide. Culture supernatants were collected at different days and measured for cytokine production by capture ELISA method. The result indicates that cell specificity can be shown by measuring cytokine production as cells proliferate. However, measuring cytokine production is actually less specific than the method of the invention as demonstrated in FIG. 23.

Measurement of production of cytokines in response to an antigen is often used to estimate the number of antigen specific T cells. To compare sensitivity of measuring cytokine production against T cell capture by artificial APCs, we harvested culture supernatants from PADRE-stimulated cultures, at the fourth and sixteenth day of culture and measured concentrations of IL-2 and IFN γ by sandwich ELISA. As shown in FIG. 24, the differences in IL-2 and IFN-γ production between the two time points were not as evident as the increase in PADRE-specific T cells, as measured by our T cell capture method (FIGS. 23A–F). Hence, from the comparisons of the T cell capture using artificial APCs with antigen induced T cell proliferation (FIGS. 25 and 26) and cytokine production (FIG. 24) it appears evident that T cell capture using artificial APCs is a tool for sensitive measurement of antigen-specific responses. The advantage of identifying specific T cells by T cell capture is also important for the fact that T cells may not directly participate in antigenic responses while retaining antigen specificity. This phenomenon may also provide an important tool for the understanding of the regulation of T cell responses to antigens.

Methods

Short Term T Cell Line

Peripheral Blood Mononuclear Cells (PBMC) from healthy donors were stimulated in vitro with the PADRE peptide. PBMC were isolated using a Ficoll-Isopaque gradient and stimulated in vitro with 10 µg/ml PADRE peptide in a 24 well tissue culture plate (Costar, Cambridge, Ma) at $4 \times 10^6$ cells per well. The cells were cultured in RPMI containing 15% AB serum, at 37° C. and 5% $CO_2$. At days 4 and 7, media were replaced with fresh medium containing recombinant human Interleukin-2 (IL-2) at a final concentration of 10 ng/ml. Culture supernatants taken at day 4 were analyzed for production of IL-2 and Interferon-γ by ELISA. At day 10 viable cells were harvested and analyzed in a T cell capture as described below.

Animals

Balb/c mice were obtained from Harlan. Mice were 4–6 weeks old at the beginning of each experiment.

Immunizations

Balb/c mice were immunized with 100 mg of OVA 323–339 in Complete Freundis Adjuvant (CFA) subcutaneous, followed by immunizations with 100 mg of OVA 323–339 in Incomplete Freundis Adjuvant (IFA) at days 7, 14 and 21 after the initial immunization. A subgroup of mice was sacrificed 5 days after each immunization.

Preparation of MHC

Balb/c MHC class II molecules I-Ad and I-Ed were purified from the lysate of B cell lymphoma A20.11 by immunoanaffinity chromatography using anti-IAd monoclonal antibody MKD6 (Pierce) and anti-IEk monoclonal antibody 14-4-4S, essentially as previously described.

Human MHC Class II DRB1*0401 and MHC Class I molecules were purified from the lysate of the Epstein Barr virus transformed B cell lines.

Affinity purified MHC molecules were solubilized in a TRIS buffer containing 50 mM diethylamine and 0.2% n-acetyl-octyl-glucopyranoside (Calbiochem, San Diego). Conditions tested: pH5 and 7, RT and 370° C., 16–24–40 hr peptide loading.

Competition/inhibition of non-biotinylated PADRE peptide on binding to HLA DR4*0401.

A modified ELSA using soluble HLA-DR 0401 assessed the competition/inhibition of biotinylated and non-biotinylated PADRE peptide. A ten-fold molar excess of biotinylated PADRE peptide was incubated with affinity purified DR4*0401 at pH 7.0 for 16 hrs in room temperature. In addition, a 250 fold molar excess of non-biotinylated PADRE was added. After 16 hours the complexes were transferred to a 96-well flat bottom ELISA plate (Costar) coated with an anti-DR capture antibody. The excess of unbound peptides and complexes were removed trough extensive washing with buffer. A 1:20,000 solution of Neutravidin-HRP was then added to the wells and incubated for 40 minutes in room temperature. After washing, a TMB developing solution was added and developed for approximately 15 minutes. 1M H3PO4 was used as a stop solution. The optical density was read at 450–650 nm using a microplate reader. Delta Soft program was used to analyze the data.

Preparation of Cells

Cells were washed twice in staining buffer (PBS with 2% PCS and 0.05% sodium azide) and then incubated at 4° C. for 20 minutes in blocking buffer (staining buffer with 10% FCS, for mouse cells FcBlock (Pharmingen) is used). The cells were stained for the surface markers and isotype controls for 20 minutes at 4° C., and washed twice and resuspended in staining buffer. The following monoclonal antibodies were used: PE-, CY- and FITC-labeled anti-mouse and anti-human CD3 and CD4.

T Cell Capture

The cells were incubated with the MHC-peptide liposomes for 20 minutes at room temperature. Before acquisition on the FACScan, cells were washed twice (5 minutes, 500 g) and resuspended in staining buffer. Partial inhibition of the interaction of cells to the liposomes was achieved with monoclonal antibodies against T cell receptor or MHC. For inhibition through partial blocking of the T cell receptor, cells were incubated for 20 minutes with 50 μg/ml unlabeled anti-TCR antibody (Pharmingen), prior to the incubation with the liposomes. For inhibition through partial blocking of MHC, the liposomes were incubated with unlabeled anti-MHC at a molar ratio of 1:1 to incorporated MHC. For competition/inhibition with non-biotinylated peptide, non-biotinylated peptide was added together with the biotinylated peptide, and at the same molar ratio to the MHC.

EXAMPLE 17

Characterization of Artificial APCs

Figure 20:
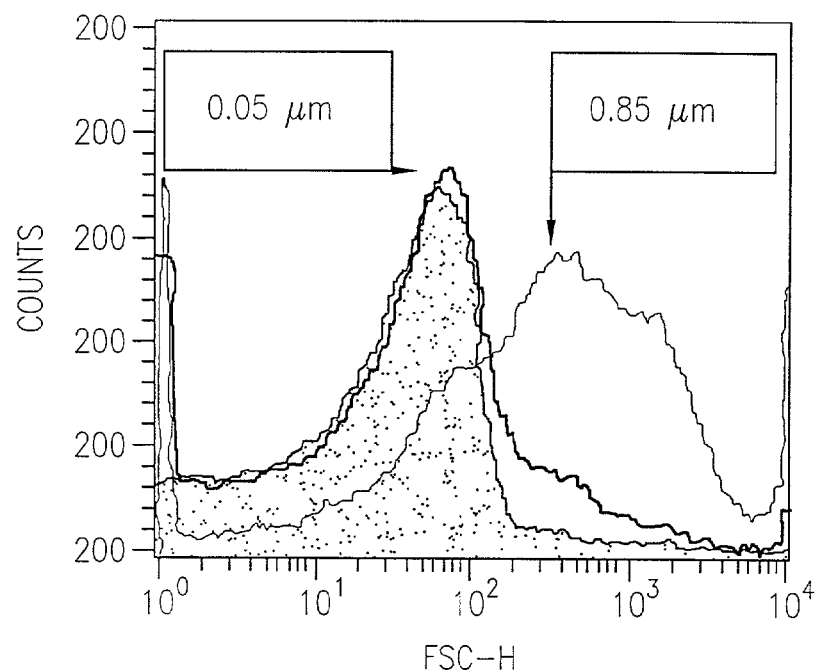
FIG. 20 is a graph showing characterization of the artificial APCs by flow cytometric analysis wherein the approximate size of the fluorescent-labeled liposomes was determined through comparison with single size fluorescent particles with a mean size between 0.05 μm and 0.85 μm. The 0.85 um labeled curve represents beads of 0.85 μm diameter, while the curve labeled 0.05 represents beads of 0.05 μm in diameter, the shaded curve represents the size of APC.
Figure 21:
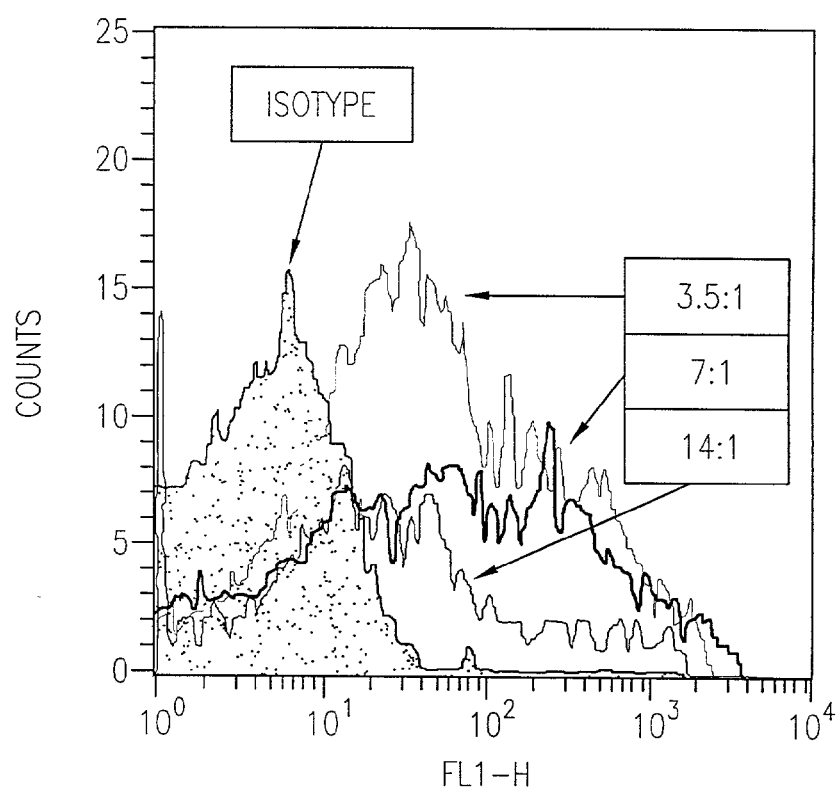
FIG. 21 is a graph showing determination of the optimum incorporation of MHC class II in liposomes. Optimum incorporation is a factor of the ratio of the phospholipid and cholesterol. The ratio of the lipid components were tested such that fluorescent labeled liposomes were complexed with HLA DR4 where the ratio was from 3.5:1 (w/w) to 14:1 and stained with anti-HLA DR PE. The incorporation of DR4 was measured by means of flow cytometric analysis of the signal for HLA DR-PE in FL2 (X-axis). As shown the number of incorporating events is highest (x axis) at a lipid/cholesterol ratio of 7:1.
Figure 22:
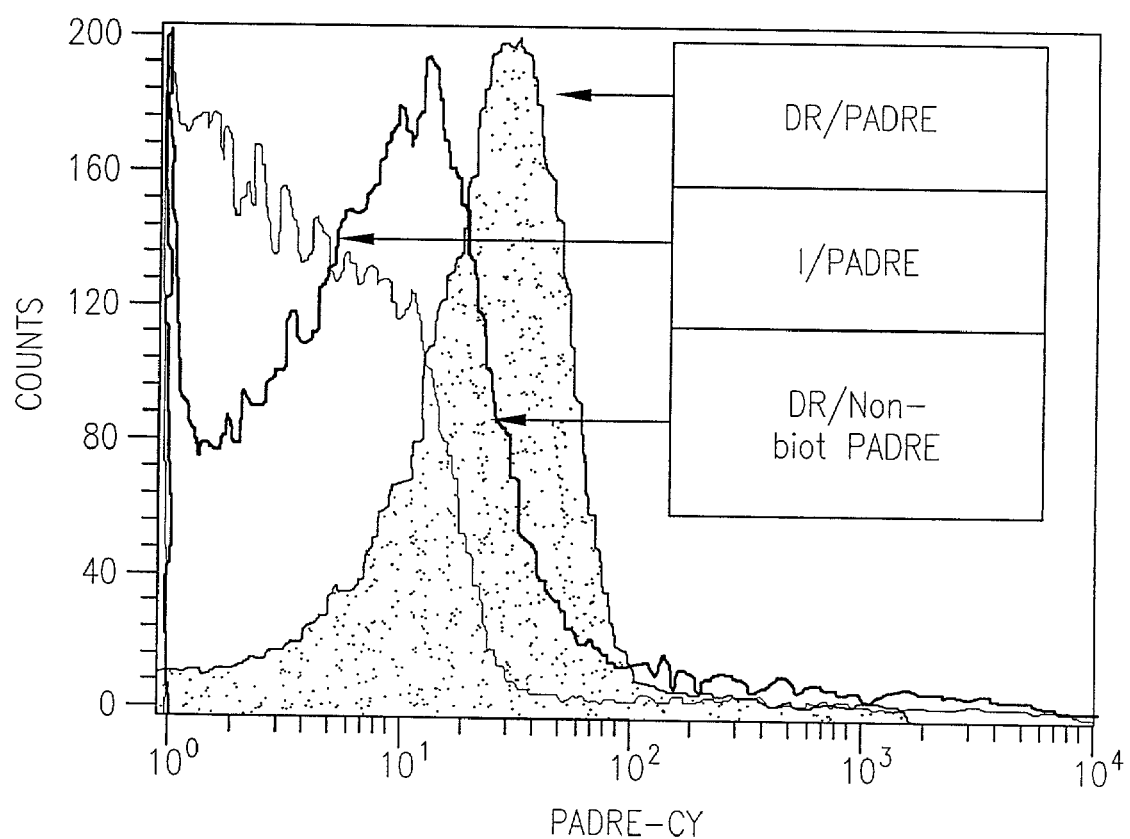
FIG. 22 is a graph showing incorporation of biotinylated PADRE in fluorescent labeled liposomes, complexed with HLA DR4 and specificity of the binding of biotinylated PADRE peptide to HLA DR4 complexed with liposomes. Biotinylated PADRE peptide is incubated with HLA DR4 or MHC Class I, both at a molar ratio of 10:1 (peptide to MHC) prior to incorporation in artificial APCs with fluorescent lipids. As an additional control, non-biotinylated PADRE peptide and biotinylated PADRE peptide (at a 1:1 w/w ratio) were incubated with HLA DR4 before incorporation in artificial APCs. The PADRE is a pan DR binding peptide. The graph indicates specificity and that label bound to the PADRE does not interfere with binding to the MHC component. Specifically where non-biotinylated peptide is used at the same time, it will compete out biotinylated. The Class I binding shows that there must be specificity for such binding as use of the Class I fails to bind PADRE.

Mean particle sizes of the MHC-containing liposomes were determined through dynamic light scattering analysis with a Malvern 4700 system, using a 25 mW Ne—He laser and the automeasure version 3.2 software (Malvern, Ltd.). For refractive index and viscosity the values for pure water were used. The particle size distribution was reflected in the polydispersity index (p.i.:0, which ranges from 0.0 for a monodisperse to 1.0 for a polydisperse dispersion). Besides DLS analysis, liposomes were visualized through flow cytometric analysis as described before herein. Briefly, FITC-labeled liposomes were gated according to their FL1 fluorescence by placing a threshold at the FL1 channel, while for forward and side scattering the most sensitive settings were selected. The size of the FITC-liposomes was compared with the FSC of 2 types of FITC-labeled calibration beads ranging in sizes from 40 to 60 nm and from 700 to 900 nm (Pharmingen). The results are shown in FIG. 20 wherein the shaded area shows that the artificial APCs size peak is in the range of 0.05 μm.

For qualitative analysis of the MHC class II incorporation efficiency as explained in Example 16, MHC class-II liposomes were incubated with PE-labelled anti-MHC class II mAbs (anti-DR4 (Parmogen); anti-I-Ad (clone 0X-6, Harlan)) or PE-labelled isotype controls and analyzed for PE-staining on the FACS calibur. MHC incorporation was quantitatively analyzed by a Petterson modification of the Lowry protein assay. Briefly, a standard curve (0–1–2–4–6–8–12 μg of MHC) was made with the same detergent solubilized MHC batch as used for the preparation of the artificial APC. A reliable range for protein determination was between 2–12 mg of MHC. All samples were analyzed in duplicate and linear regression was performed on the standard curve to evaluate the amount of protein incorporated in the liposome preparation. To calculate the number of MHC molecules per liposome, the amount of MHC, as determined by the Petterson modified Lowry method, and the size of the liposomes, as determined by DLS, were used to convert the amount of incorporated MHC into the number of MHC per liposome, assuming that a 100 nm liposome contains approximately 80,000 phospholipid molecules/vesicle, and assuming that the average area per phospholipid molecule is 75 μm$^2$.

For qualitative analysis of peptide loaded MHC class II molecules, MHC molecules were preloaded with biotinylated-peptide using the optimized peptide-MHC loading conditions. After MHC incorporation, the artificial APC were incubated with Streptavidin-CY (Pharmingen), and analyzed for FL3 staining using the FACS calibur. The quantitative analysis of occupancy of the number of MHC molecules with the desired peptide was performed in 2 different ways, namely, soluble ELISA and by the analysis of unbound biotinylated peptide after SDS-PAGE and blotting of MHC molecules incubated with peptide.

In addition to the MHC samples incubated with a dose range of biotinylated peptide, the same dose range of biotinylated peptide was incubated under exactly the same experimental conditions without the addition of MHC. After 24 hrs., two gels were run under identical conditions in one minigel-system (Biorad). One gel was loaded with the MHC-peptide samples, while the other gel was loaded with the peptide samples. The fronts of the gels were scanned by using the Molecular Analyst software (Maxsott), and a standard curve was made by linear regression of the peptide loaded gel. After front analysis of the MHC-peptide gel the decrease of the peptide signal was quantified by comparison with the standard curve and consequently, the amount of MRC bound peptide could be determined, (see FIG. 19).

Methods

Peptide Loading of MHC Class II Molecules

To determine optimal loading conditions for MHC class II molecules a MHC class II binding assay was performed, essentially as described before with minor modifications. Briefly, detergent solubilized MHC class II molecules (0.5–1 µM) were incubated with a 50–250-fold molar excess of biotinylated peptide for the designated time, pH and temperature without the addition of protease inhibitors. The following conditions were tested; pH 5 and pH 7; Room Temperature and 37° C.; 16, 24 and 40 hours of peptide loading; 0.05-, 1-, 10-, 100-fold molar excess of peptide. For DRB1*0401 0.5 µM, for I-Ad 3 µM of MHC was used in binding assays.

MHC-peptide complexes were analyzed via a non-reducing SDS-polyacrylamide gel electrophoresis (SDS-PAGE). Following Western Blotting (Highland-ECL, Amersham), the biotinylated peptides were visualized on preflashed films (Hyperfilm, Amersham) through enhanced chemiluminescence (Western blot ECL kit, Amersham). Optimal binding conditions were established by evaluation of the density of the spots at the position of the MHC class II dimer-peptide complexes. The presence of the MHC Class II dimer under the tested conditions was checked with a non-reducing SDS-PAGE followed by silver staining (Biorad). (see FIGS. 19A–D)

Preparation of Liposomes

Liposomes were prepared as follows. Stock solutions of egg Phosphatidyl Choline (Sigma) and Cholesterol (Sigma) were combined in a glass tube at a molar ratio of 7:2. N-(fluorescein-5-thiocarbamoyl)-1,2-dihexadecanoyl-sn-glyvero-3-phosphoethanolamine, triethylammonium salt (fluorescein-DHPE, Molecular Probes, Eugene, Oreg.) was added at a final concentration of 1 mol % of Phosphatidyl Choline. The solvent was evaporated under an Argon stream for 30 minutes and the lipids were dissolved at a final concentration of 10 mg/ml in a buffer containing 140 mM Nad, 10 mM Tris HCl (at pH 8) and 0.05% deoxycholate (Buffer A). The solution was sonicated until clear, and aliquoted in 500 µl Eppendorf tubes and stored at minus 200° C.

Incorporation of MHC-peptide in Liposomes

After preincubation of biotinylated peptides and MHC at conditions based on in vitro MHC binding, MHC-peptide complexes were added to the lipids in Buffer A at a ratio (w/w) of MHC:liposomes of 1:7 (DR4) or 1:10 (1Ad and 1Ed). Additionally, for each T cell capture sample a ratio of 1 µg MHC per 6000 cells was used.

The lipids and MHC-peptide complexes were dialyzed at 4° C. against PBS in a 10K Slide A Lyzer (Pierce) for 48 hours with two buffer changes. The formed liposomes were then recovered from the Slide A lyzers and incubated with streptavidin-CY for 20 minutes before adding the liposomes to the cells. For MHC staining, liposomes were stained with a PE-labeled anti-MHC antibody at the same time.

Where other molecules of interest are to be incorporated into the artificial APC (i.e., accessory, adhesion, co-stimulatory, cell modulation, irrelevant, GM-1, and cholesterol molecules), such molecules can be added simultaneously with the incorporation of the MHC:antigen complexes.

Quantification of HLA-DR and PADRE Peptide Bound to Liposomes

A modified ELISA was used to assess the amount of HLA-DR bound to the liposomes. Briefly, liposomes containing HLA DR4*0401 and biotinylated PADRE peptide were formed as described above. The resulting liposomes were counted and sorted by FACS on (FITC) fluorescence and forward scatter. The sorted samples were then divided into two lots for HLA and peptide quantification by ELISA.

DR Quantification

The sorted liposome sample was initially incubated with 10×M excess of neutra-avidin (Pierce) to cap the biotin on the peptide. This was followed by an extensive dialysis with a 300 k MWCO membrane (Pierce) to remove excess unbound neutra-avidin. The sample was then incubated with biotinylated mouse anti-DR (Parmagen) at 1:1 molar ratio, which was again followed by extensive dialysis. The tagged complex was incubated with neutra-avidin-HRP at 1:20,000 and the excess dialyzed as before. A known amount of soluble DR pre-incubated with non-biotinylated PADRE peptide (standard) was incubated with the same antibody used for detecting the DR in the liposomes. Multiple epitope recognition by the antibody assured retention of the complex during dialysis steps. Both the sorted sample and the standard were then developed with TMB-HRP substrate and read at 450–650 nm.

PADRE Peptide Quantification

The sorted liposome sample was incubated with non-biotinylated anti-DR (Pharmagen) at a 1:1 molar ratio. The sample was treated and developed in the same manner as for DR quantification described above. The peptide was quantified based on its biotin tag. Analysis of the data was adjusted to background and to appropriate negative controls.

EXAMPLE 18

Methods for Orienting Molecules of Interest in an Artificial APC

We have shown that incorporation of molecules of interest into the artificial APC liposome matrix yields insertion of such molecules in an orientation wherein the active center of the molecules face outward on the APC at a rate of about 50%. We have found that proper orientation can be dramatically increased to over 90% by applying a mechanism to direct the insertion of the molecules. This mechanism uses GM-1 pentasaccharide which is a transmembrane molecule and has an affinity for binding the P subunit for cholera toxin. When the GM-1 is associated with the liposome membrane of the APC, it can be used to bind cholera toxin which in turn can be attached to the molecule of interest. By attaching the cholera toxin to a point distal to the active site of the molecule of interest, we can direct the orientation of the molecule of interest such that the active site will be placed in the artificial APC in an orientation favorable to interaction with T cells and various molecules. In a preferred embodiment, proper orientation is obtained using a recombinant fusion between the molecule of interest and the P subunit of cholera toxin the construction of which will be well understood by those skilled in the art of making recombinant fusion proteins. The β subunit can also be connected to a molecule of interest using a linker.

Methods

GM1 Pentasaccharide

The structure of GM-1 has been elucidated and shown to be pentasaccharide. The molecule is branched having terminal sugars, galactose and sialic acid (n-acetyl neuraminic acid), which exhibit substantial specific binding interactions with the β subunit of cholera toxin. A smaller contribution to binding is derived from the N-acetyl galactose residue of the molecule. This binding interaction is mediated through hydrogen bonding. Each of the 5 identical binding sites are primarily within a single monomer of the B-pentarner. GMI ganglioside may be purchased from commercial sources (Sigma #G7641).

Cholera β Subunit (CTB)

Cholera toxin (mw=84 kda) is comprised of two subunits; α (mw=27 kda) and β (mw=11.6 kda). The amino acid sequence has been determined at about 11,604 da. The primary structure of the β subunit, which is responsible for binding of the toxin to the cell receptor ganglioside GM1, has been determined. Cholera toxin's ability to bind well to such transmembrane structures makes it very attractive anchor for membrane proteins (e.g. molecules of interest as disclosed herein). Since the β subunit is primarily involved in the binding to the GM1 pentasaccharide, the α subunits are not necessary. The use therefore of only the β subunit makes issues respecting toxicity less important with respect to use of the toxin protein subunits in therapeutic applications such as drug delivery or transport and manipulation of T cells ex vivo.

The receptor binding site on the CTB is found to lie primarily within a single β-subunit, with a solvent-mediated hydrogen bond involving the two terminal sugars of GM1 (galactose and sialic acid). The binding of GM1 to cholera toxin thus resembles a 2-fingered grip. Cholera toxin β-subunit may be purchased from commercial sources (Sigma #C9903 or C7771) or synthesized by recombinant methodology.

Linkers for Attaching Cholera Toxin to Molecules of Interest

Linkers may be used to attach the cholera toxin subunit to the molecule of interest. In a preferred embodiment, a linker such as N-succinimidyl[3-(2-pyridyl) dithio) propionate (SPDP, Sigma Prod. No. P3415). NHS-esters such as this yield stable products upon reaction with primary or secondary amines. Coupling is relatively efficient at physiological pH. Accessible α-amine groups present on the N-termini of proteins react with NHS-esters and form amides. In this regard, reaction with side chains of amino acids can also occur. A covalent amide bond is formed when the NHS-ester cross-linking agent reacts with primary amines, releasing N-hydroxysuccinimide.

In another preferred embodiment, pyridyl disulfides can be used to react with sulfhydryl groups to form a disulfide bond. Pyridine-2-thione is released as a by-product of this reaction. These reagents can be used as cross-linkers and to introduce sulfhydryl groups into proteins. Conjugates prepared using these reagents are cleavable. Pyrimidine-2-thione groups are released upon reaction with free -SHs and the concentration can be determined by measuring the absorbance at 343 nm (Molar extinction coefficient=8.08×$10^{-3}$ M-1 cm-1).

Results

The GM1 is a transmembrane molecule which can be associated with the "raft" or freely mobile molecules of interest in the lipid membrane. GMI has been used in studying movement and interactions of co-stimulatory molecules through cross-linking the molecule with flourescinated-tagged cholera toxin. This cross linking can be carried out in several ways as shown in FIG. 27. For example, in FIG. 27A, a synthetic gene encoding a molecule of interest is cloned into a commercial vector such as a generic expressions vector (for example, DES Expression Vector, Invitrogen) and expressed. The recombinant product can be purified and linked to GM-1 that is in an artificial APC. In a similar fashion (FIG. 27B) the molecule of interest can be cloned into an expression vector as a fusion protein with cholera toxin β subunit. The fusion product can be purified and mixed with an artificial APC containing GM-1 where the cholera moiety will bind to the GM-1. Additionally, as shown in FIG. 27C, the cholera toxin (whether natural or recombinant) can be attached to a linker, such as N-succinimidyl[3-(2-pyridyl) dithio]propionate, either to a complete β subunit molecule or during synthesis of a recombinant toxin molecule, the product of which can be then mixed with a GM-1 containing artficial APC.

We have found that cross-linkers are useful as "flexible hinges" where protein molecules can be covalently linked to allow for intercellular interaction with transmembrane proteins (e.g., B7-CD28, ICAM-1-LFA-1, MHCs, TCRs, etc.). Once the GM1 is incorporated into the liposome of the APC, cholera toxin-conjugated surface proteins can then be cross-linked. The system containing properly oriented molecules of interest can then be tested through ELISA, WESTERN, and by FACS analysis.

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims. All references are herein incorporated by reference.

---

What is claimed is:

1. A method of identifying a T cell specific for an antigen of interest, comprising:
   a) contacting a biological sample containing T cells specific for an antigen of interest with an artificial antigen presenting cell that presents a peptide derived from the antigen of interest in order to form a complex comprised of a T cell specific for the antigen of interest and an artificial antigen presenting cell that presents the peptide derived from the antigen of interest, wherein the artificial antigen presenting cell comprises:
      i. a liposome comprising a lipid bilayer, wherein the lipid bilayer is comprised of neutral phospholipids and cholesterol;
      ii. at least one GM-1 ganglioside molecule disposed in the lipid bilayer;
      iii. a cholera toxin β subunit bound to one of the GM-1 ganglioside molecules;
      iv. an MHC molecule loaded with the peptide derived from the antigen of interest, wherein the antigen-loaded MHC molecule is bound to the cholera toxin β subunit; and
      v. an accessory molecule that can stabilize an interaction between a T cell receptor and the antigen-loaded MHC molecule; and
   b) detecting the complex, if formed, thereby identifying a T cell specific for the antigen of interest.

2. A method according to claim 1 wherein the neutral phospholipids are phosphotidylcholine.

3. A method according to claim 1 further comprising the step of isolating from the complex the T cell specific for the antigen of interest.

4. A method according to claim 3 further comprising the step of characterizing a functional phenotype of the isolated T cells.

5. A method according to claim 1 wherein the biological sample is selected from the group consisting of whole blood, blood cells, blood plasma, and tissue.

6. A method according to claim 1 wherein the peptide derived from the antigen of interest is selected from the group consisting of a peptide derived from a recipient of a graft, a cancer cell-derived peptide, a peptide derived from an allergen, a donor-derived peptide, and a peptide derived by epitope mapping.

7. A method according to claim 1 wherein the artificial antigen presenting cell also comprises a label.

8. A method according to claim 7 wherein the label is bound to a molecule of the artificial antigen presenting cell selected from the group consisting of a neutral phospholipid, cholesterol, a GM-1 ganglioside molecule, a cholera toxin β subunit, an MHC molecule, the peptide derived from the antigen of interest, and an accessory molecule.

9. A method according to claim 7 wherein the label is selected from the group consisting of biotin, vancomycin, a fluorochrome, FITC, and a radiolabel.

* * * * *